US012609185B2

(12) United States Patent
Anderson

(10) Patent No.: US 12,609,185 B2
(45) Date of Patent: Apr. 21, 2026

(54) ARTIFICIAL INTELLIGENCE DRIVEN MONITORING SYSTEM FOR AGING WHISKEY

(71) Applicant: BARREL PROOF TECHNOLOGIES LLC, Murfreesboro, TN (US)

(72) Inventor: Brian Richard Anderson, Murfreesboro, TN (US)

(73) Assignee: BARREL PROOF TECHNOLOGIES LLC, Murfreesboro, TN (US)

( * ) Notice: Subject to any disclaimer, the term of this patent is extended or adjusted under 35 U.S.C. 154(b) by 0 days.

(21) Appl. No.: 19/084,671

(22) Filed: Mar. 19, 2025

(65) Prior Publication Data

US 2025/0266132 A1 Aug. 21, 2025

Related U.S. Application Data

(63) Continuation-in-part of application No. 19/013,859, filed on Jan. 8, 2025, which is a continuation-in-part of application No. 18/818,539, filed on Aug. 28, 2024, now Pat. No. 12,228,525, and a continuation-in-part of application No. 18/800,279, filed on Aug. 12, 2024, now Pat. No. 12,228,445, said
(Continued)

(51) Int. Cl.
| | |
|---|---|
| *G16C 20/30* | (2019.01) |
| *C12G 3/07* | (2006.01) |
| *G06N 20/00* | (2019.01) |
| *G16C 20/70* | (2019.01) |

(52) U.S. Cl.
CPC .............. *G16C 20/30* (2019.02); *C12G 3/07* (2019.02); *G06N 20/00* (2019.01); *G16C 20/70* (2019.02)

(58) Field of Classification Search
None
See application file for complete search history.

(56) References Cited

U.S. PATENT DOCUMENTS

| | | | |
|---|---|---|---|
| 1,854,122 | A | 4/1932 | Eaton |
| 3,953,856 | A | 4/1976 | Hammack |
| | | (Continued) | |

FOREIGN PATENT DOCUMENTS

| | | | | |
|---|---|---|---|---|
| CN | 119086821 A | * | 12/2004 | ......... G01N 30/8679 |
| CN | 117007550 A | * | 11/2023 | ......... G01N 21/3577 |
| WO | WO-2024028852 A1 | * | 2/2024 | ............. B60K 15/03 |

OTHER PUBLICATIONS

Translation of CN-117007550-A (Year: 2023).*
(Continued)

*Primary Examiner* — Elizabeth M Kerr

(57) ABSTRACT

This disclosure relates to an AI-driven, non-invasive system configured to analyze whiskey color and maturation outcomes based on sensor-tracked environmental and chemical variables through integrated machine-learning, high-accuracy volume sensing, dielectric-based proof monitoring, and environmental data analysis to forecast how whiskey will age inside a barrel over time, and by leveraging real-time barrel data such as time, proof, volume, temperature, humidity, and evaporation rates, the AI model can accurately analyze the final color, proof, and optimal aging duration for whiskey and other barrel-aged spirits, which can allow distilleries to reduce inconsistencies, improve yield management, and enhance quality control without relying on manual sampling or invasive testing.

20 Claims, 28 Drawing Sheets

Related U.S. Application Data application No. 18/818,539 is a continuation-in-part of application No. 18/424,758, filed on Jan. 27, 2024, now Pat. No. 12,117,329, said application No. 18/800,279 is a continuation-in-part of application No. 18/424,758, filed on Jan. 27, 2024, now Pat. No. 12,117,329.

(56) References Cited

U.S. PATENT DOCUMENTS

| | | | |
|---|---|---|---|
| 6,002,357 | A | 12/1999 | Redfern |
| 6,995,706 | B2 | 2/2006 | Ohlsson |
| 7,304,601 | B1 | 12/2007 | Edvardsson |
| 7,525,476 | B1 * | 4/2009 | Delin .................. G01S 7/4056 |
| | | | 73/304 R |
| 7,821,444 | B2 | 10/2010 | Hall |
| 8,884,632 | B2 | 11/2014 | Klofer |
| 9,217,660 | B2 | 12/2015 | Zlotnick |
| 9,377,340 | B2 | 6/2016 | Hagg |
| 9,518,859 | B2 | 12/2016 | Bartov |
| 10,260,929 | B2 | 4/2019 | Kassubek |
| 10,788,351 | B2 | 9/2020 | Welle |
| 10,801,873 | B2 | 10/2020 | Westerling |
| 2005/0179584 | A1 | 8/2005 | Ohlsson |
| 2006/0201246 | A1 | 9/2006 | Rolfes |
| 2007/0028684 | A1 | 2/2007 | Benz |
| 2008/0272968 | A1 | 11/2008 | Muller |
| 2009/0007627 | A1 | 1/2009 | Perl |
| 2010/0090883 | A1 | 4/2010 | Chen |
| 2010/0101317 | A1 | 4/2010 | Ashrafzadeh |
| 2011/0193567 | A1 | 8/2011 | Klofer |
| 2011/0272866 | A1 | 11/2011 | Shameli |
| 2012/0281096 | A1 | 11/2012 | Gellaboina |
| 2014/0208845 | A1 | 7/2014 | Zlotnick |
| 2015/0007655 | A1 | 1/2015 | Skowaisa |
| 2015/0009063 | A1 | 1/2015 | Korsbo |
| 2015/0198474 | A1 | 7/2015 | Howard |
| 2017/0141453 | A1 | 5/2017 | Waelde |
| 2019/0316951 | A1 * | 10/2019 | McCormick ........ G01F 23/2845 |
| 2020/0158602 | A1 * | 5/2020 | Nunes Nogueira ...... C12G 3/02 |
| 2022/0252444 | A1 | 8/2022 | Kincaid |

OTHER PUBLICATIONS

Translation of CN-119086821-A (Year: 2024).*
U.S. Appl. No. 18/424,758, filed Jan. 27, 2024.
U.S. Appl. No. 18/800,279, filed Aug. 12, 2024.
U.S. Appl. No. 18/818,539, filed Aug. 28, 2024.
U.S. Appl. No. 19/013,859, filed Jan. 8, 2025.

* cited by examiner

1500

ENTRY

OBTAIN INITIAL ALCOHOL CONTENT AND FILL LEVEL — 1510

RECEIVE CURRENT FLUID LEVEL — 1520

OBTAIN ENVIRONMENTAL FACTORS — 1530

DETERMINE ALCOHOL CONTENT BASED ON FLUID LOSS — 1540

ADJUST ALCOHOL CONTENT BASED ON ENVIRONMENT FACTORS — 1550

STORE ADJUSTED ALCOHOL CONTENT — 1560

EXIT

ARTIFICIAL INTELLIGENCE DRIVEN MONITORING SYSTEM FOR AGING WHISKEY

CROSS-REFERENCE TO RELATED APPLICATION

This application is a Continuation-in-part of, and claims the benefit of U.S. application Ser. No. 19/013,859, titled "SYSTEM AND METHOD FOR DETERMINING FLUID LEVEL AND/OR ALCOHOL CONTENT UTILIZING EXTERNALLY MOUNTED CONTAINER MONITOR-ING SYSTEM" filed on Jan. 8, 2025, which is a Continu-ation-in part and claims of the benefit of U.S. application Ser. No. 18/800,279, titled "SYSTEM AND METHOD FOR DETERMINING ALCOHOL CONTENT WITHIN CON-TAINER UTILIZING CONTAINER MONITORING SYS-TEM," filed on Aug. 12, 2024, and U.S. application Ser. No. 18/818,539, titled "SYSTEM AND METHOD FOR DETERMINING ALCOHOL CONTENT UTILIZING CONTAINER MONITORING SYSTEM," filed on Aug. 28, 2024, both of which having claimed, as Continuation-in-part applications, the benefit and earlier filing date of U.S. application Ser. No. 18/424,758, titled "CONTAINER MONITORING SYSTEM AND METHOD THEREOF," filed on Jan. 27, 2024. This application incorporates by reference, herein, the entire contents of the above referred-to patents and applications.

BACKGROUND OF THE INVENTION

Conventional whiskey aging monitoring systems rely on manual sampling and external measurements to obtain vol-ume, proof, and color assessments of whiskey aging in barrels using periodic sampling and lab testing. However, obtaining whiskey aging data this way results in inaccurate measurements, oxidation risks, and inefficient regulatory compliance because of human error, invasive testing meth-ods, and the lack of real-time insights. Traditional whiskey aging lacks real-time analyzation insights-distilleries rely on manual sampling, historical intuition, and periodic lab test-ing to determine proof, color, and optimal aging time. This results in losses due to over-aging, under-aging, and incon-sistencies between barrels.

SUMMARY OF THE INVENTION

Aspects of this disclosure relate to an AI-driven, non-invasive system which can be configured to analyze whiskey color and maturation outcomes based on sensor-tracked environmental and chemical variables. In some aspects, this disclosure describes techniques that can integrate machine-learning, high-accuracy volume sensing, dielectric-based proof monitoring, and environmental data analysis to fore-cast how whiskey will age inside a barrel over time. By leveraging real-time barrel data such as time, proof, volume, temperature, humidity, and evaporation rates, the AI model can accurately analyze the final color, proof, and optimal aging duration for whiskey and other barrel-aged spirits. This can allow distilleries to reduce inconsistencies, improve yield management, and enhance quality control without relying on manual sampling or invasive testing.

These and other advantages of the invention will be further understood and appreciated by those skilled in the art by reference to the following written specification, claims and appended drawings.

BRIEF DESCRIPTION OF THE DRAWINGS

The advantages, nature, and various additional features of the invention will appear more fully upon consideration of the illustrative embodiments described in detail in connec-tion with the accompanying drawings, where like or similar reference numerals are used to identify like or similar elements throughout the drawings.

Figure 1:
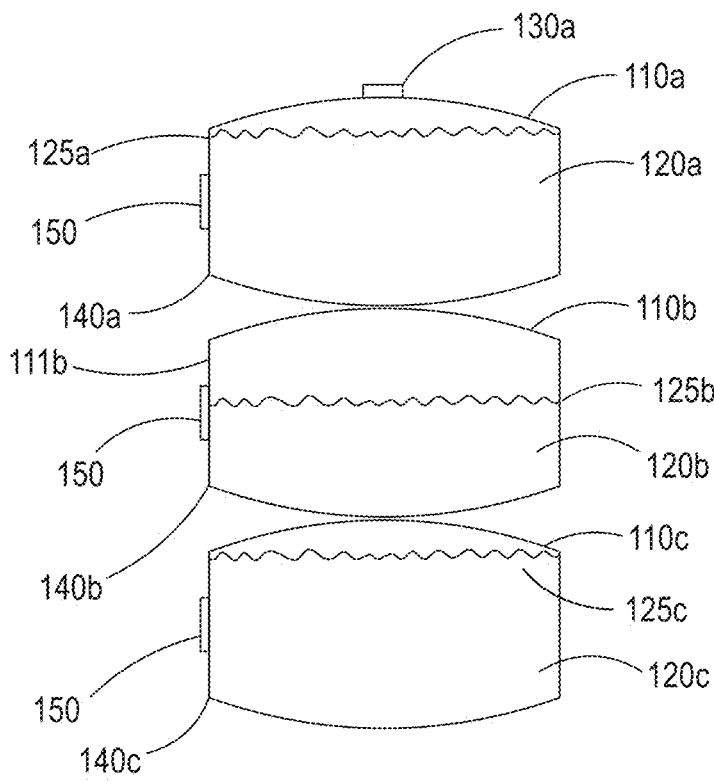
FIG. 1 illustrates a first conventional configuration for storing a plurality of barrels and the liquid contained therein.

It is to be understood that the figures, which are not drawn to scale, and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements are not provided herein. The disclosure, herein, is directed also to variations and modifications known to those skilled in the art.

DETAILED DESCRIPTION

Note that the specific embodiments given in the drawings and following description do not limit the disclosure. On the contrary, they provide the foundation for one of ordinary skill to discern the alternative forms, equivalents, and modifications that are contemplated by the inventors and encompassed in the claim scope.

Numerous alternative forms, equivalents, and modifications will become apparent to those skilled in the art once the above disclosure is fully appreciated. It is intended that the claims be interpreted to embrace all such alternative forms, equivalents, and modifications where applicable.

Disclosed herein are an apparatus and associated method implementations related to determining a liquid level within a barrel based on a system, located external to the barrel, configured to transmit a signal into the barrel and processing signals, reflected by the contained liquid, wherein the characteristics of the reflected signal (e.g. distance and time traveled) may be used to determine the presence of the liquid; determining a level of fluid within the barrel as a function of at least one of the distance and time traveled by the transmitted/reflected signal, determining a fluid level within the barrel and determining, as a function of at least the determined level of the fluid within the barrel and the physical dimensions of the barrel, the volume of fluid within the barrel.

Disclosed herein are an apparatus and associated method implementations located external to the barrel for determining an alcohol content within a barrel based on a system configured to transmit a signal (i.e., a measurement signal) into the barrel and processing signals, reflected by the contained liquid, wherein the characteristics of the reflected signal (e.g. signal strength, frequency, phase, distance and/or time traveled) may be used to determine the presence of the liquid and the alcohol content of the liquid, wherein determination of a level of fluid within the barrel may be used to determine which of a plurality of signals are transmitted into the barrel.

In one aspect of the invention, the system disclosed may comprise a modular device consisting of a motherboard, a specialized breakout board (chips), a data transmission module, a power source and at least one transmit and/or receiving antenna. The system may be attached to the face of an enclosed container (e.g., a whiskey barrel, wine barrel, beer barrel) with an antenna array that is suitable for transmitting signals in at least one of a Millimeter Wave (MM Wave) range, or a radio frequency range (i.e., Institute of Electronic and Electrical Engineers (IEEE) designated bands HF through W, and other wavelength ranges). In one aspect of the invention, the system and method disclosed any utilize a millimeter wave transmission system in a wavelength band of 57-64 GHz. In another aspect of the invention, a transmission system may operate in one or more of an ISM (Industrial, scientific, and medical) wavelength band that would avoid interference with other types of electronic equipment.

In one aspect of the invention, each of the at least one antenna may be configured to emit or transmit a signal at a same known wavelength within one or more of the referred to wavelength bands. In one aspect of the invention, each of the at least one antenna may be configured to transmit a signal at a different known frequency (or wavelength) within one or more of the referred to wavelength bands. In one aspect of the invention, each of the at least one antenna may be configured to transmit at least one signal at one or more frequencies within one or more different known frequency or wavelength bands.

In one aspect of the invention, one or more characteristics (e.g., signal strength, frequency, phase, distance and/or time traveled) of the signals reflected by the contained fluid or liquid, may be used to determine a level of the contained fluid based at least on a position of one or more of the antennas receiving the reflected signals and subsequently the alcohol content of the liquid within the barrel.

In one aspect of the invention, the signal strength of the signals reflected by the contained fluid or liquid, may be used to determine the level of the contained fluid based at least on a position of one or more of the antennas receiving the reflected signals.

In one aspect of the invention, measurements regarding the signal strength and determined fluid level (and volume) may be relayed to a communications hub via one or more transmissions protocols and exported wirelessly (cellular, Wi-Fi) or over a wired Internet connection to a common database wherein reports may be derived. In another aspect of the invention, measurements regarding signal strength and determined fluid level (and/or volume) may be relayed by a near-field communication transmission (e.g., RFID, BLUETOOTH, etc.) that enable periodic monitoring of the determined fluid level and/or volume.

In one aspect of the invention, consultative data analysis reports may be created to assist a manufacturer/consumer with making actionable business decisions based upon results.

In accordance with the principles of the invention, the system and method disclosed may utilize a Millimeter wave transmission system (30 GHz-300 GHz) and an appropriately scaled (frequency selective) antennas to determine a level of the liquid inside of an enclosed container (e.g., a whiskey barrel).

In one aspect of the invention, by measuring the liquid level over time, a manufacturer/consumer may determine fluid internal volume at any given period. In accordance with the principles of the invention, while barrel technology is referred to, it would be understood by those skilled in the art that the system and method disclosed may be utilized to determine the fluid level in any enclosed system used containing liquid.

In one aspect of the invention, a method is disclosed for determination of an alcohol content of a liquid within an enclosed barrel wherein the alcohol content is based on an initial alcohol content and one or more environmental factors, such as location, temperature, environment conditions, etc.

In one aspect of the invention, a method is disclosed for the determination of an alcohol content of a contained fluid based on a determination of evaporation and/or absorption of the fluid and an extrapolation from a known initial level.

In one aspect of the invention, a method is disclosed wherein a determination of a loss of fluid within an enclosed container is utilized to determine an alcohol content of the fluid considering one or more environmental factors.

In accordance with the principles of the invention, while barrel technology is referred to, it would be understood by those skilled in the art that the system and method disclosed may be utilized to determine the fluid level in any enclosed system containing liquid.

In one aspect of the invention, a method is disclosed for the determination of an alcohol content of a contained fluid based on an evaluation of at least one variation in at least one characteristic (e.g., signal strength change, frequency shift, phase shift, change in distance and/or time traveled, etc.) of at least one reflection of a signal transmitted in at least one frequency or wavelength band.

Each of the foregoing implementations can be employed individually or in conjunction.

FIG. 1 illustrates a first conventional configuration for storing a plurality of barrels and the liquid contained therein.

Conventionally barrels 110a, 110b, 110c, may be filled with a liquid 120a, 120b, 120c, respectively, and stacked horizontally in racks (not shown). The implementation depicted by FIG. 1 shows the exemplary respective liquid levels 125a, 125b, 125c of liquids 120a, 120b, 120c. Access to barrels 110a, 110b, 110c, is conventional through a bung 130 individually configured in each barrel 110 (of which only bung 130a associated with barrel 110a is shown). In the depicted example, the bung 130a is positioned on a side surface of the corresponding barrel 110a. Although only bung 130a associated with barrel 110a is shown, it would be recognized that bung 130 (bung 130a, bung 130b, bung 130c) is associated with each of the illustrated barrels 110a, 110b, 110c.

Generally, the bung 130 (e.g., 130a, 130b, 130c) enables a tester (not shown) to access the liquid 120a, 120b, 120c in a corresponding one of barrels 110a, 110b, 110c. As previously discussed, the conventional manner of testing is to insert an object (e.g., a pipette,) into the bung 130 (and/or bung hole), wherein liquid is collected in the pipette and removed from barrel 110. The liquid may then be tested to determine quality and the level of the liquid within the barrel using a graduated scale on the pipette.

However, as discussed above, the opening of the bung 130 to insert the pipette into the container 110 to test the contained liquid 120 introduces air and, possibly, other contaminants into the contained liquid. The introduced air may alter the quality of the contained liquid.

Accordingly, container monitoring system 150, disclosed herein, resolves the issues that are known to occur with the conventional means for testing the liquid level within the container. Container monitoring system 150 provides a non-invasive method for determining a level of a contained liquid 120a within barrel 110a, through its inclusion or introduction onto a surface of face 140 of each of the illustrated containers or barrels 110a.

Although face surface 140a associated with barrel 110a is shown, it would be recognized that monitoring system 150 may be applied to the surface of face 140 of barrels 110b, 110c to provide a non-invasive method for determining a level of a contained liquid (120b, 120c) within barrels 110b, 110c, respectively.

Figure 2:
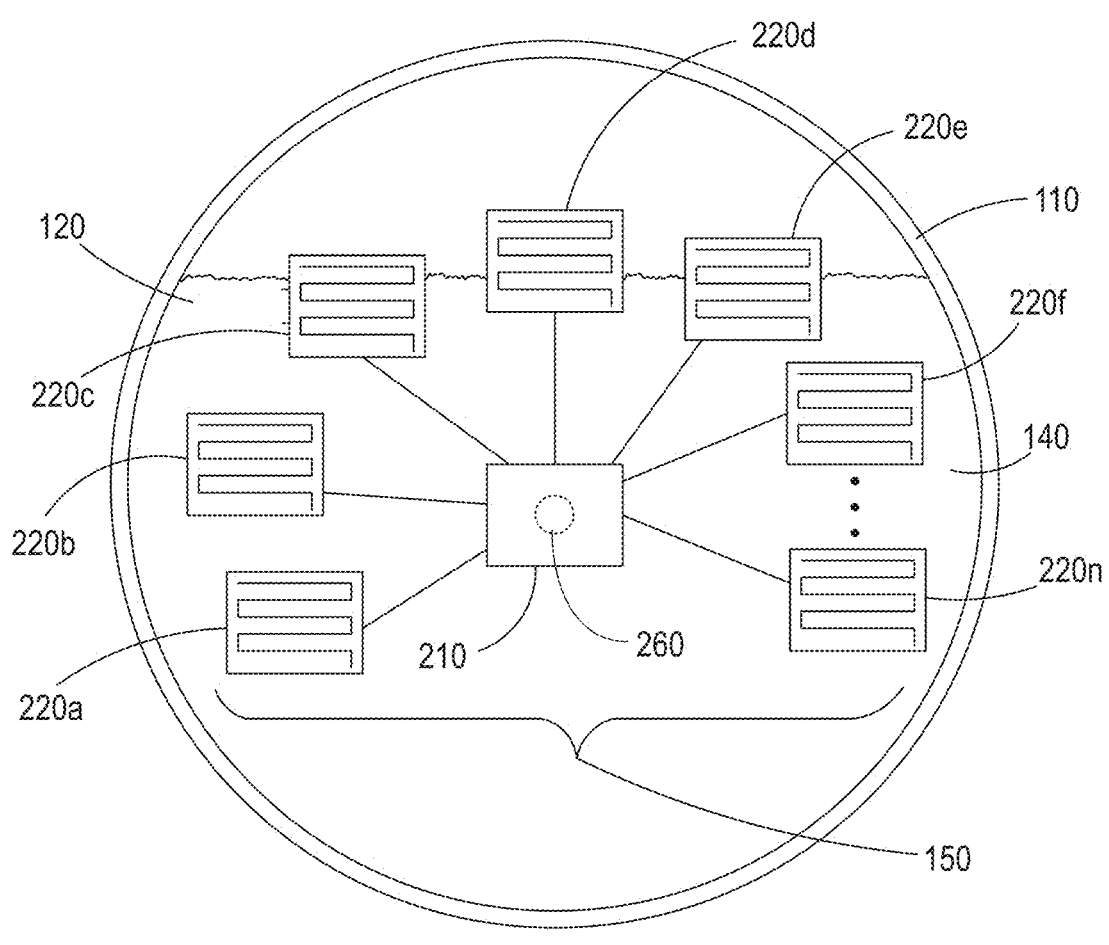
FIG. 2 illustrates a first exemplary embodiment of a system for determining liquid content within a barrel in accordance with the principles of the invention.

FIG. 2 illustrates a first exemplary embodiment of a monitoring system 150 in accordance with the principles of the invention.

In accordance with the principles of the invention, monitoring system 150 comprising processing system 210 and a plurality of antennas 220 (220a, 220b, 220c . . . 220n) which are positioned on a surface of face 140 of a corresponding container or barrel 110.

In accordance with the illustrated aspect of the invention, monitoring system 150 is arranged circumferentially (a "wagon wheel" configuration) about the surface of face 140 of barrel 110, wherein processing system 210 is at a center (or hub) of the plurality of illustrated antennas 220a, 220b, . . . 220n.

In accordance with this aspect of the invention, the position of each of the illustrated antennas 220a, 220b . . . 220n with respect to a center position 260 of the surface of face 140 is known and in a symmetrical relationship. For example, in this illustrated aspect, antennas 220a, 220b . . . 220n may be positioned on face 140 in a conventional "clock" formation. That is, antenna 220d is illustrated as being positioned in a 12 o'clock position with respect to center 260, antenna 220e is illustrated as being positioned at a 1 o'clock position with respect to center 260. Antenna 220f is illustrated as being positioned at a 2 o'clock position with respect to center 260 and antenna 220n may be positioned at a 4 o'clock position with respect to center 260. Similarly, antennas 220c, 220b and 220a may be positioned at 11 o'clock, 10 o'clock and 8 o'clock positions, respectively, with respect to center 260. In accordance with the principles of the invention, the positioning of the illustrated antennas establishes a relationship between a reference point (i.e., center point 260) and each of the antennas that may be used to determine a level of fluid (e.g., level of liquid 120) within container 110.

In another aspect of the invention, the plurality of illustrated antennas may be arranged in a physically, (i.e., non-systematical) relation, wherein antennas 220d, 220c, 220f, and 220n may be positioned as discussed above (12, 1, 2, 4 o'clock, respectively) and antennas 220c, 220b and 220a may be positioned at 11:30 o'clock, 10:30 o'clock and 8:30 o'clock positions, respectively with respect to center 260. In accordance with the principles of the invention, the positioning of the antennas 220a . . . 220n in this manner provides for a refined determination of the level of fluid (e.g., level of liquid 120) within container 110, as will be discussed.

In one aspect of the invention, processing system 210 provides signals to a corresponding one of the antenna 220a, . . . 220n, which operates as a transmitting antenna to transmit the signals through face 140 toward liquid 120 contained within barrel 110. The corresponding antenna 220a . . . 220n, may then operate as a receiving antenna to receive a reflection of the transmitted signal, which is caused by the interaction of the transmitted signal with the contained liquid 120.

In one aspect of the invention, antennas 220a, 220b, . . . 220n may be omni-direction antennas that emit (or transmit) signals over a wide field of view (e.g., toward and away from face 140). In another aspect of the invention, antennas 220a, 220b . . . 220n may be directional antennas that emit (or transmit) signals in a very limited field of view (e.g., toward face 140). In still another aspect of the invention antennas 220a, 220b . . . 220n may be highly directional antennas with narrow beams widths that emit (or transmit) signals in a limited and narrow field of view (e.g., toward face 140 with 1-degree beamwidth).

In one aspect of the invention, antennas 220a, 220b . . . 220n may each be configured as transmitting and receiving antenna, wherein original signals provided by processing system 210 are transmitted by antennas 220a . . . 220n and reflection signals, captured by antennas 220a . . . 220n), are provided to processing system 210. In another aspect of the invention, selected ones of the illustrated antennas 220a, 220b . . . 220n may operate as transmitting antennas to transmit signals into container 110 and selected other ones of the illustrated antennas 220a, 220b . . . 220n may operate as receiving antenna to capture reflections of the transmitted signals. The antennas designated as transmitting antennas receive signals from processing system 210 and receiving antenna provide signals to processing system 210.

In addition, antennas designated as transmitting antennas may comprise omni-directional or highly directional antenna and antennas designated as receiving antennas may be narrow beam width directional antennas.

In one aspect of the invention, a single antenna may be designated as a transmitting antenna (e.g., 220d) and the remaining of the illustrated antennas (220a, 220b, 220c, 220e . . . 220n) may be designated as receiving antenna. In this case, a single "ping" from the one transmitting antenna may be detected by a plurality of receiving antennas and the results of the detected reflections may be utilized to determine a level of fluid contained. In still another aspect of the invention, the single transmitting antenna may periodically transmit a "ping" and each of the designated receiving antenna may be selectively "turned-on" to enable the "turned-on" receiving antenna to receive a reflection of the transmitted signal.

Although, monitoring system 150 is shown with processing system 210 as a central hub, it would be recognized by those skilled in the art that processing system 210 may be placed at any position on face 140 without altering the scope of the invention claimed.

Figure 3:
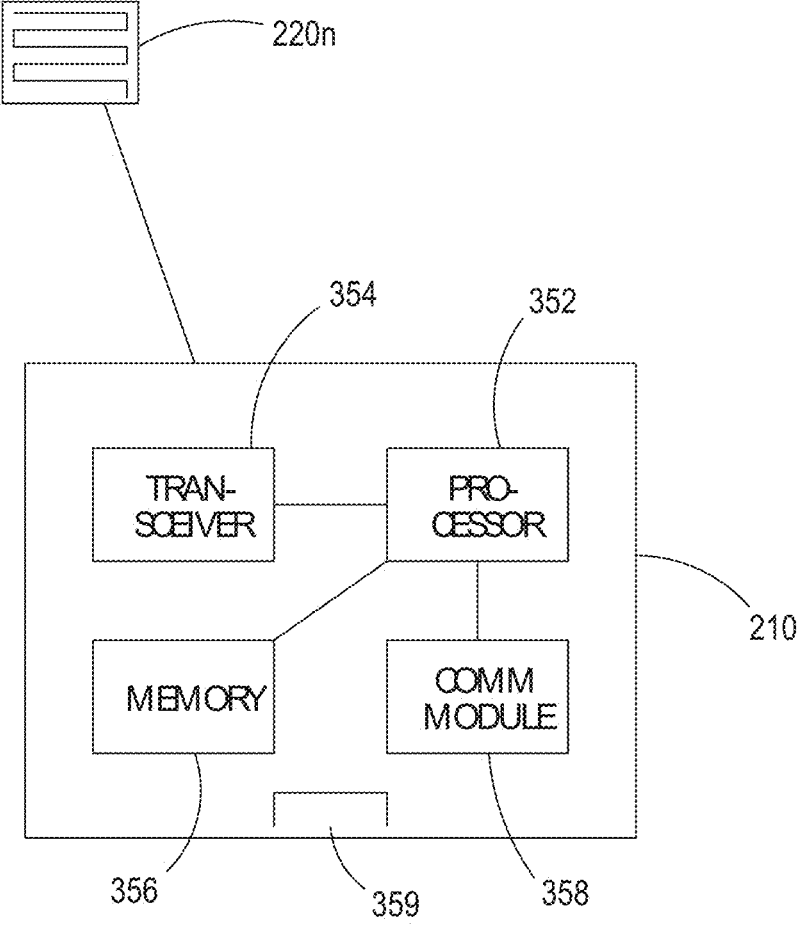
FIG. 3 illustrates a block diagram of an exemplary embodiment of a processing system for determining liquid content within a barrel in accordance with the principles of the invention.

FIG. 3 illustrates a block diagram of an exemplary embodiment of a processing system for determining liquid content within a barrel in accordance with the principles of the invention.

In accordance with the principles of the invention, processing system 210 comprises a transceiving (transmitter/receiver) system 354 that is in communication with antennas 220a . . . 220n (of which only antenna 220n is shown in FIG. 3). Transceiving system 354 may include one or more switching networks (not shown) that provide signals to selectively provide signals to a corresponding one of the plurality of antennas 220a, 220b, 220c . . . 220n. For example, transceiving system 354 may provide through a (not shown) switching network, signals to each of the plurality of antennas shown in FIG. 2, for example, in a sequential manner such that only one antenna is transmitting and/or receiving at any given time. Alternatively, the (not shown) switching network(s) may cause more than one antenna to concurrently transmit signals and/or receive reflection signals. Alternatively, the (not shown) switching network may cause at least one of the antennas to operate as a transmitting antenna while causing at least one of the plurality of antenna to operate as a receiving antenna.

Although element 354 is referred to as a transceiving system, it would be recognized that transceiving system 354 may comprise separate receiving and transmitting system without altering the scope of the invention claimed.

Processor 352 may comprise one or more conventional processing systems (e.g., INTEL Pentium serial processors) that operates to access instructions and provides control instruction to processing system 210. PENTIUM is a registered trademark of INTEL Corporation, a Delaware, USA corporation. Alternatively, processor 352 may comprise dedicated hardware and software that may provide control instruction to processing system 210.

Memory 356 provides storage capability for instructions (software, code) that may be accessed by processor 352 to control the processing of processing system 210. Memory 356 may, for example, be represented as semiconductor memory, such as a combination of PROM (programmable read-only memory), wherein instructions are permanently stored, or RAM (random access memory), wherein data values may be accessed and overwritten.

Communication module (i.e., transmitter/receiver) 358 represents a means to provide data collected by processor 352 to one or more external devices (not shown), which may be used to evaluate, correlate and collate the data collected. Communication module 358 may comprise a wired or a wireless communication connection to the not shown external devices. For example, communication module 358 may be in wired communication with one or more systems that may be in communication with the Internet that allows for the monitoring of the determined fluid level over a broad geographical area.

Alternatively, communication module 358 may include elements that provide information through one or more wireless communication protocols (e.g., a very short-range NFC protocol (e.g., RFID), a short-range protocol (BLUETOOTH), a longer-range protocol (Wi-Fi) and a long-range protocol (e.g., cellular)). In addition, communication module 358 may operate to receive information from an external source either through a wired communication protocol or a wireless communication protocol. Such information may, for example, comprise instructions (code) that may be stored in memory 356, information regarding the tank (e.g., volume, dimensions, a type of material comprising the tank, etc.) to which monitoring system 150 is attached, and the content of the tank. This information may include information for the reprogramming, or the pairing, of monitoring system 150 with the specific tank (or barrel) 110. In one aspect of the invention, monitoring system 150 may be "paired" with a specific barrel, such that monitoring system 150 may monitor the contents of the paired barrel 110 over multiple uses of the barrel. For example, an identification number of the container (or barrel) to which monitoring system 150 is attached, may be inputted into memory 356. Alternatively, barrel 110 may include an electronic identification code that may be inputted via a wireless communication connection into monitoring system 150 (i.e., paired) using a short-range identification communication protocol (e.g., RFID).

Power source 359 provides power (electrical energy) to the electrical/electronic components of processing system 210. In one aspect of the invention power source 359 may represent a lithium-nickel battery that provides power to processing system 210 for an extended period of time. In another aspect of the invention, power source 359 may be a rechargeable battery element that may be recharged by removal from processing system 210 or recharged while included within processing system 210. Alternatively, power source 359 may be an AC to DC converter that receives electrical energy from a main source of power (e.g., 120-volt outlet) and converts the received power to a direct current that is used to power the electrical/electronic components of processing system 210.

Figure 4:
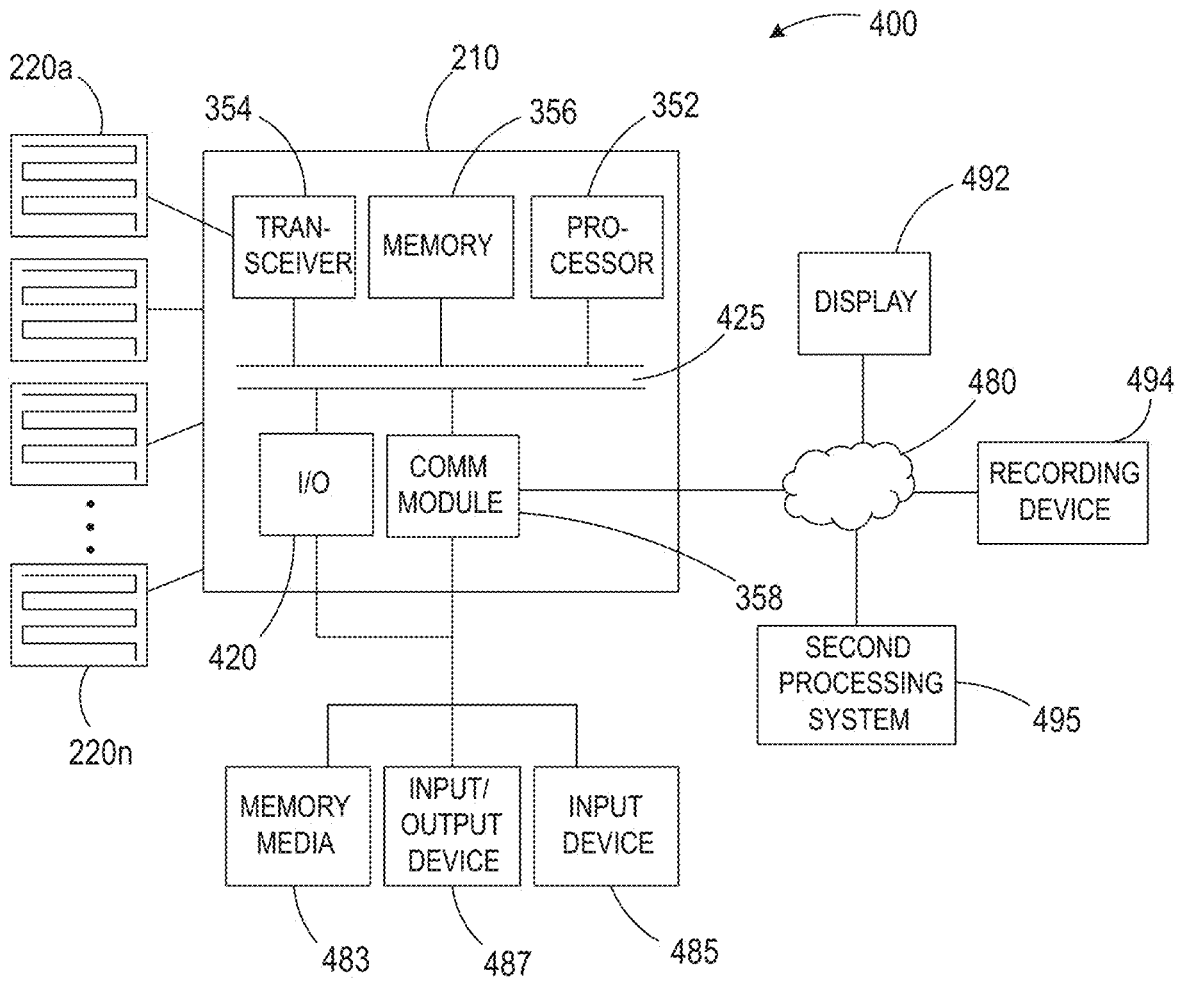
FIG. 4 illustrates a block diagram of an exemplary system for determining liquid content within a barrel in accordance with the principles of the invention.

FIG. 4 illustrates a block diagram of an exemplary system for determining liquid content within a barrel in accordance with the principles of the invention.

In this exemplary system embodiment 400, input data is received from antennas (sources) 220a . . . 220n and processed in accordance with one or more programs, either software or firmware, executed by processing system 210. The results of processing system 210 may then be transmitted over network 480 for viewing on display 492, reporting device 494 and/or a second processing system 495.

In the depicted implementation processing system 210 includes one or more receiving devices 354 that receive data from the illustrated antennas, devices, or sources 220a . . . 220n. The received data is then applied to processor 352, which is in communication with input/output device 420 and memory 356. Transmitting/receiving element 354, processor 352 and memory 356 may communicate over a communication medium 425, which may represent a communication network, e.g., ISA, PCI, PCMCIA bus, one or more internal connections of a circuit, circuit card or other device, as well as portions and combinations of these and other communication media.

Processor 352 may be a general processor central processing unit (CPU) or a special purpose processing unit or dedicated hardware/software, such as a PAL, ASIC, FGPA, each of which is operable to execute computer instruction code or a combination of code and logical operations. In one embodiment, processor 352 may include, or access, software or code that, when executed by processor 352, performs the operations illustrated herein. As would be understood by those skilled in the art when a general-purpose computer (e.g., a CPU) loaded with or accesses software or code to implement the processing shown herein, the execution of the code transforms the general-purpose computer into a special purpose computer. The code may be contained in memory 356 or may be read or downloaded from one or more external devices.

For example, code or software may be downloaded from a memory medium, such as a solid-state memory or similar memory devices 483, or may be provided by a manual input device 485, such as a keyboard or a keypad entry, or may be read from a magnetic or optical medium (not shown) or via downloaded from a second I/O device 487 when needed. Information items provided by external devices 483, 485, 487 may be accessible to processor 352 through input/output device 420, as shown. Further, the data received by input/output device 420 may be immediately accessible by processor 352 or may be stored in memory 356. Processor 352 may further provide the results of the processing to one or more external devices (i.e., display 492, recording device 494 or a second processing unit 495).

As one skilled in the art would recognize, the terms processor, processing system, computer or computer system may represent one or more processing units in communication with one or more memory units and other devices, e.g., peripherals, connected electronically to and communicating with the at least one processing unit. Furthermore, the devices illustrated may be electronically connected to the one or more processing units via internal busses, e.g., serial, parallel, ISA bus, Micro Channel bus, PCI bus, PCMCIA bus, USB, etc., or one or more internal connections of a circuit, circuit card or other device, as well as portions and combinations of these and other communication media, or an external network, e.g., the Internet and Intranet. In other embodiments, hardware circuitry may be used in place of, or in combination with, software instructions to implement the invention. For example, the elements illustrated herein may also be implemented as discrete hardware elements or may be integrated into a single unit (e.g., ASIC).

As would be understood, the operations illustrated may be performed sequentially or in parallel using different processors to determine specific values. Processing system 210 may also be in two-way communication with each of the sources 220a . . . 220n. Processing system 210 may further receive or transmit data over one or more network connections 480 from a server or servers over, e.g., a global computer communications network such as the Internet, Intranet, a wide area network (WAN), a metropolitan area network (MAN), a local area network (LAN), a terrestrial broadcast system, a cable network, a satellite network (cellular), and a wireless network (Wi-Fi), as well as portions or combinations of these and other types of networks. As will be appreciated, network 480 may also be internal networks or one or more internal connections of a circuit, circuit card or other device, as well as portions and combinations of these and other communication media or an external network, e.g., the Internet and Intranet.

In one aspect of the invention, external devices 483, 485, 487, 492, 494, 495 may be representative of a handheld calculator, a special purpose or general-purpose processing system, a desktop computer, a laptop computer, tablet computer, or personal digital assistant (PDA) device, etc., as well as portions or combinations of these and other devices that can perform the operations illustrated.

Figure 5A:
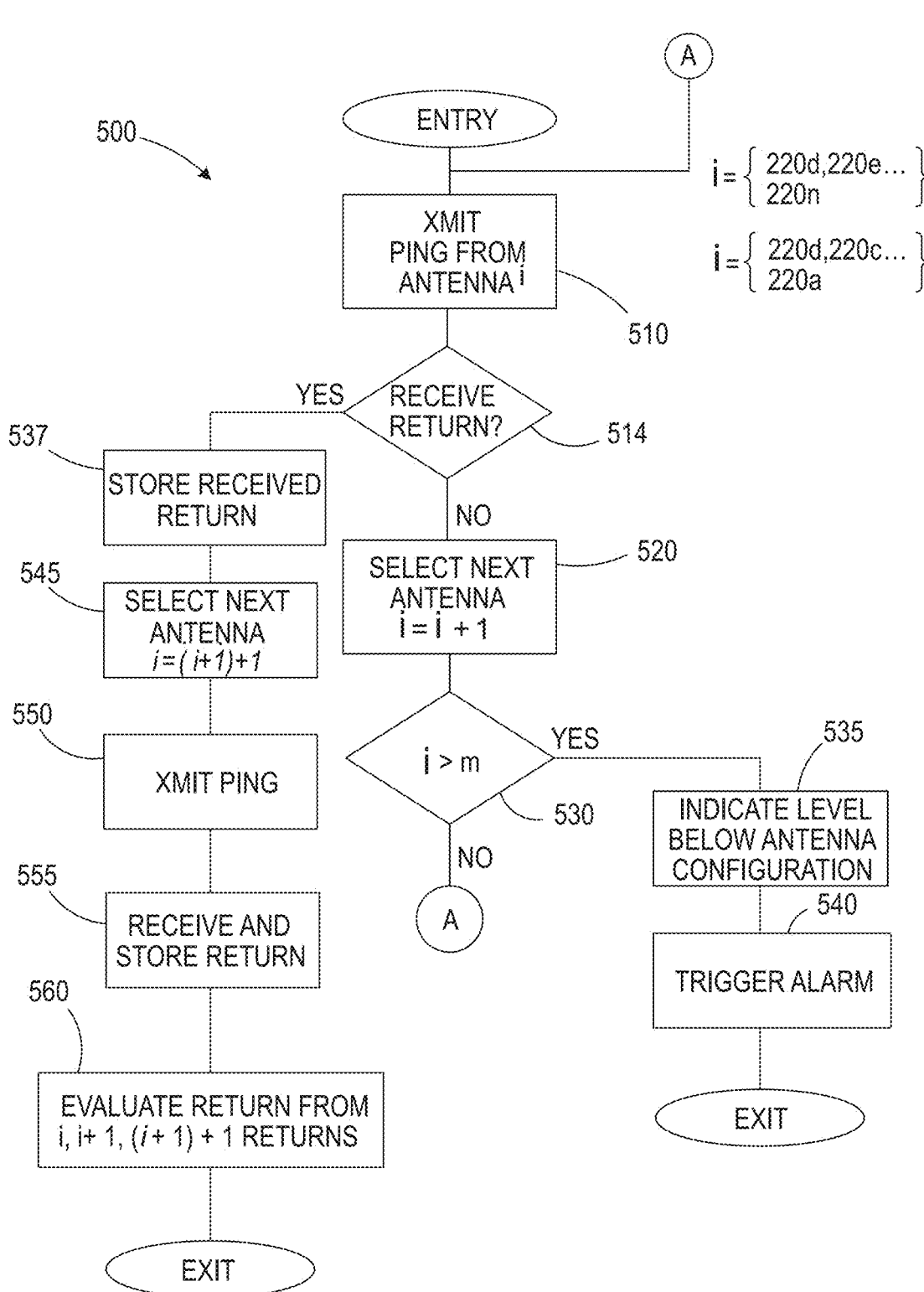
FIG. 5A illustrates a flowchart of an exemplary process-ing in accordance with the principles of the invention.

FIG. 5A illustrates a flowchart of an exemplary processing in accordance with the principles of the invention.

In this illustrated exemplary processing 500, the processing system 210 (described with reference to at least FIGS. 2-4) initiates transmission of a signal (referred to, hereinafter as "ping") to a selected one ("i") of the antenna 220a . . . 220n. In one aspect of the invention, the initially selected antenna may be selected as the top-most antenna (i.e., 220d, FIG. 2) as the container may be considered in an initially "full state."

In accordance with the illustrated embodiment shown in FIG. 2, processing may operate from the highest antenna 220d positioned on face 140 to the lowest antenna positioned on face 140 (220a or 220n). In one aspect of the invention, processing may select to operate with antennas selected from a first set of antennas (i.e., 220d, 220c . . . 220n-clockwise selection). Alternatively, processing may select to operate with antennas selected from a second set of antennas (i.e., 220d, 220c . . . 220a-counterclockwise selection). In still another alternative aspect of the invention, processing may select to operate using the first set of antennas and then the second set of antennas, wherein the first and second sets of antennas may be a symmetric or a non-symmetric relation with respect to a known point (e.g., center point 260). Although examples of the selection of the one or more antenna selected to be within the set of antenna are disclosed, it would be recognized that other methods of selection of antennas within the set of antenna may be implemented without altering the scope of the invention claimed.

Processing then selects, at step 510, an initial antenna selection, referred to as "i" from which a signal or a ping is to be transmitted. At step 514, processing waits for return or reflection of the transmitted ping.

Upon not receiving a return (or reflected) signal (after a known period of time, as discussed in FIG. 5B), processing continues to step 520, where a next ("i+1") antenna is selected from the selected clockwise or counterclockwise set of antennas. Processing then proceeds to step 530 where a check of the value (within the selected set) of the selected antenna is greater than the number of antenna (m) within the selected set of antenna. If the value of the selected antenna is greater than the number antenna within the set, then processing proceeds to step 535, wherein the returns (i.e., reflections of transmitted pings) from each of the antenna within the selected set of antenna is evaluated.

At step 535, the processing system 210 performs a test to determine if any return has been received from any antenna in the selected set. Upon determining no returns have been received from any of the antennas in the selected set, the processing system 210 sets an indication that no returns have been received from any of the antennas in the selected set and, hence, the liquid level is flagged as being "Too Low." At step 540, the processing system 210 triggers an alarm indication to indicate the "Too Low" condition.

Returning to step 530, if the value (within the selected set) of the next selected antenna is not greater than the number of antennas within the selected set, processing proceeds to step 510 to transmit (i.e., Xmit) a ping from the selected (next) antenna.

Returning to step 514, when a return is detected, processing proceeds to step 537 where the received return is stored. At step 545, a next antenna is selected ((i+1)+1), wherein processing proceeds to step 550 to transmit a ping from the selected (next) antenna. At step 555, a return from the transmitted "ping" is received and subsequently stored.

At step 560, the returns from the i, i+1 and (i+1)+1 antenna selected are evaluated to determine a level of the contained liquid.

As the antenna selection is made from highest to lowest antenna placement on face 140 (in this illustrative processing) after two sequential returns are received, processing is halted as each of the antennas lower in position to the (I+1)+1 antenna would be in contact with the contained liquid and, thus, information from these lower antennas do not contribute any additional information to the level of the contained liquid. This limitation of the number of antennas transmitting is advantageous as it reduces the power requirements needed in obtaining a level of the contained fluid.

Although FIG. 5A refers to processing for selecting one antenna in one of a clockwise set and a counterclockwise set of antennas, it would be understood that the processing shown in FIG. 5A may be adaptable to select first one set of antennas (e.g., clockwise) and then select the other set of antennas (e.g., counterclockwise) to determine the level of the contained liquid.

In one aspect of the invention, wherein the position of the antennas within one set (e.g., clockwise) of antenna on face 140 may be spatially offset from a position of the antenna in the second set (e.g., counterclockwise) of antenna on face 140 (i.e., non-symmetrical relation), the use of information from both the first and second sets of antenna provides for a more precise determination of the liquid within container 110.

Figure 5B:
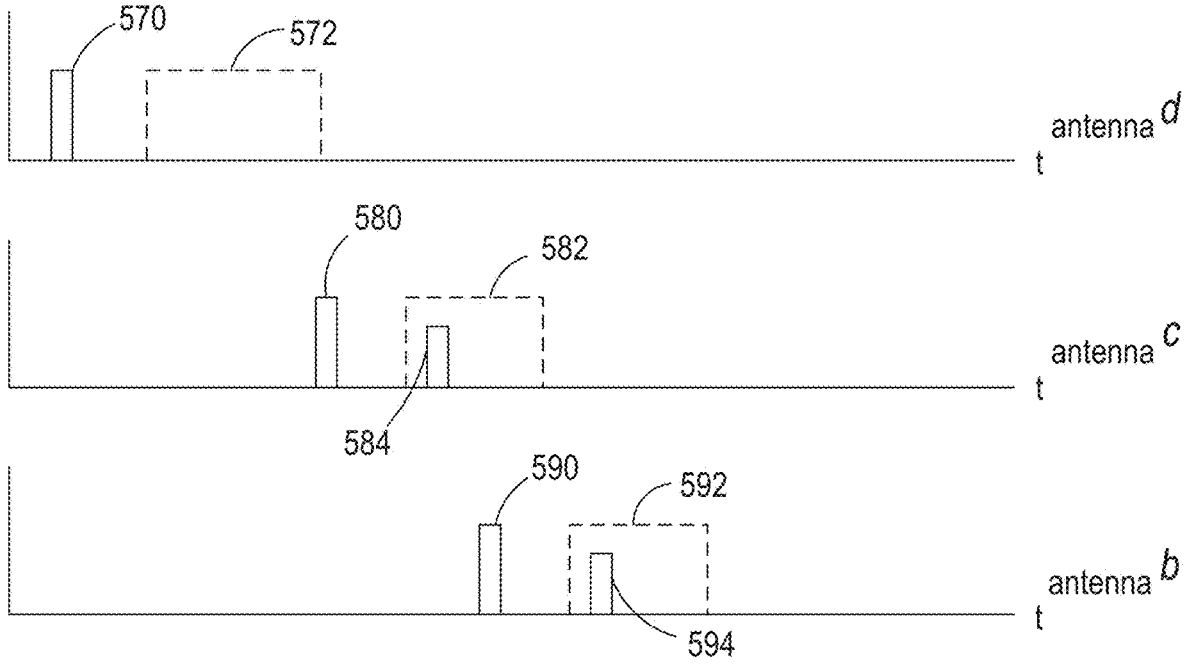
FIG. 5B illustrates an exemplary timing chart in accor-dance with the principles of the invention.

FIG. 5B illustrates an exemplary timing chart in accordance with the principles of the invention.

In this illustrated example, which corresponds to the processing shown in FIG. 5A, an initial ping or transmission 570 is made from antenna 220*d* (the highest antenna illustrated in FIG. 2). A return window 572 is opened. The time period the return window 572 remains open is based on the expected time of the detection of a return.

In this illustrated example, a return is not detected within the expected time, which is flagged as a return, but a NO response. Processing proceeds to select a next antenna (e.g., antenna 220*c*), wherein a ping or transmission 580 is transmitted and a return window 582 is opened. In this illustrated example, return 584 is detected and window 582 is closed. A next antenna (e.g., antenna 220*b*) is selected from which ping 590 is transmitted and return window 592 is opened.

As illustrated, return 594 is detected and, thus, window 594 is closed.

Figure 6:
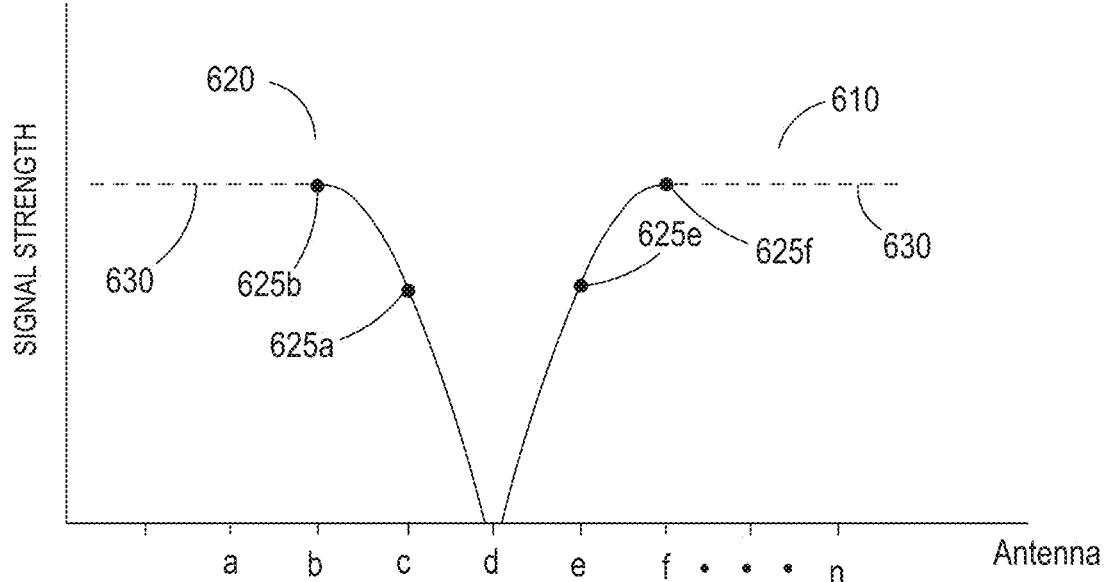
FIG. 6 illustrates a graph of an exemplary signal return chart for determined liquid content within a barrel in accor-dance with the principles of the invention.

FIG. 6 illustrates a graph of an exemplary signal return chart 600 for determining liquid content within a barrel in accordance with the principles of the invention.

In this illustrated example, which is related to the timing diagram shown in FIG. 5B, the transmission of a ping from antenna 220*d* produces no return and, hence, no signal is shown for antenna 220*d* in FIG. 6. However, with the selection of antenna 220*e* and 220*f*, returns 625*e* and 625*f* detected by antenna 220 and 220*f*, respectively are shown on graph segment 610.

With the detection of return 625*e* and, a second (confirmation) return 625*f*, processing may be halted and a level of contained liquid may be determined.

Further illustrated are returns 625*c* and 625*b*, associated with antenna 220*c* and 220*b*, (see FIG. 2), respectively on graph segment 620.

In accordance with one aspect of the invention, returns 625*b*, 625*c*, 625*e* and 625*f* may be evaluated (e.g., signal strength) to determine a level of the contained fluid.

In accordance with another aspect of the invention, the position of antennas 220*b*, 220*c* may be spatially offset (i.e., physically displaced) from antennas 220*e*, 220*f* and, thus, the evaluation of the received returns may determine the level of the contained liquid more precisely, as previously discussed.

Figure 7A:
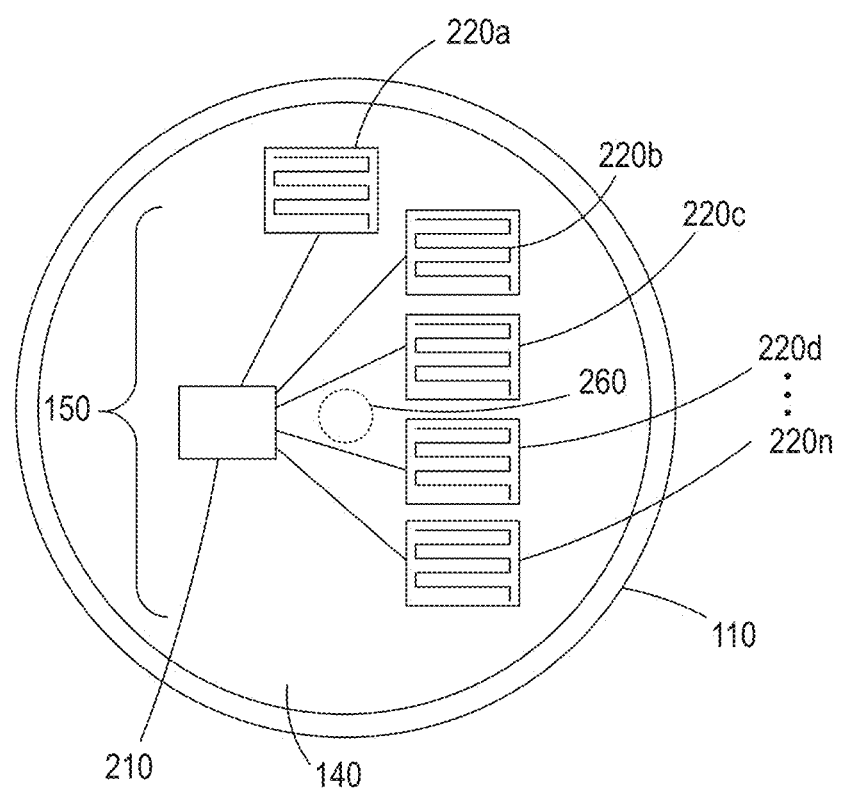
FIGS. 7A and 7B illustrate a first and second aspect of a second exemplary embodiment of a system for determining liquid content within a barrel in accordance with the prin-ciples of the invention.

FIG. 7A illustrates a first aspect of a second exemplary embodiment of a system for determining liquid content within a barrel in accordance with the principles of the invention.

In this illustrated configuration, antenna 220*a*, 220*b*. 220*n* are arranged linearly on face 140 of barrel 110.

In this illustrated configuration, antenna 220*a*, 220*b*, 220*c*, . . . 220*n* are shown in a linear arrangement, wherein processing similar to that shown in FIGS. 5A, 5B and 6 may be performed.

Figure 7B:
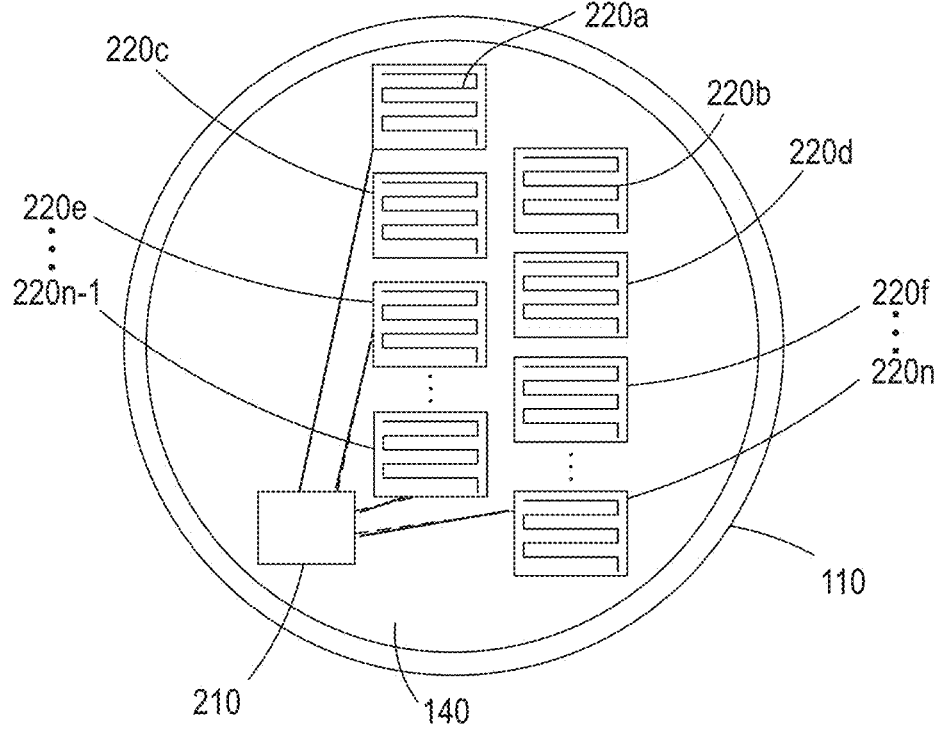

FIG. 7B illustrates a second aspect of a second exemplary embodiment of a system for determining liquid content within a container (or barrel) in accordance with the principles of the invention.

In this illustrated configuration, antenna 220*a*, 220*c* . . . 220*n*-1 may be arranged in a first set and antenna 220*b*, 220*d* . . . 220*n* may be arranged in a second set of antennas that is spatially offset from the first set of antennas. As discussed with regard to FIG. 2, the positioning of the illustrated plurality of antenna in a physically non-symmetrical relation allows for a more precise determination of a level of fluid within barrel 110. In the implementation depicted by FIG. 7A the processing system 210 is disposed at a known offset distance from the center point 260 of the face 140 of the barrel 110. The implementation depicted by FIG. 7B includes but does not show the barrel 110 face 140 center point 260 that is not visible behind the depicted antenna 220c.

Accordingly, a determination of the level of a contained liquid may be made based on the receiving of reflections of transmitted pings or signals as previously discussed.

Figure 8:
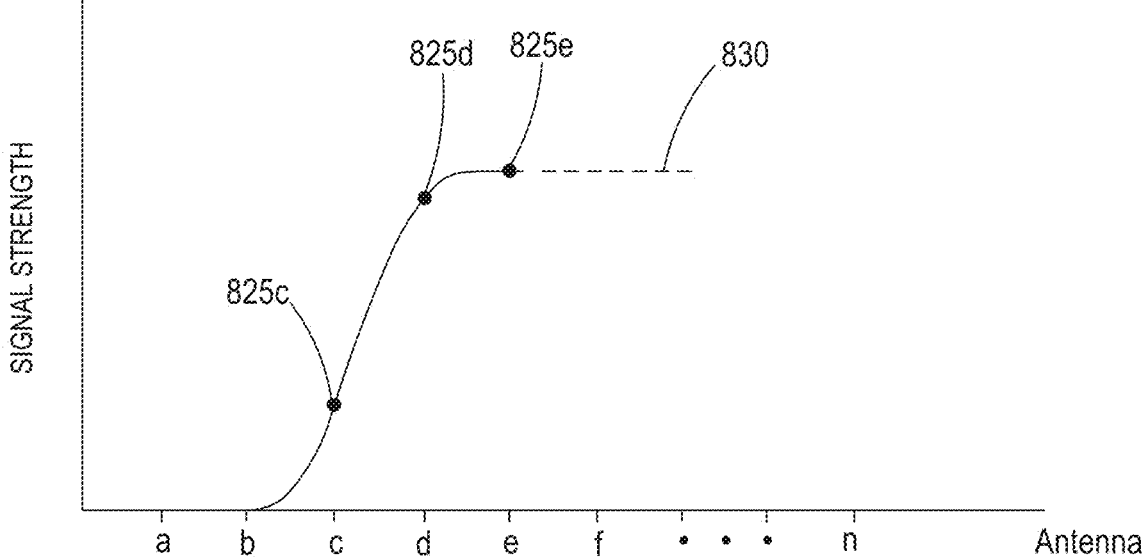
FIG. 8 illustrates a graph of an exemplary signal return chart associated with the configurations shown in FIGS. 7A and 7B for determined liquid content within a barrel in accordance with the principles of the invention.

FIG. 8 illustrates a graph of an exemplary signal return chart 800 associated with the configurations shown in FIGS. 7A and 7B in accordance with the principles of the invention.

In accordance with this aspect of the invention, signals transmitted by antenna 220a, 220b (two physically highest antenna, FIGS. 7A and 7B) fail to provide a response within an expected time window (FIG. 5B) and, thus, a first return 825c is received from the transmission of a ping from antenna 220c with a subsequent return 825d received from the transmission of a ping from antenna 220d as shown on graph segment 830. As discussed previously, processing may be halted after two consecutive returns are received.

In accordance with one aspect of the invention, when the returned signal level differ by a known amount, a next transmission and return 825e may be executed to validate a previous return (e.g., 825d)

In this illustrative example, a level of the content liquid in barrel 110 may be determined as lying between the position of antenna 220b and 220c, based on the strength of return signals depicted by FIG. 8. Hence, with the knowledge of the position of each of the antenna with respect to center point 260 (FIG. 2), the level of liquid 120, and the volume content within barrel 110 may be accurately determined.

Figure 9:
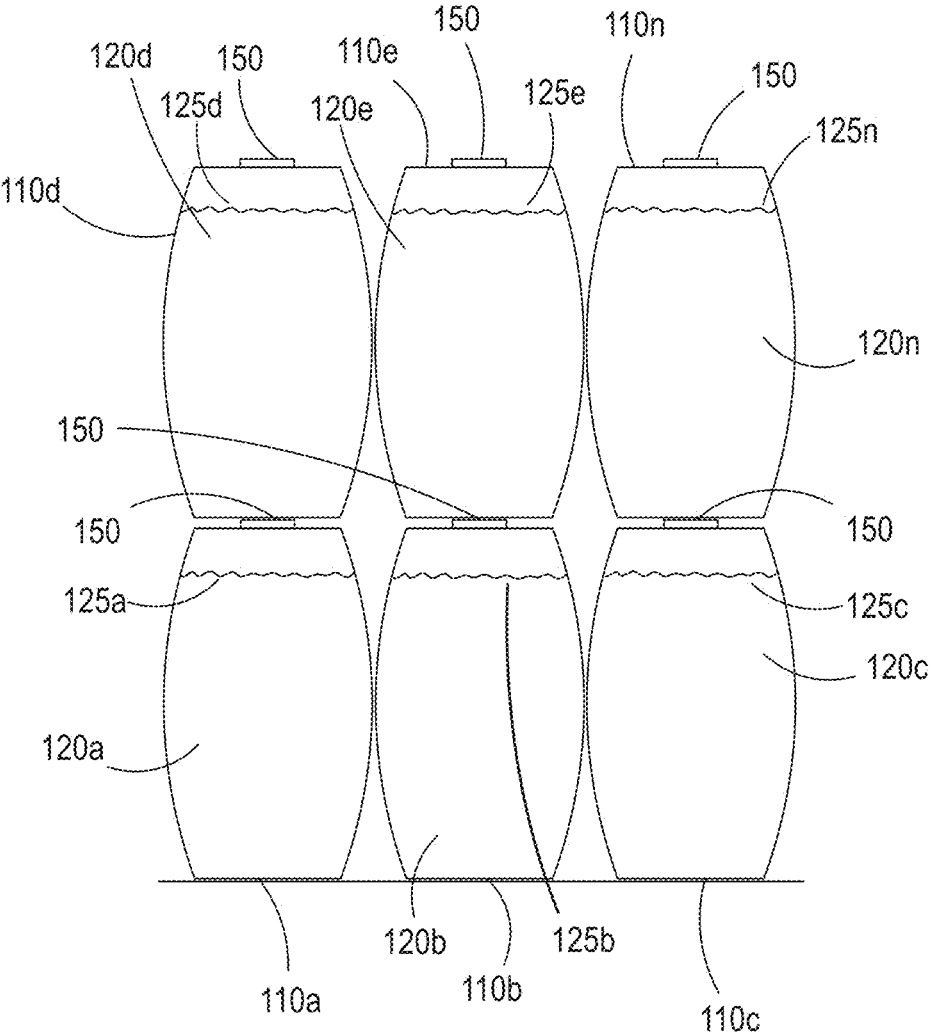
FIG. 9 illustrates a second conventional configuration for storing a plurality of barrels and the liquid contained therein.

FIG. 9 illustrates a second conventional configuration for storing a plurality of barrels and the liquid contained therein.

In this second configuration of storing barrels, barrels 110a, 110b, . . . 110n are stored vertically where monitoring system 150 is attached to face 140 of each of the illustrated barrels 110. The implementation depicted by FIG. 9 shows the exemplary respective liquid levels 125d, 125e, 125n, 125a, 125b, 125c of liquids 120d, 120c, 120n, 120a, 120b, 120c.

In this illustrated configuration, it would be recognized by those skilled in the art that the level of the contained liquid with each of the barrels may be obtained from a single signal or ping, as the level of the liquid is measured from face 140.

Accordingly, monitoring system 150 may be configured to include a single antenna configuration that may be used to monitor the vertically displaced liquid within the vertically stacked container(s) 110.

Figure 10:
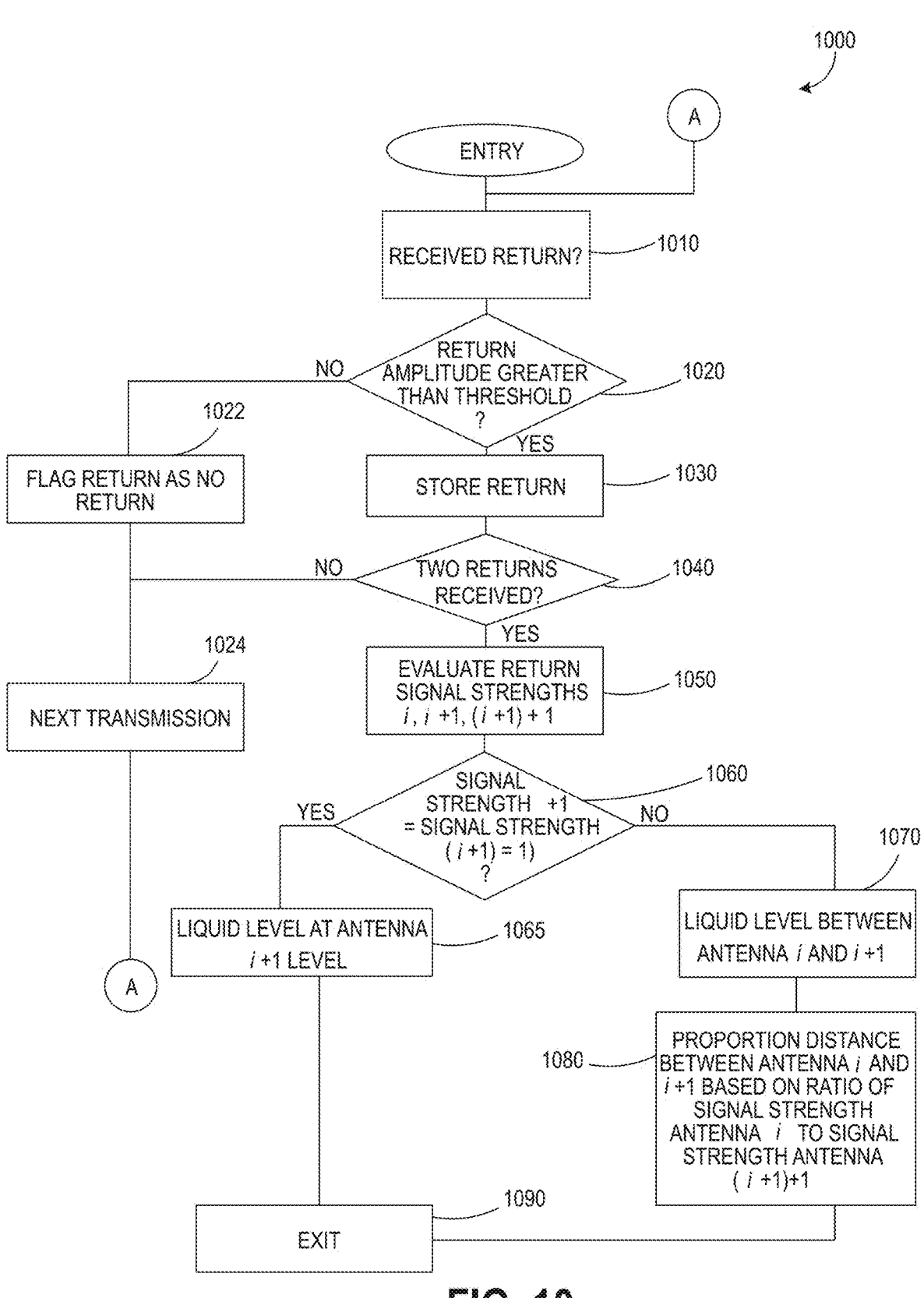
FIG. 10 illustrates a flowchart of an exemplary processing for determining liquid content within a barrel in accordance with the principles of the invention.

FIG. 10 illustrates a flowchart of an exemplary processing for evaluating the return signals in accordance with the principles of the invention.

In accordance with the illustrated processing 1000, a determination is made at step 1010 as to whether a return has been received. If so, a signal strength or amplitude of the received signal (i.e., the return) is evaluated with regard to a threshold level at step 1020. If the received signal strength is less than or equal to a predetermined minimum threshold level, then processing continues to step 1022, where the return is removed from the processing and an indication of NO return is associated with the transmitted ping. At step 1024, a next antenna is selected (as previously discussed) and processing continues at step 1010.

Returning to step 1020, if the return signal strength is greater than the predetermined minimum threshold, then processing proceeds to step 1030 where the return is stored.

At step 1040 a determination is made whether two consecutive returns have been received. If not, then processing proceeds to step 1024, wherein a next transmission is initiated.

However, if two consecutive returns have been received, the processing continues to step 1050 to evaluate the received signal strengths associated with the first return (i.e., antenna i+1) and the second return (i.e., antenna i+1+1).

At step 1060 a determination is made whether the received signal strengths of the two consecutive returns are approximately the same. If so, then the contained liquid level is determined to be comparable to the position of the i+1 antenna at step 1065. Processing then proceeds to step 1090 where the processing is ended.

Returning to step 1060, if the signal strengths are not approximately equal, then the liquid level may be determined to be between the ith and the ith+1 antenna at step 1070. In one aspect of the invention, the liquid level may be determined proportionally between the ith and the ith+1 antenna based on the signal strength of the ith+1 antenna with respect to the signal strength of the ith+1+1 antenna.

Processing then proceeds to step 1090 to exit.

In accordance with the principles of the invention, the determined level of the contained liquid, based on the signal strength of at least two responses or reflections, which are greater than a threshold value may then be transmitted to one or more of the illustrated external devices shown in FIG. 4. In one aspect of the invention, threshold value may be preset within memory 356. Alternatively, a threshold value may be downloaded into memory 356 in a manner as previously discussed. In still another aspect of the invention, the threshold value may be dynamically determined, based in part, on the characteristics of the container. For example, a size of the container, a material of the container, etc. For example, a calibration of the monitoring system 150 may occur once placed on a face 140 of a container, wherein the characteristics of the container and/or contained liquid may be entered into monitoring system 150. A series of transmissions may occur from one or more of antenna 220a . . . 220n, and the responses to the series of transmissions may be evaluated for establishing a threshold value that enables signals that may be considered valid responses to the processed.

In one aspect of the invention, a volume of the contained liquid may be obtained from at least the determined fluid level and knowledge of the physical dimensions of the container. For example, the volume of the barrel or tank may be determined as:

$$V(\text{tank}) = \pi r^2 L, \text{ where } L \text{ is the length of the tank; and}$$
$$r \text{ is the radius of a circular segment of the tank.}$$

The filled volume of a horizontally oriented tank or barrel, for example, may be determined by first finding an area, A, of a circular segment and multiplying it by the length, L. A partial volume calculation may next be derived as:

$$A = (\tfrac{1}{2})r2(\Theta - \sin \Theta)), \text{ where } \Theta = 2 * \arccos(m/r) \text{ and } \Theta$$
$$\text{is in radians.}$$

Accordingly, a volume of a segment may be determined as:

$$V(\text{segment}) = (1/2)r^2(\Theta - \sin\Theta)L.$$

If the determined fluid level, f, is less than ½ of "d", then the segment created from the level height and V(fill)=V (segment).

However, if the fluid level, f, is greater than ½ of "d" then, the segment that is created by the empty portion of the tank may be determined and subtracted from the total volume of the container or tank to obtain:

$$V(\text{fill}) = V(\text{tank}) - V(\text{segment}).$$

In another aspect of the invention, for vertically oriented barrels, the volume of the contained liquid may be obtained as:

$$V(\text{tank}) = \pi r^2 h, \text{ where } h \text{ is height of the contained fluid.}$$

Figures 11A, 11B, 11C:
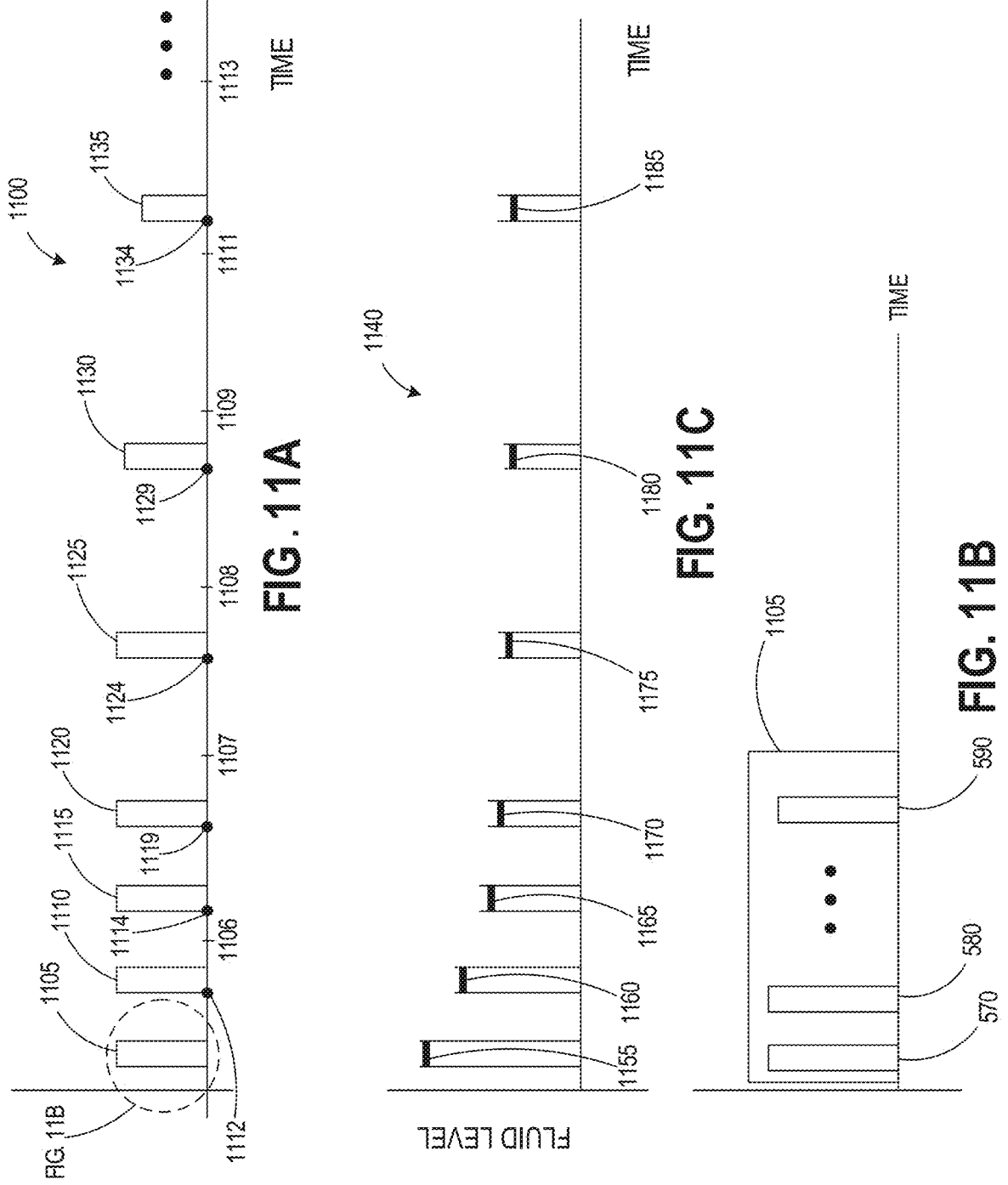
FIGS. 11A-11C illustrate exemplary signal transmission and signal return graphs as a function of time in accordance with one aspect of the invention.

FIGS. 11A-11C illustrate exemplary signal transmission and signal return graphs as a function of time in accordance with a further aspect of the invention.

In accordance with this further aspect of the invention, the quality of a container may be determined by the long-term evaluation of the losses (leakage and/or absorption) of the liquids contained with the container. The long-term evaluation of the losses associated with a container may further be utilized to determine a rate of testing of the liquid within the container.

FIG. 11A illustrates an exemplary signal transmission graph 1100 as a function of time, wherein signal transmissions occur within bursts over an extended period of time. In accordance with the principles of the invention, the duration of the usage of monitoring system 150 is divided into a plurality of periods 1106, 1107, 1108, 1109, 111, 1113 and 1117, which are referred to in this exemplary illustration as collection time periods. Further shown are a plurality of transmission bursts 1105, 1110, 1115 . . . 1150, wherein a measurement of a fluid within a container is made.

FIG. 11B is an expanded view of burst 1105, which is identified as FIG. 11B in FIG. 11A.

In this illustrated example, a plurality of transmissions 570, 580 and 590 (which are comparable to the transmissions shown in FIG. 5B) are included within burst 1105, wherein the plurality of transmissions are associated with at least one of the illustrated antenna 220a-220n, as previously discussed. Accordingly, a collection of fluid levels may be obtained for each of the illustrated transmission bursts.

In one aspect of the invention, processing system 210 may include a timer circuit (not shown) that provides an alarm clock feature that causes processing system 210 to transmit burst 1105, containing transmissions 570, 580, 590. After processing the associated reflections from transmissions 570, 580, 590, processing system 210 may enter a sleep mode, in which little power is consumed. After burst 1105 is completed, processing system 210 may again be activated by the timer circuit (not shown) to cause the transmission of signals (i.e., 570, 580, 590) within burst 1110.

This process of sleeping after each burst is completed and activating after a known time thereafter (e.g., 1112, 1114, 1119, 1124 . . . 1149) repeats for the life of the container or barrel to which monitoring system 150 is attached.

This process of sleeping and activation is advantageous as it provides for extended usable life of a fixed, or dedicated power source.

In one aspect of the invention, the activation time may be substantially constant such that fluid measurement may be made at a known rate. For example, burst transmissions 1105 . . . 1150 may occur at a known rate (e.g., a daily basis, a weekly basis, a monthly basis, etc.). The desired rate of fluid measurement may be inputted into processing system 210 as previously described.

Alternatively, and as shown in FIG. 11A, the rate of fluid measurement may be made dynamically, based on changes in the fluid measurement over time.

FIG. 11C illustrates an exemplary graph 1140 of corresponding fluid levels or container volume determined based on the return signals associated with the transmission bursts.

In this exemplary graph, a fluid level or container volume value 1155 may be determined based on the signal transmissions/signal returns associated with burst 1105. Similarly, a fluid level or container volume value 1160 may be determined based on the signal transmissions/signal returns associated with burst 1110. And in accordance with the principles of the invention, fluid levels or container volumes 1165, 110, 1175, 1180 1185, 1195, etc. may be determined based on the signal transmissions/signal returns associated with corresponding transmission bursts 1115, 1120, 1125, 1130, 1135, 1150, etc.

As illustrated, the determined fluid level, or volume, initially decreases from a high value 1155 (i.e., full barrel) to a lower value 1175 and then remains substantially constant (i.e., 1175, 1180, 1185) as the losses from leakage and/or absorption decrease over time.

Accordingly, the rate of change of the fluid level or volume may, thus, be used to determine a duration of a sleep state of processing system 210. For example, when the rate of change of the fluid level is high (e.g., level 1155 to level 1160), signal transmission bursts and subsequent level measurements may be performed at a first rate (e.g., once/day). However, as the rate of change of the measured fluid level is slowing (e.g., level 1165 to level 1170) the duration of a sleep state of processing system 210 may be increased such that signal transmission bursts and measurements are performed at a second rate (e.g., once/week). In addition, as the rate of change of the measured fluid level is determined to be substantially negligible (e.g., level 1180 to level 1185) the duration of the sleep state of processing system 210 may be increased still further.

This dynamic determination of the rate of measurement is further advantageous as it further decreases the power needed to maintain monitoring system 150 for extended periods (e.g., multiple years).

Figure 12:
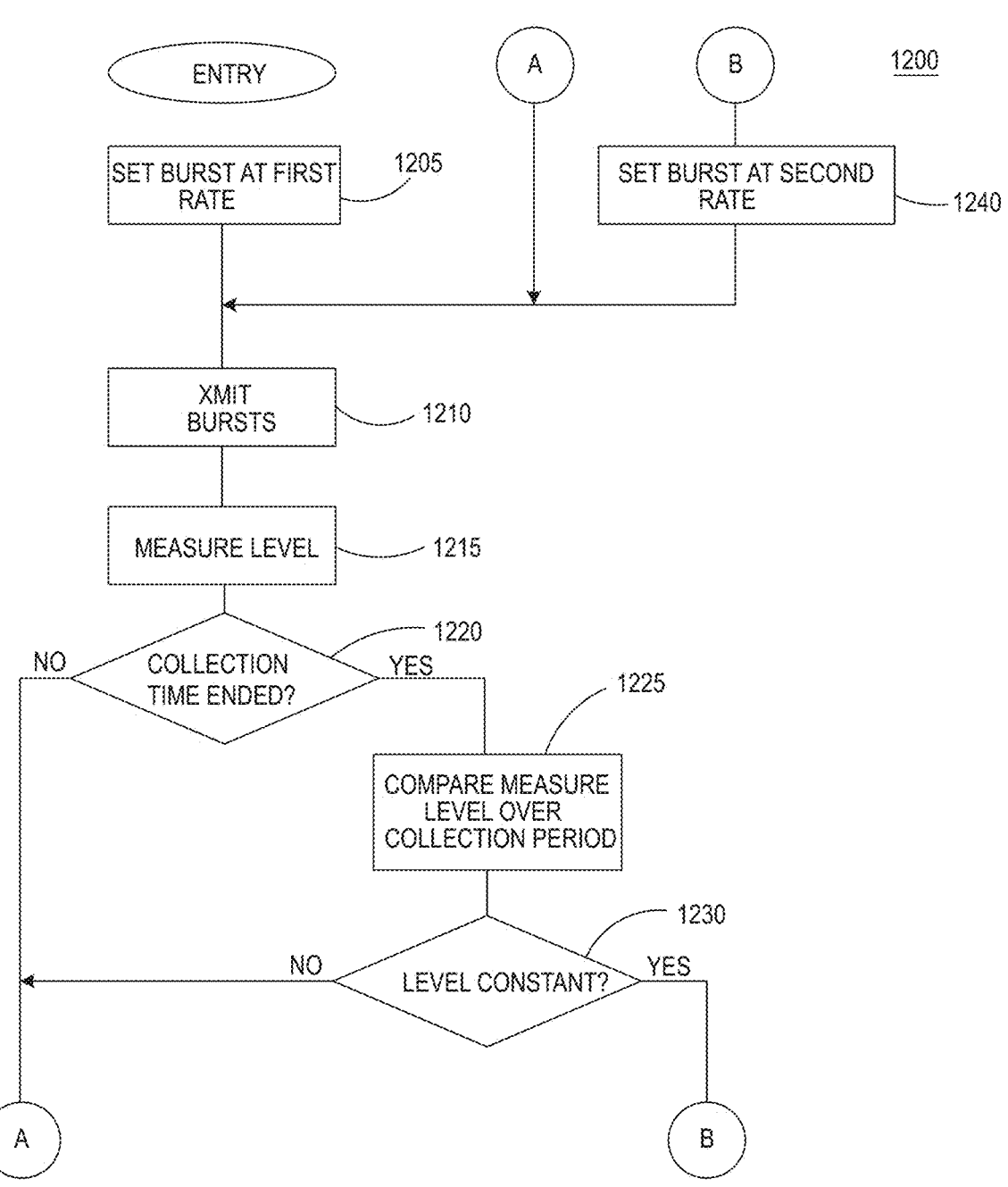
FIG. 12 illustrates an exemplary processing associated with the graphs shown in FIGS. 11A and 11B.

FIG. 12 illustrates an exemplary processing 1200 associated with the graphs shown in FIGS. 11A-11C.

In this illustrated process, the rate of burst transmission 1105-1150 (each containing signal transmission 570, 580 590) is set to a first rate at step 1205. At step 1210, a burst transmission (e.g., 1105) occurs wherein a fluid level (or volume) is determined at step 1215, as previously discussed. At step 1220, a determination is made whether a collection time has ended. If not, then processing proceeds to step 1210 to cause the emission of a second or next burst transmission (e.g., 1110), wherein a second measurement level is determined. At step 1220, a determination is again made as to whether a collection time has ended (e.g., 1106).

If the collection time has ended, processing proceeds to step 1225, wherein the determined fluid level (volume) (e.g., 1155, 1160) are evaluated to determine a rate of change of the determined fluid levels.

At step 1230, a determination is made whether the rate of change is small (i.e., substantially constant level). If the rate of change is not small (i.e., fluid level is not substantially constant) then processing proceeds to step 1210, wherein a next set of burst transmission (e.g., 1115, 1120) occur at the first rate.

However, if the rate of change of the fluid level is small (i.e., fluid level is determined to be substantially constant), then processing proceeds to step 1240, wherein the rate of subsequent transmission bursts is set to a second rate. As shown in FIG. 11A, the second rate is increased such that processing system 210 remains in a sleep state for a longer period and a lesser number of burst transmissions 1130, 1135 occur in an associated collection time period.

To further provide valuable information to the distillers, a measure of alcohol content of the remaining fluid may be determined from the determined evaporation/absorption of the fluid or liquid within the container.

Distilled liquids are stored in warehouses that are generally not climate controlled, and, hence, the ambient or surrounding environment affects the rate of evaporation and/or absorption of the contained liquids.

Environmental factors, such as temperature, barrel characteristics, time and geography contribute to a rate of change of an alcohol content of the fermenting liquid or fluid within a container. Local climate, which includes temperature, temperature fluctuations, and humidity, also affects the rate of evaporation. Local geography, such as altitude, seasonal variations and air quality also affects the rate of evaporation, and, consequently, the alcohol content within the barrel. In addition, the condition of the container is also a factor in the rate of production of alcohol in the container.

Figure 13:
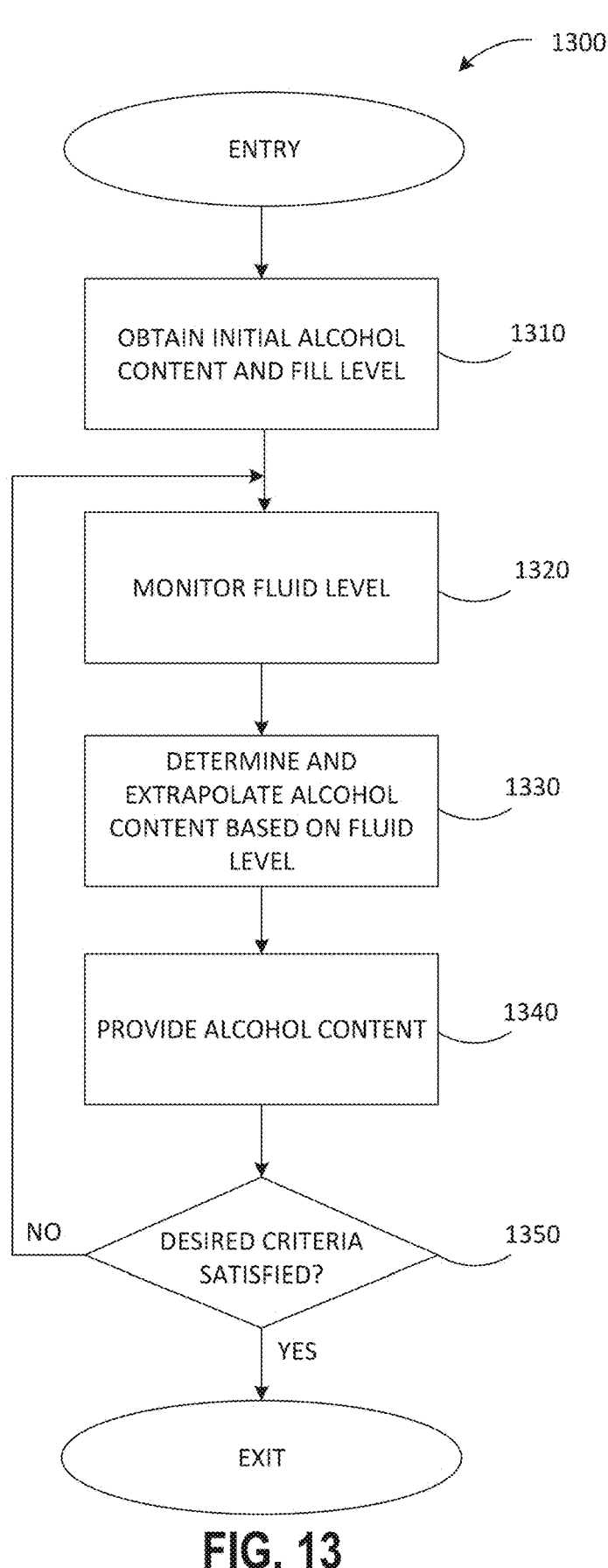
FIG. 13 illustrates a flowchart of an exemplary process associated with a determination of an alcohol content within a container in accordance with the principles of the inven-tion.

FIG. 13 illustrates an exemplary process for determining alcohol content of a fermenting fluid within a container in accordance with the principles of the invention.

In this illustrated exemplary process 1300 upon filling a barrel or container with a liquid that is to be fermented, a measure of an initial alcohol content is determined and stored at step 1310. For example, the liquid entered into the container or barrel represents a mash that has been obtained from a distillation process associated with the fermentation of a base material, such as barley, rye, corn, wheat or a combination thereof.

At step 1320, a measure of the fluid level within the container is made. The measure of fluid level may be determined continuously, periodically or intermittently, utilizing one or more of the methods previously discussed.

At step 1330, a determination of an alcohol content is performed based at least on a determined fluid level and one or more environmental factors. At step 1340, the determined alcohol content is presented to a user for evaluation.

At step 1350 a determination is made whether one or more criterion associated with a desired requirement is satisfied. For example, determined alcohol content is within a desired range and/or a minimum length of time of the aging of the liquid within the container has been exceeded.

If one or more criterion is not satisfied, processing proceeds to step 1320 for further continued monitoring of fluid level and evaluation of alcohol content. As previously discussed, the monitoring of the fluid level (and evaluation of alcohol content) may be determined periodically or continuously. In one aspect of the invention, the period of sampling may be based on a duration of time the liquid is within the barrel. That is, the interval between sampling is shorter during the early stages of fermentation and longer as the period of fermentation is increased.

Otherwise, processing is ended.

Figure 14:
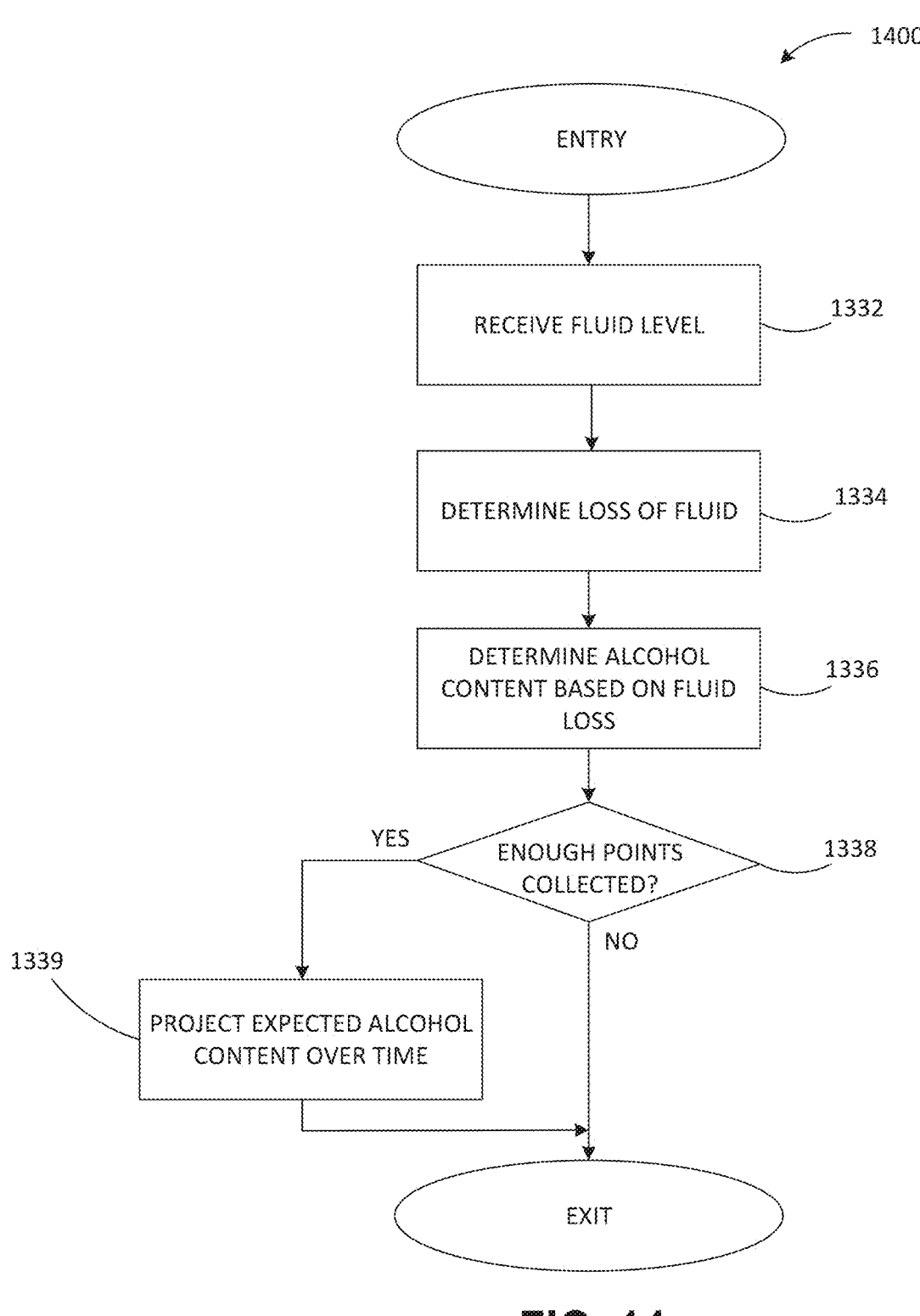
FIG. 14 illustrates a flowchart of an exemplary process for determining and extrapolating alcohol content of a liquid within a container in accordance with the principles of the invention.

FIG. 14 illustrates a flow chart of an exemplary processing associated with step 1330 of FIG. 13 for determining and extrapolating alcohol content of a liquid within a container in accordance with the principles of the invention.

In this exemplary process 1400, processing receives at step 1332 a fluid level obtained from a monitoring system, as previously discussed. At step 1334, a determination of a loss of fluid or liquid is determined, wherein the loss of fluid may be due to evaporation of the fluid or absorption of the fluid by the container as the container remains in place over an extended period of time.

At step 1336, an alcohol content of the liquid or fluid remaining in the container is determined, wherein the alcohol content is determined based, in part, on the at least one of an initial alcohol content, and one or more environmental conditions.

At step 1338 a determination is made as to whether enough data points have been collected. If enough data points have been collected, a determination of an expected alcohol content (i.e., a projection of alcohol content) is performed at step 1339. For example, and as would be known in the art, when two data points are collected, a straight line approximation of the alcohol content may be obtained. In an illustrative example, when three data points are collected, a curved line, passing through the collected points, may be formulated that provides for an approximation of the expected alcohol content. When additional sample points are collected, a more accurate approximation of the expected alcohol content may be obtained. In one aspect of the invention, at least three data or sample points are to be collected to obtain a first order approximation of the expected alcohol content. In another aspect of the invention, the process of determining an approximation of the expected alcohol content is performed as a selected number (e.g., a specified subset, or all) of the data points collected so as to obtain a more accurate approximation of the expected alcohol content.

Otherwise, processing exits.

Figure 15:
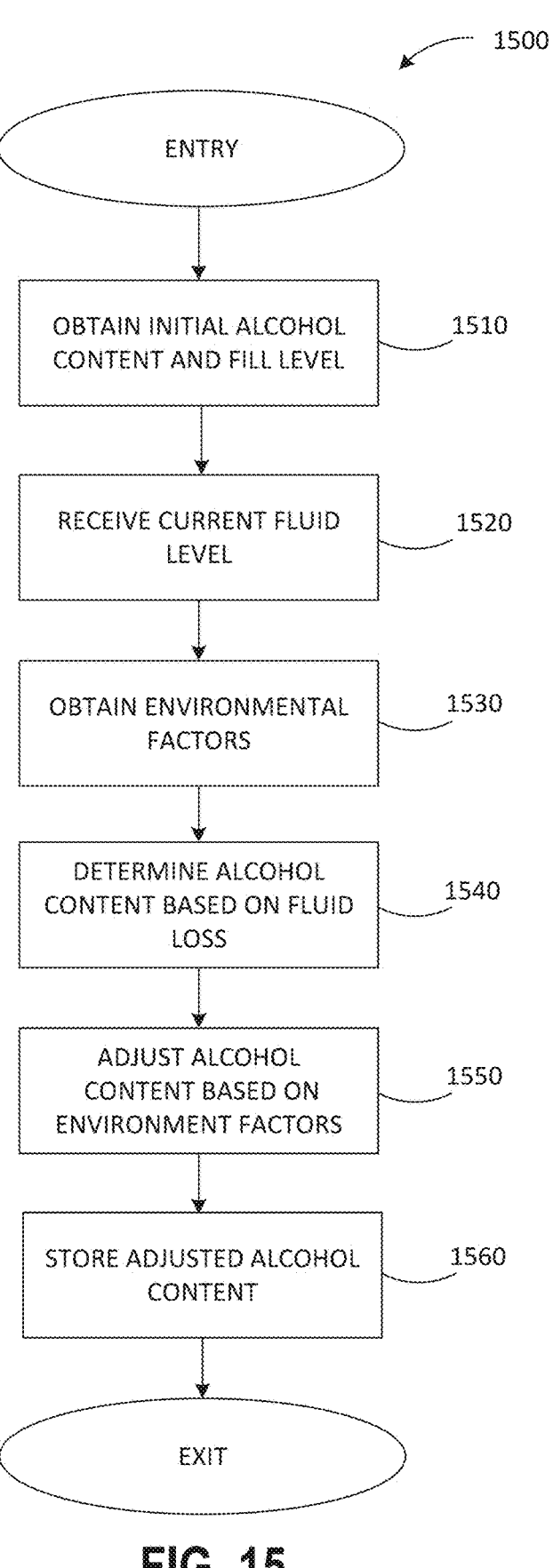
FIG. 15 illustrates a flowchart of an exemplary process for determining alcohol content of a liquid within a container in accordance with the principles of the invention.

FIG. 15 illustrates a flowchart of an exemplary process associated with step 1336 of FIG. 14 for determining alcohol content of a liquid within a container in accordance with the principles of the invention.

In the illustrated process, an initial alcohol content and fill level are obtained at step 1510. At step 1520, a determination of a loss in liquid or fluid level is based on the initial fill level and the determined current fill level. At step 1530, environmental factors surrounding the container are obtained. These factors may include information regarding temperature, humidity, seasonal variations, etc.

At step 1540 a determination of a current alcohol content is determined from the determined loss, wherein a nominal alcohol content decrease (or increase) is utilized to determine the current alcohol content. In one aspect of the invention, the nominal alcohol content decrease or increase is substantially constant over time. In another aspect of the invention, the nominal alcohol content increase or decrease may be variable, wherein the nominal alcohol content increase or decrease varies over time. In one aspect of the invention, the alcohol content may be determined based on a model of alcohol content over time, wherein the model may be developed by a series of actual measurements obtained over a known time period.

At step 1550 the determined alcohol content is subjected to a process for adjusting the determined alcohol content based on environment factors. At step 1560, the adjusted alcohol content is stored for subsequent processing.

Figure 16:
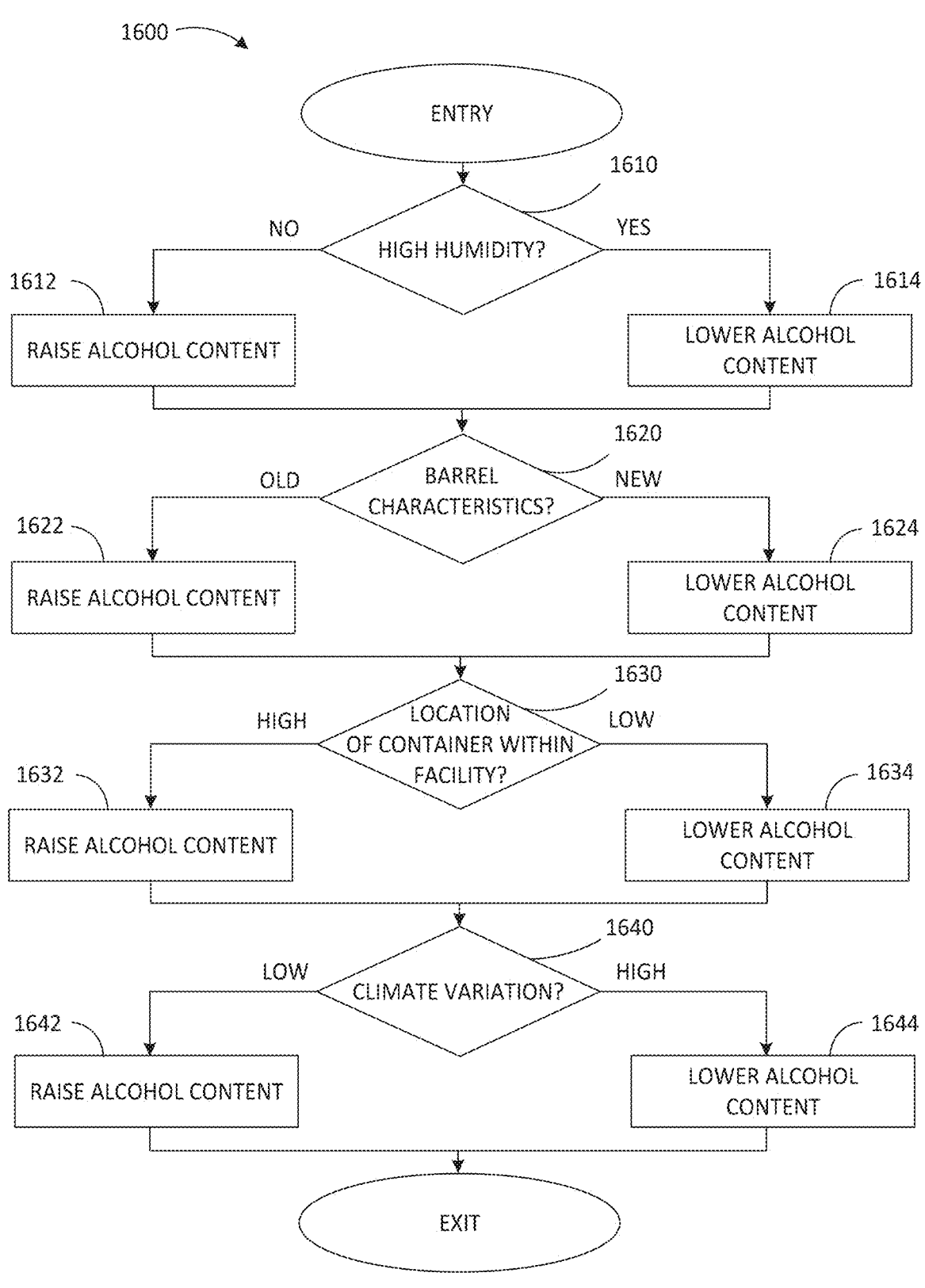
FIG. 16 illustrates a flowchart of an exemplary process for adjusting a determined alcohol content based on environ-mental considerations.

FIG. 16 illustrates a flowchart of an exemplary process associated with adjusting alcohol content presented in step 1550 based on one or more environmental factors or considerations.

In accordance with this exemplary processing 1600, at step 1610, a determination is made regarding the humidity level in the surrounding environment. If it is determined that the humidity level is high, then the alcohol content is lowered at step 1614, as alcohol evaporates more quickly in high humidity conditions than water. In an illustrative example, a threshold humidity level of fifty percent may be considered as a high humidity level. The threshold humidity level may be adjusted in accordance with what would be known to one of ordinary skill. Otherwise, the alcohol content is raised at step 1612. The degree of raising or lowering the alcohol content may be constant. Alternatively, the degree of raising or lowering the alcohol content may be varied based on the level of humidity. In still another aspect, the degree of raising or lowering the alcohol content may be varied based on a length of time the contained fluid or liquid has been subjected to the humidity conditions.

At step 1620, a determination is made regarding the condition of the container. If it is determined that the container is essentially new, or has been used a few times, then processing proceeds to step 1624 where the alcohol content is lowered, as a newer container affords greater absorption of the contained fluid. Otherwise, at step 1622 the alcohol content is raised, as there is less absorption of the contained fluid.

At step 1630, a determination is made regarding a location of the container. For example, a determination of a high position within a stack of containers may require a raising of the alcohol content, at step 1632 as the higher position may cause greater temperature fluctuations around the container. Otherwise, the alcohol content may be lowered at step 1634 as it is expected that less temperature fluctuation exists around the lower-positioned container.

At step 1640, a determination is made regarding climate variations, wherein high climate (e.g., high altitude, northern geographical location, etc.) may require a lowering of the alcohol content at step 1644, while a lower climate (e.g., lower altitude, more southern geographical location, etc.), may require the alcohol content to be retained the same or raised at step 1642.

Processing then exits with an adjusted alcohol content level.

Although processing 1600 refers to a limited number of factors that may be considered in adjusting a determined alcohol content, it would be within the knowledge of those skilled in the art to include additional factors that may affect the alcohol content of a contained liquid over time. For example, such additional factors may include but not be limited to the condition of the container (the condition of the container may include further elements of the nature of the inner surface (e.g., charred, not charred) of the container), the length of time the container has been in service, the number of times or cycles that the container has been utilized, and the like.

Such additional factors have been contemplated by the inventors and are included within the scope of the invention claimed.

Figure 17:
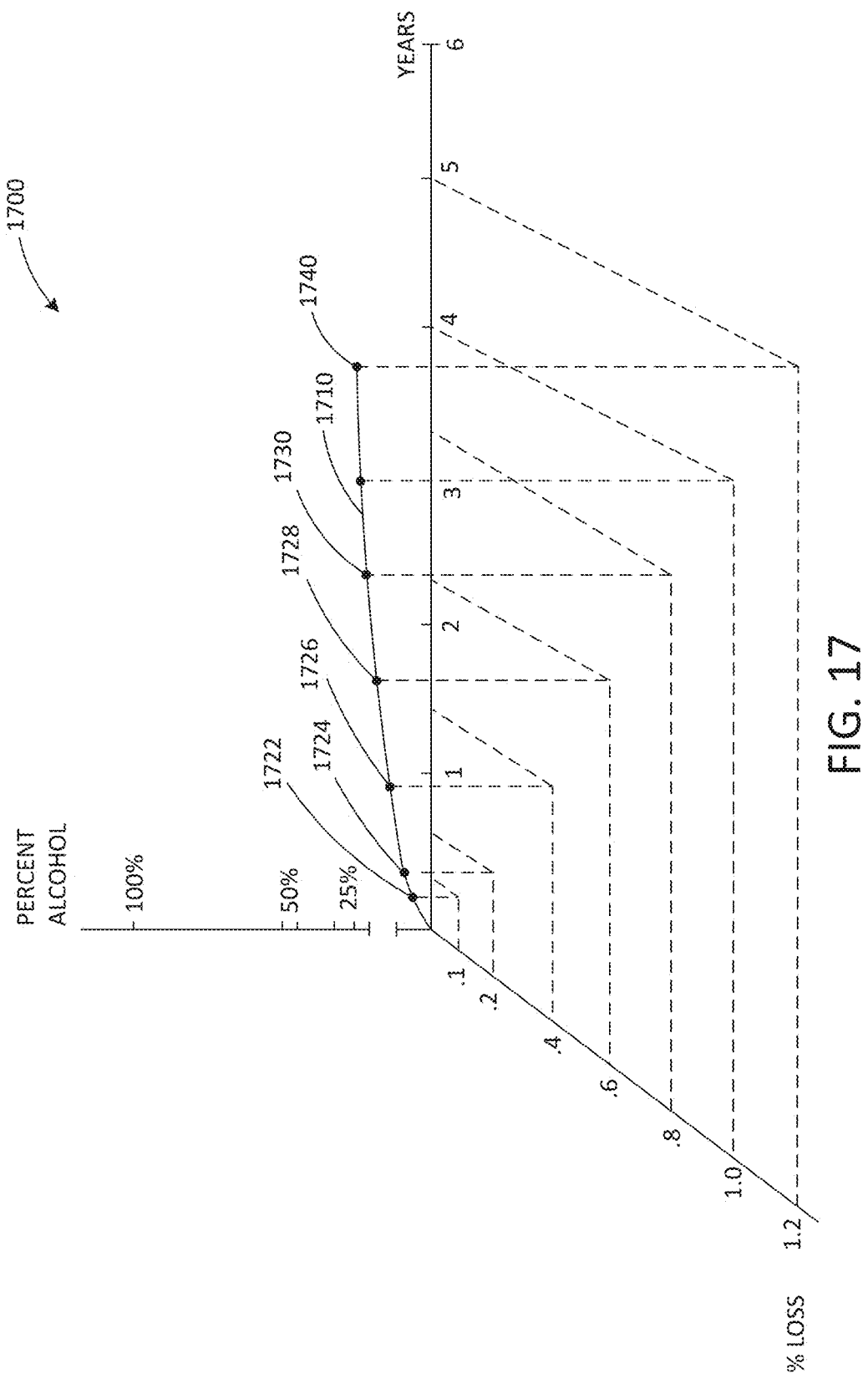
FIG. 17 illustrates an exemplary plotting and extrapolat-ing alcohol content of a liquid within a container in accor-dance with the principles of the invention.

FIG. 17 illustrates an exemplary plot of determined alcohol content and extrapolating alcohol content in accordance with the principles of the invention.

In this illustrated example, chart 1700 comprises a horizontal axis onto which a number of years of storage of a container is plotted and a vertical axis onto which is plotted a percentage of alcohol content of the contained fluid. In addition, on a third coordinate, is shown that represents a percentage of loss of liquid within the container. Accordingly, a three-dimensional formulation or model of alcohol content versus percentage of fluid loss versus a period of time may be determined, wherein an expected or typical alcohol content may be determined from a determination of a loss of fluid.

Plot line 1710 represents an approximation of a change in alcohol content versus fluid loss, wherein plot line 1710 represents an idealized representation of the development or production of alcohol of the fermenting liquid within the container that may be obtained using mathematical formulation. Alternatively, plot line 1710 may correspond to a series of actual measurements of alcohol content made using conventional methods. For example, measurements or data points 1722, 1724, 1726, 1728, 1730 . . . 1740 may represent one or more measurements of both fluid loss and alcohol content of the fermenting liquid at known periods of time. For example, measurements, or data points 1722, 1724 . . . 1740 may be taken periodically (i.e., monthly) or randomly.

Based on the measurements or data points 1722-1740, plot line 1710 may then be formulated using statistical methods (e.g., "line of best fit," "least squares," etc.) to produce an approximation of the change in alcohol content that best represents the measured points. Although a "line of best fit" or "least squares" method are discussed, it would be recognized by those skilled in the art that other statistical methods may be utilized to formulate plot line 1710 without altering the scope of the invention claimed.

Figure 18:
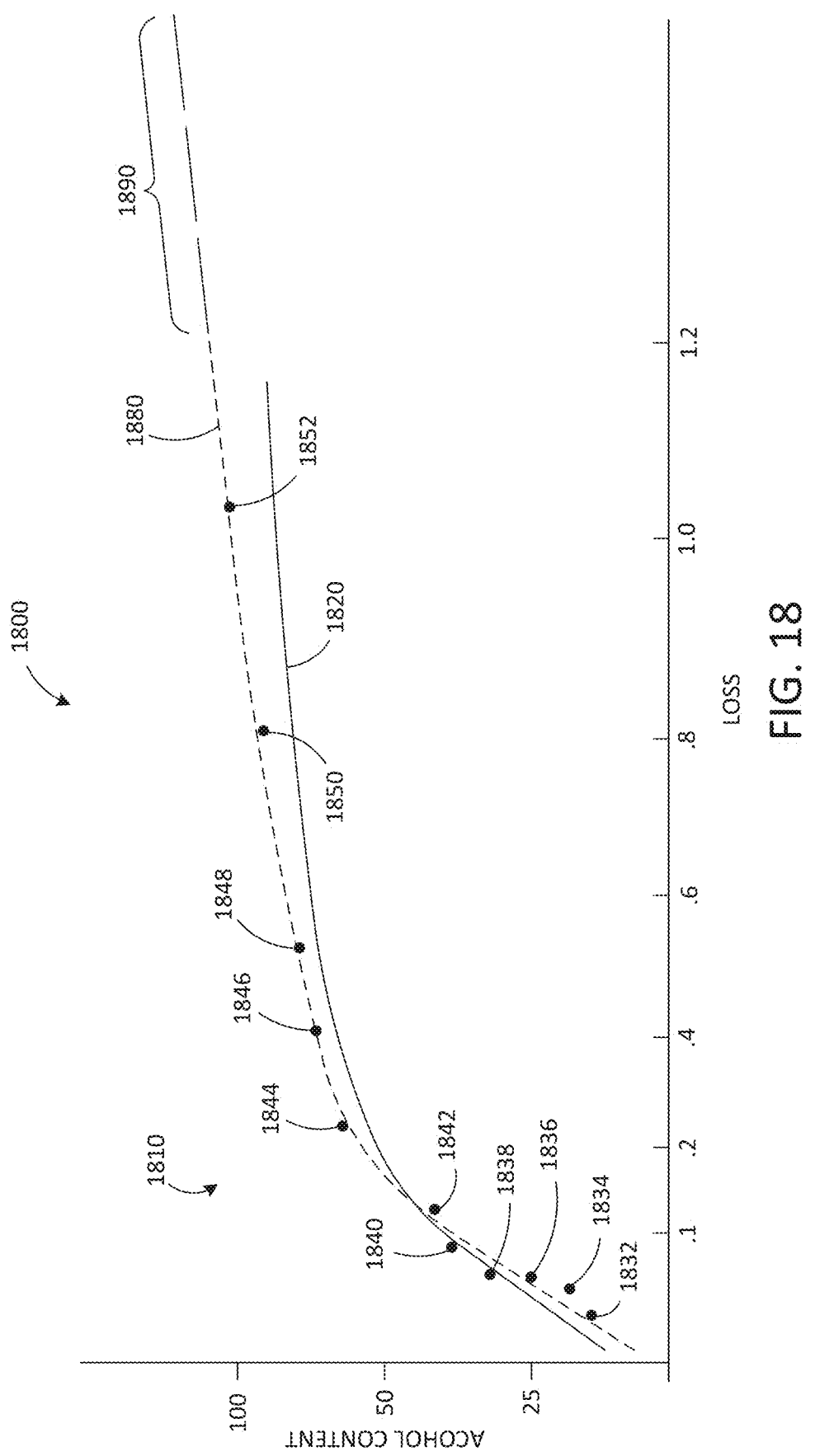
FIG. 18 illustrates an exemplary graph of alcohol content determination in accordance with the principles of the invention.

FIG. 18 illustrates an exemplary graph of alcohol content determination in accordance with the principles of the invention.

FIG. 18 represents a projection 1820 of the idealized or model plot line 1710 onto the two-dimensional plane 1810 of alcohol content versus percent of loss shown in FIG. 17.

In accordance with the principles of the invention, utilizing the idealized projection 1820, an estimate (i.e., a first order) of the measure of alcohol content may be determined based on a determined fluid loss. That is, preliminary (i.e., first order) alcohol content measurements may be determined for each of the measurement points based on the determined fluid loss taken at different times. A more refined alcohol measurement may be determined from the preliminary alcohol content at each of the measured (i.e., collected) data points by adjusting or modifying the preliminary alcohol content by one or more environmental factors, as shown and discussed with regard to FIG. 16. Measurements 1832, 1834, 1836, 1838 . . . 1852, represent the more refined measurements of alcohol content after considering one or more environmental factors for corresponding ones of the expected alcohol content based on the model shown in FIG. 17.

In accordance with the principles of the invention, the measurements of fluid loss (and determination of alcohol content) may be taken at a first rate during a first period of time while subsequent measurements of fluid loss may be taken at a second rate during a second period of time, wherein the second rate is longer than the first rate. That is, the periodicity of the measurement rate (i.e., first rate and second rate) increases over time.

For example, during a first year, when alcohol production and fluid loss is greatest, fluid loss measurements may be taken at a first rate (e.g., 1832 . . . 1842) and when alcohol production and fluid loss is less, fluid loss measurements may be taken at a second rate (e.g., 1848, 1850, 1852), wherein the first rate is higher (i.e., measurements performed more often) than the second rate.

Further illustrated is a statistical formulation of the measured samples 1832, 1834 . . . 1852, as represented by the dashed plot line 1880. Similar to the formulation discussed with regard to FIG. 17, dashed plot line 1880 represents a model that may be provided to refine the model shown in FIG. 17. For example, a plurality of plot lines 1880, taken from a corresponding measurement of a plurality of containers that have similar characteristics (i.e., geographical location) may be accumulated and included in model 1710.

In one aspect of the invention, plot line 1880 or model may be utilized to determine a projection 1890 of an expected alcohol content that, when projected onto the plane of alcohol v. years, shown in FIG. 17, may provide information of alcohol production for subsequent years.

Various implementations have been disclosed with reference to the Drawings. However, other implementations are possible. For example, an exemplary method may comprise receiving information regarding an initial state of a liquid in a container, the initial state comprising at least one of: an alcohol measure and a level of the liquid within the container; monitoring a level of the liquid within the container, wherein the monitoring is performed external to the container; determining an amount of loss of the liquid within the container based on the initial level and the monitored level; and estimating the alcohol measure of liquid remaining within the container based on the determined amount of loss of the liquid.

The method may further comprise storing a plurality of estimated alcohol measures.

The method may further comprise extrapolating an expected alcohol measure based on the stored plurality of estimated alcohol measures.

Estimating the alcohol measure may further comprise adjusting the estimated alcohol measure based on at least one environmental condition.

The at least one environmental condition may be selected from a group consisting of: temperature, location within a facility, a geographic location of the facility, and container condition.

The determination of estimating the alcohol measure may be performed periodically.

The rate of periodicity estimating the alcohol measure may be adjustable.

The rate of periodicity estimating the alcohol measure may be increased as a function of time.

An exemplary system may comprise a plurality of antennas positioned on an exterior surface of a barrel, wherein the plurality of antennas are configured to capture signals reflected by a liquid within the barrel; and a processor configured to: receive the reflected signals; and determine a level of the liquid within the barrel, wherein based on the determined level of the liquid within the barrel, the processor is further configured to: determine a loss of liquid within the barrel based on the determined level of fluid and an initial level of fluid; and estimate an alcohol content of the liquid within the barrel based on the determined loss of liquid.

The system may further comprise the processor may be configured to store the estimated alcohol content.

The system may further comprise the processor may be configured to extrapolate an expected alcohol content based on a stored plurality of estimated alcohol measures.

The system may further comprise the processor may be configured to adjust the estimated alcohol content based on at least one environmental condition.

The at least one environmental condition may be selected from a group consisting of: temperature, location within a facility, a geographic location of the facility, and container condition.

The determination of estimating the alcohol content may be performed periodically.

The rate of periodicity estimating the alcohol content may be adjustable.

The rate of periodicity estimating the alcohol content may be adjustable as a function of time.

An exemplary method may comprise: determining, by a monitoring system external to a container, a level of a liquid within the container; and estimating an alcohol content of the liquid within the container based on the determining level of the contained liquid, wherein the estimation comprises: determining an amount of loss of liquid based on the determined level of liquid; obtaining a first order alcohol content based on a model expectation of alcohol content; and determining the alcohol content based on adjusting the first order alcohol content based on at least one environmental condition.

The at least one environmental condition may comprise at least one of: a temperature, a location within a facility, a geographic location of the facility, and a container condition.

The method may further comprise projecting an estimated alcohol content based on a plurality of the determined alcohol content.

The method may further comprise determining the level of liquid within the container periodically, wherein measurements of the level of liquid is performed at a first rate during a first period of time and at a second rate during a second period of time, the first rate being faster than the second rate.

Figure 19:
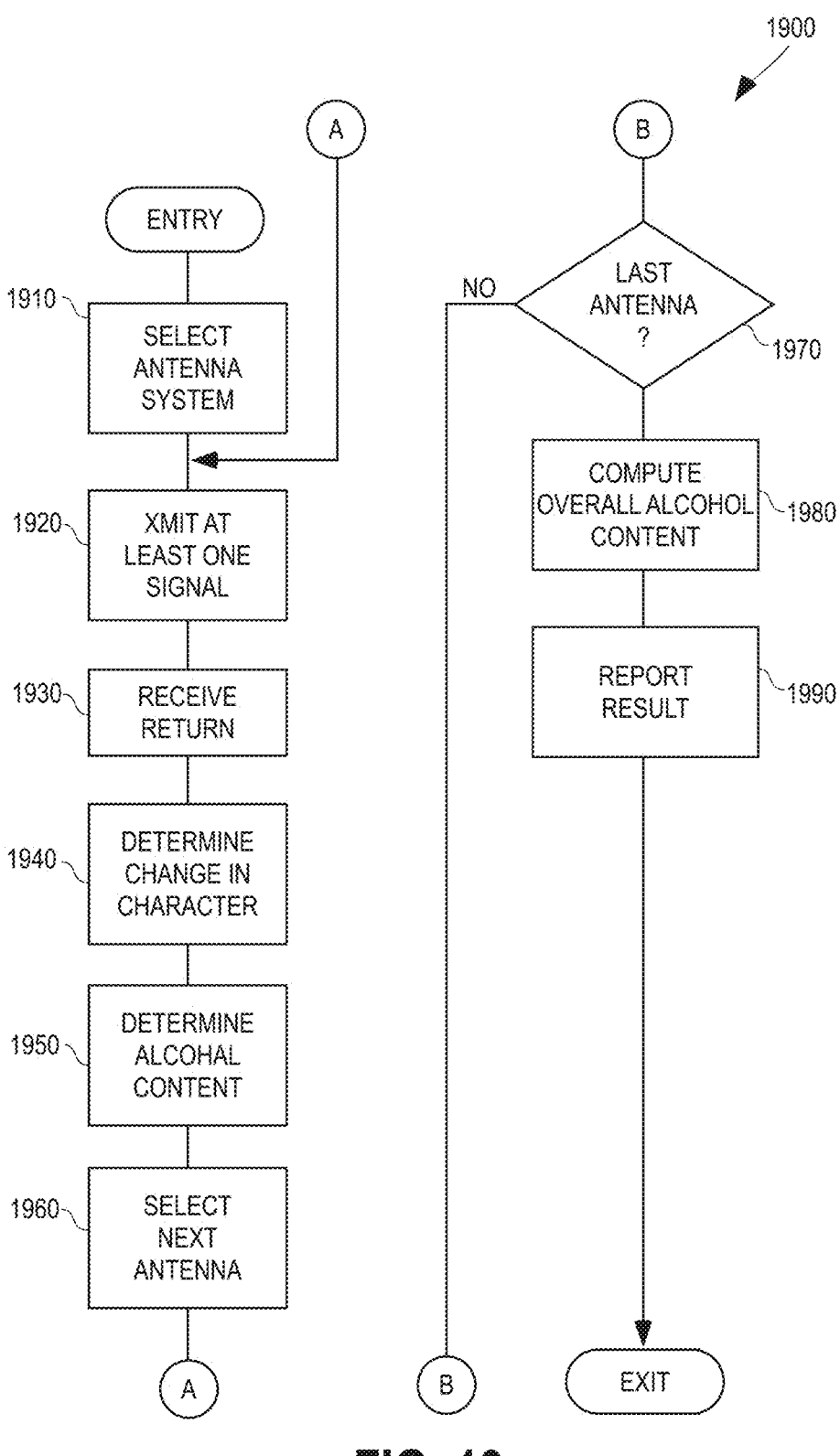
FIG. 19 illustrates a flowchart of a second exemplary process associated with a determination of an alcohol content within a container in accordance with the principles of the invention.

FIG. 19 illustrates a flowchart of a second exemplary process for determining alcohol content of a fluid within a container in accordance with the principles of the invention.

In a further aspect of the invention claimed, the system configurations shown in FIGS. 2, 7A, 7B may be further utilized to determine alcohol content directly. Thus, while alcohol content determination has been discussed with regard to determination of fluid loss, the system may employ a second algorithm in conjunction with or independent of the processing previously disclosed.

In this aspect of the invention, monitoring system 150 may implement the illustrated exemplary process 1900, wherein a first antenna from a set of antenna selected from a plurality of antenna associated with the externally mounted antennas shown in FIGS. 2, 7A, 7B is selected at step 1310. In one aspect of the invention, the first antenna among the set of antenna selected may be associated with the lowest position (e.g., 220*n*) among the illustrated plurality of antenna 220*a*-220*n*. Alternatively, the first antenna among the set of antenna may be selected based on a determined level of fluid within the container, wherein the first antenna selected is that antenna that is associated with the highest level of fluid (e.g., the top-most antenna initially). In still a further alternative embodiment, the set of antenna may be selected as a single antenna. For example, the physically lowest positioned antenna may be selected as being included as the sole selected antenna within the set of antenna. In still a further aspect, the sole selected antenna within the set of antenna may be selected as that antenna located physically positioned at or just below the fluid level of the fluid within the barrel. In still a further aspect, the sole selected antenna within the set of antenna may be selected as that antenna physically positioned between the lowest positioned antenna and the antenna positioned at or just below the level of fluid. Although examples of the selection of the one or more antenna selected to be within the set of antenna are disclosed, it would be recognized that other methods of selection of antennas within the set of antenna may be implemented without altering the scope of the invention claimed.

In one aspect of the invention upon filling a barrel or container with a liquid that is to be fermented, a measure of an initial alcohol content may be determined and stored at step 1910. For example, the liquid entered into the container or barrel may represent a mash that has been obtained from a distillation process associated with the fermentation of a base material, such as barley, rye, corn, wheat or a combination thereof.

At step 1920, at least one signal may be transmitted in at least one frequency band from the selected antenna into the contained fluid. A return (i.e., return or reflected signal) associated with each of the transmitted at least one signal is captured at step 1930. At step 1940 a determination of a difference in at least one characteristic (e.g., signal strength, frequency, phase, distance and/or time traveled) between the transmitted signal and the return or reflected signal is made.

In one aspect of the invention, processing system 210 may include a frequency shifting measurement circuit that allows for the determination of a difference between a frequency of the transmitted signal and a frequency of the associated return signal. Alternatively, processing system 210 may include phase shifting measurement circuitry that allows for the determination of a difference between a phase of the transmitted signal and a phase of the associated return signal.

At step 1950, an alcohol content associated with the selected antenna of the fluid within the container may be obtained based on a change in the characteristic (e.g., signal strength, frequency, phase, distance and/or time traveled) of the returned signal.

In one aspect of the invention, the selected antenna may transmit at least one signal (or plurality of signals) at a same frequencies with different phases into the contained fluid, wherein the difference in phase between each of the at least one (plurality of) transmitted signals and the associated returned signal nay be determined. In one aspect of the invention, the at least one (plurality of) phase differences may be accumulated and averaged, for example, to obtain an average phase difference. An alcohol content, associated with the selected antenna, may be determined, for example, based on the obtained average phase difference. In another aspect of the invention, the selected antenna may transmit at least one signal (or a plurality of signals) at different frequencies with a same phase into the contained fluid, wherein a difference in frequency between each of the at least one (plurality of) transmitted signal(s) and the associated return may be determined. In one aspect of the invention, the at least one (plurality of) frequency differences may be accumulated and averaged, for example, to obtain an average frequency difference. An alcohol content, associated with the selected antenna may be determined, based on the obtained frequency difference. In still another aspect of the invention, the selected antenna may transmit a plurality of signals at different frequencies and at different phases. Differences in frequency and phase between the transmitted signals and the return signals may be determined, accumulated and averaged to obtain an average frequency and phase values. An alcohol content may be determined based on the averaged frequency and phase values.

At step 1960, a next antenna from set of antenna of the plurality of antenna is selected. At step 1970 a determination is made whether a last antenna has been selected. In one aspect of the invention, the last antenna may be selected as the last antenna among the plurality of antenna. In another aspect of the invention, the last antenna may be selected as the last antenna associated with a fluid level within the container.

If the last antenna is not selected, processing proceeds to step 1920 wherein at least one signal is transmitted by the selected antenna and the processing illustrated by at least steps 1930 to 1950 for obtaining alcohol content associated with the selected antenna is performed.

However, if the last antenna of the set of antenna has been selected, then processing proceeds to step 1980, wherein an average (or a median) alcohol content may be determined based on the previously determined alcohol content associated with each of the selected antenna. At step 1990, a report of the determined alcohol content may be provided.

In one aspect of the invention, the average (or median) alcohol content may be determined based on a filtering of the alcohol content associated with each of the selected antenna. For example, the average (or median) alcohol content may be obtained by removing a high alcohol content and a low alcohol content from the collected set of alcohol content in order to remove singular values. Alternatively, the average (or median) alcohol content may be obtained by first removing the alcohol content associated with the last selected antenna and averaging or accumulating the remining values. In this manner, the determined average (or median) alcohol content obtained is not influenced by an alcohol content at the fluid/air boundary.

Although, the process shown in FIG. 19 contemplates determining an alcohol content from the determined alcohol content associated with each of the selected antenna, it would be recognized by those skilled in the art that resultant characteristics (e.g., signal strength change, frequency shift, phase shift, change in distance and/or time traveled, etc.) may be obtained for each of the selected antenna, and an alcohol content may be obtained based on a resultant characteristic obtained over all the selected antenna within the set of antenna.

In accordance with the principles of the invention, the alcohol content obtained utilizing the processing shown in FIG. 19 may be further adjusted in a manner similar to that described with regard to FIGS. 15 and 16.

In still another aspect of the invention, the alcohol content obtained utilizing the processing shown in FIG. 19, may be correlated with the alcohol content obtained utilizing the processing shown in FIG. 14. Alternatively, the alcohol content obtained utilizing the processing shown in FIG. 19, may supplement the alcohol content obtained utilizing the processing shown in FIG. 14 to improve the model as shown in FIGS. 17 and 18.

FIGS. 20A-D illustrate exemplary charts of alcohol content of a liquid within a container for different transmitted frequencies.

Figures 20A, 20B, 20C, 20D:
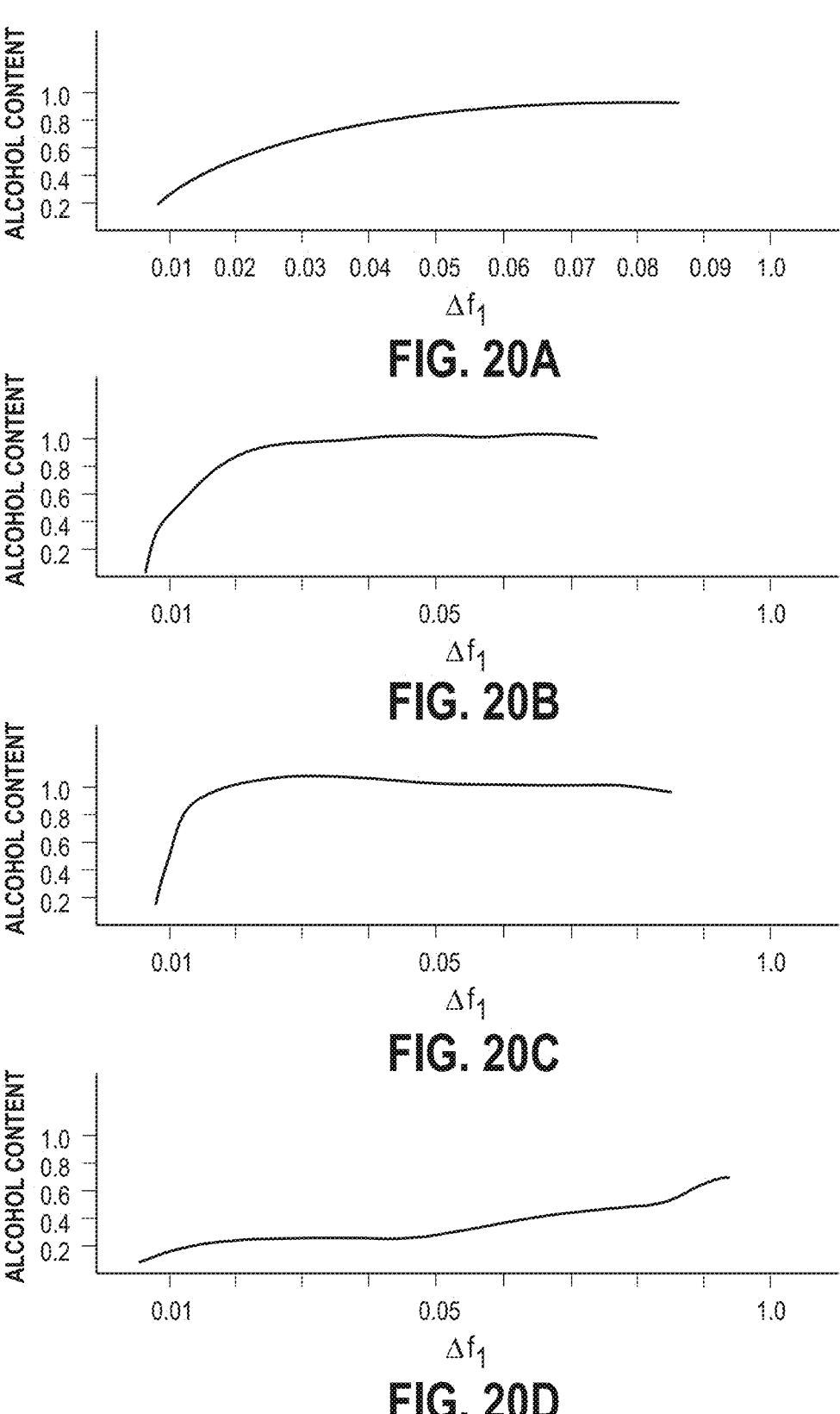
FIGS. 20A-D illustrate exemplary charts of alcohol content as a function of change in frequency.

FIG. 20A illustrates an exemplary chart (or mapping) of an alcohol content of a liquid within a container over a transmitted frequency wherein the transmitted signal frequency is represented as f1. In this exemplary chart alcohol content is represented on a vertical axis and a frequency difference ($\Delta$f1) between a transmitted signal and a return signal is shown on a horizontal axis. As shown, as the alcohol content increases, the expected difference in frequency between the transmitted signal and the return signal increases. Accordingly, a measurement of the frequency difference provides a means for determining an alcohol content of a fluid or liquid within the container.

Accordingly, a measurement of the frequency difference provides a means for determining an alcohol content of a fluid or liquid within the container.

FIG. 20B, FIG. 20C, and FIG. 20D represent charts, similar to the chart shown in FIG. 20A, representing a measure of alcohol content associated with a fluid or liquid for different transmitted frequencies (represented as f2, f3, f4 respectively).

Accordingly, an alcohol content may be determined for each of a plurality of measured frequency returns for each of the selected antenna configurations. Accordingly, an overall alcohol content may be determined based on the collection of one or more alcohol content taken over one or more frequency measurements over one or more antenna configurations.

Although only four (4) frequencies are illustrated, it would be within the knowledge of those skilled in the art to create additional charts showing frequency shift as a function of alcohol content without undue experimentation. As the number of charts similar to those shown in FIGS. 20A-20D is expanded, the accuracy of the measurement of alcohol content would increase as the number in the transmitted frequencies increases.

Although FIGS. 20A-20D illustrate exemplary charts of alcohol content as a function of change in frequency, it would be recognized by those skilled in the art that a similar set of exemplary charts may be obtained as a function of phase change, signal strength change, change in distance and/or time traveled or other similar characteristic associated with the transmitted signal, without altering the scope of the invention claimed.

Figure 21:
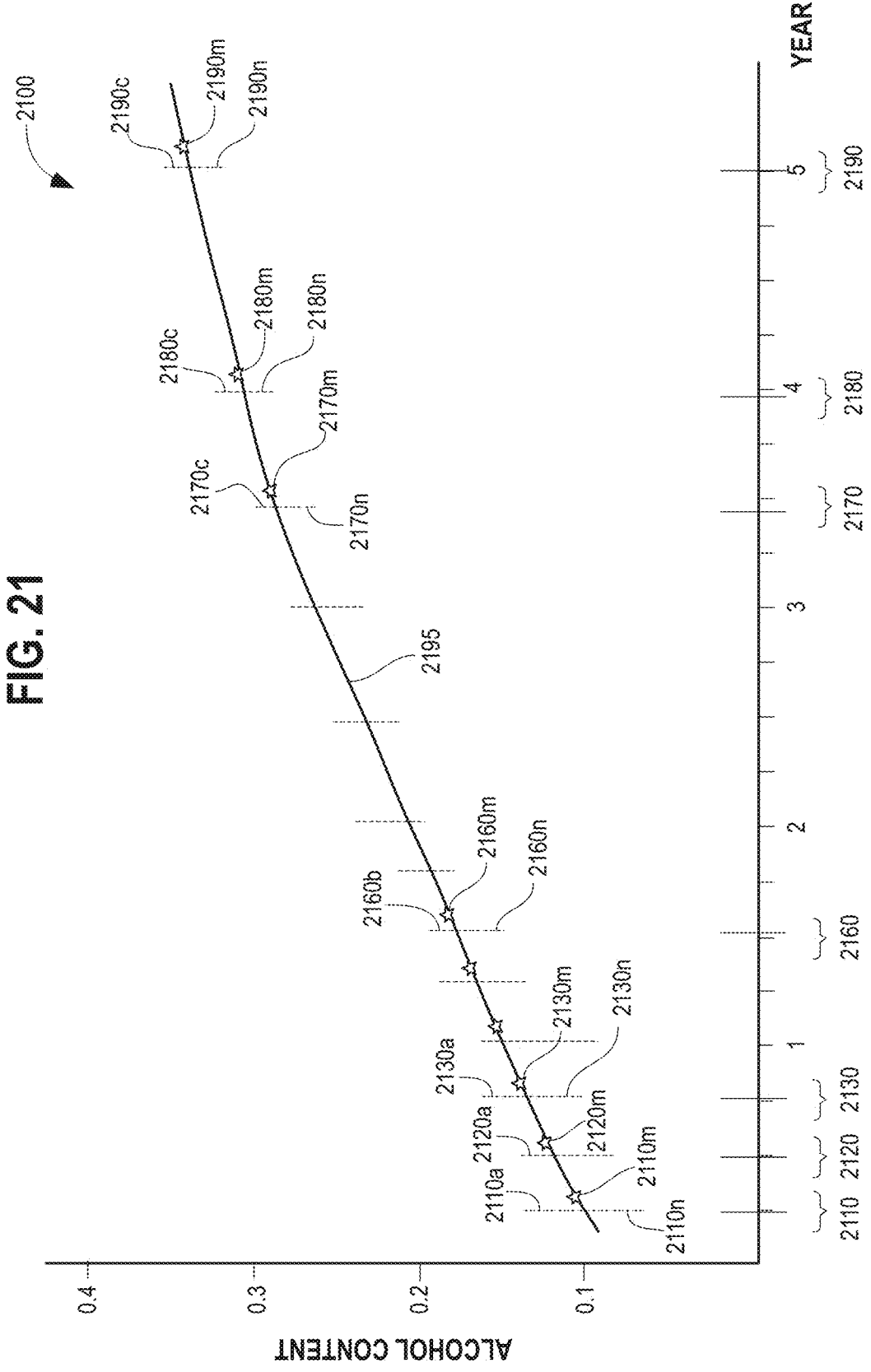
FIG. 21 illustrates an exemplary chart of measurement of alcohol content as a function of time.

FIG. 21 illustrates an exemplary chart of determined alcohol content as a function of time in accordance with the principles of the invention.

In this illustrated example, chart 1500 represents a plurality of measurement sets 2110, 2120, 2130, 2140, 2150, 2160, 2170, 2180 and 2190 that are taken at intervals over a period of time. For example, measurements 2110a-2110n associated with measurement set 2110 represent a measured alcohol content for each of a plurality of antenna 220a-220n (similar to the configurations shown in FIGS. 2, 7A and 7B). In this illustrated example, the value of "n" is selected as eight (8) to illustrate the principles of the invention. Similarly, the measured data points are shown as individual data points linearly spaced apart to show the individual measurements. Generally, it would be expected that one or more measurements or measurement points a-n of any measurement set 2110, 2120, 2130, 2140, 2150, 2160, 2170, 2180 and 2190 may be the same or substantially the same.

In addition, each of the illustrated measurement points 2110a-2110n may represent an accumulated value taken over multiple transmission frequencies (and/or phase) measurements (e.g., frequencies f1, f2, f3, f4, as shown in FIGS. 14A-14D). For example, measurement set 2120 and 2130 represent similar measurements taken, in this illustrated case, at a first known rate (e.g., quarterly) during a first or initial period (i.e., first year).

In accordance with the principles of the invention, an average or median value (i.e., 2110m) associated with measurement points 2110a-2110n of measurement set 2110 may be calculated to determine an alcohol content associated with measurement set 2110. Similarly, median values 2120m, 2130m associated with measurements 2120a-2120n, 2130a-2130n, respectively, may be calculated to represent an overall alcohol content for measurement sets 2120, 2130, respectively. Similar average or median values may be determined for each of the measurement sets 2140-2190.

Accordingly, a median alcohol content for each of the illustrated measurement sets 2110-2190 may be determined and utilized to determine a progression of alcohol content of the liquid or fluid within a container without the need to interrupt the process by taking conventional measurements.

Further illustrated, with regard to measurement set 2160 are measurements 2160b-2160n associated with antenna 220b-220n. In this illustrated example, as evaporation or absorption of the fluid within the container occurs, it may be determined that a signal transmitted by antenna 220a provides no useful information and, thus, a signal from antenna 220a is not transmitted nor included within the calculations of an overall alcohol content (i.e., 2160m). A similar selection of antenna is shown by measurement sets 2170-2190 where signals associated with antenna 220b are neither transmitted nor included within the calculation of overall alcohol content (e.g., 2170m-2190m).

In accordance with the principles of the invention, the measurements of fluid loss (and determination of alcohol content) may be taken concurrently at a first rate (e.g., quarterly) during a first period of time (e.g., first and second year) while subsequent measurements of fluid loss and alcohol content may be taken concurrently at a second rate (semi-annually, annually) during a second (e.g., 2nd and 3rd year, 4th and 5th year) period of time, wherein the second rate is longer than the first rate. That is, the periodicity of the measurement rate (i.e., first rate and second rate) may increase over time.

For example, during a first year, when alcohol production is greatest, measurements may be taken at a first rate (e.g., measurement sets 2110, 2120 . . . 2160) and when alcohol production is less, measurements may be taken at a second rate (e.g., 2170, 2180, 2190), wherein the first rate is higher (i.e., measurements performed more often) than the second rate.

Alternatively, the measurement of fluid loss and alcohol content progression may be taken asynchronously wherein fluid loss may be determined at a fluid loss first and second rate as previously discussed and alcohol content progression may be determined at an alcohol progression first and second rate, wherein the fluid loss rates and the alcohol progression rates are different.

Further illustrated is a statistical formulation of the measured sets 2110m-2190m as represented by dashed plot line 2195. Dashed plot line 2195 represents a model that may be utilized to refine the models shown in FIG. 20A-20D. For example, a plurality of plot lines 2195, taken from corresponding measurements of a plurality of containers that have similar characteristics may be accumulated and included in the model shown in FIGS. 20A-20D.

FIG. 21, similar to FIG. 18, illustrates the variation in the time period between measurements that may occur for the measurement of an alcohol content associated with the processing shown in FIG. 19. As previously discussed, the time period of measurement for alcohol content may occur concurrently with the time period of measurement for fluid level shown in FIG. 18. However, it would be recognized that the time period for alcohol content determination may be different than the time period of measurement for fluid level. Thus, the two processes shown may operate concurrently or independently without altering the scope of the invention claimed.

Various implementations have been disclosed with reference to the Drawings. However, other implementations are possible.

Implementation 1. A method for determining an alcohol content of a fluid within a barrel, the method comprising the steps of: transmitting at least one signal from each antenna within a set of antenna selected from among a plurality of antenna positioned externally to the barrel into the barrel; receiving a response associated with the transmitted at least one signal, determining a change in at least one characteristic between corresponding transmitted at least one signal and the received response; determine a change of a characteristic between the at least one transmitted signal and a corresponding received response; and determine from the determined change in the characteristic an alcohol content of the fluid within the barrel based on a mapping of an alcohol content with respect to the change in characteristic.

Implementation 2. The method of implementation 1, wherein the step of determining a change in characteristic comprises the steps of: accumulating the change in characteristic between each of the at least one transmitted signal and the corresponding received response; and setting the determined change in characteristic as the accumulated change in characteristics.

Implementation 3. The method of implementation 2, wherein the step of determining a change in characteristic comprises the steps of: averaging the accumulated change in characteristic between each of the at least one transmitted signal and the corresponding received response; and setting the determined change in characteristic as the average accumulated change in characteristic.

Implementation 4. The method of implementation 1, wherein the characteristics is selected from at least one of: a signal strength, a frequency shift, and a phase shift.

Implementation 5. The method of implementation 1, wherein the step of determining a change in characteristic comprises the steps of: determining an average value of the change in characteristic for each of the at least one signal for each of the antenna within the set of antenna; determining an alcohol content for each of the average values; and determining an overall alcohol content based on the determined alcohol content for each of the average values.

Implementation 6. The method of implementation 1, comprising: identifying among the plurality of antenna, an antenna positioned within a range of the fluid within the barrel; and selecting the identified antenna as being within the set of antenna.

Implementation 7. The method of implementation 6, wherein the step of identifying comprises the steps of: transmitting from the plurality of antenna, a measurement signal into the barrel; receiving a return signal of the transmitted measurement signal; determining a signal strength of the received return signal, and identifying an antenna associated with a signal strength greater than a threshold value as being within the range of the fluid.

Implementation 8. The method of implementation 1, transmitting at least one signal from each antenna comprises the steps of: transmitting at a first rate during a first period of time: and transmitting at a second rate during a second period of time.

Implementation 9. The method of implementation 8, wherein the first rate is greater than the second rate.

Implementation 10. A system for determination of an alcohol content of a fluid within a barrel, the system comprising: a plurality of antenna positioned external to the barrel; and a transmission/reception system configured to: transmit at least one transmission signal within at least one frequency band from a set of antenna selected from the plurality of antenna; receive a return signal associated with the transmitted at least one transmission signal; and determine a change in at least one characteristic between the at least one transmission signal and a corresponding return signal; and determine from the determined change in the at least one characteristic an alcohol content of the fluid based on a mapping of alcohol content with respect to the change in the at least one characteristic.

Implementation 11. The system of implementation 10, wherein the change in the at least one characteristic comprises at least one of: a signal strength change, a frequency change or a phase change.

Implementation 12. The system of implementation 10, wherein the transmission/reception system is configured to: determine the change in the at least one characteristic as an average of the change in the at least one characteristic over each determined change in the at least one characteristic.

Implementation 13. The system of implementation 10, wherein the transmission/reception system is configured to: determine an average change in the at least one characteristic as: an average value of the change in the at least one characteristic over each of the at least one determined change in the at least one characteristic for corresponding ones of the antenna within the set of antenna; and an average of the average values.

Implementation 14. The system of implementation 10, wherein set of antenna comprises at least one antenna associated with a determined level of fluid within the barrel.

Implementation 15. The system of implementation 14, wherein the system is configured to: transmit a measurement signal into the barrel from an antenna selected from the plurality of antenna; receive a return signal associated with the measurement signal; determine a signal strength of the return signal; and assign, when the signal strength is greater than a threshold value, a corresponding antenna selected from the set of antenna.

Implementation 16. A system for determining an alcohol content of a fluid within a barrel, the system comprising: a plurality of antenna arranged at known locations on a face of the barrel; and a processing system comprising: a transmitting system and a receiving system in communication with each of the plurality of antenna; and a processing system configured to: receive, from the receiving system, information regarding a signal transmitted into the barrel by the transmitting system, wherein the information is associated with the signal transmitted to determine a level of fluid within the barrel and an alcohol content of the fluid within the barrel, wherein a determination of the level of fluid comprises: causing transmission of a measurement signal from each of the plurality of antenna; receiving a response associated with the transmitted measurement signal; and determining at least one factor associated with the received response; and assigning, when the at least one factor is greater than a threshold value, a corresponding antenna to a set of antenna; and wherein the determination of the alcohol content comprises: causing the transmission of at least one signal from each of the antenna within the set of antenna; receiving at least one return signal in response to the transmission of the at least one signal transmission; determining a change in a characteristic between the at least one signal transmission and a corresponding return signal; and determining an alcohol content associated with the fluid within the barrel as a function of a mapping of alcohol content with respect to the change in the characteristic.

Implementation 17. The system of implementation 16, wherein the processing system is further configured to periodically perform the determination of fluid level and alcohol content, and wherein a rate of performance of the determination of fluid level and alcohol content may be the same or different.

Implementation 18. The system of implementation 16, wherein the mapping of alcohol content with respect to change in characteristic is established on an individual transmission frequency basis.

Implementation 19. The system of implementation 16, wherein performance of the determination of alcohol content is performed starting with a lowest positioned antenna within the set of antenna.

Implementation 20. The system of implementation 16, wherein performance of the determination of alcohol content is performed starting with a highest positioned antenna within the set of antenna.

For example, an exemplary method may comprise receiving information regarding an initial state of a liquid in a container, the initial state comprising at least one of: an alcohol measure and a level of the liquid within the container; monitoring a level of the liquid within the container, wherein the monitoring is performed external to the container; determining an alcohol content of the liquid within the container based on the initial level; and estimating the alcohol measure of liquid remaining within the container. In addition, a measure of the loss of fluid in the container may be used to limit the measurements taken to only those configurations that would provide useful information in determining the alcohol content.

The method may further comprise storing a plurality of estimated alcohol measures.

The method may further comprise extrapolating an expected alcohol measure based on the stored plurality of estimated alcohol measures.

Estimating the alcohol measure may further comprise adjusting the estimated alcohol measure based on at least one environmental condition.

The at least one environmental condition may be selected from a group consisting of: temperature, location within a facility, a geographic location of the facility, and container condition.

The determination of estimating the alcohol measure may be performed periodically.

The rate of periodicity estimating the alcohol measure may be adjustable.

The rate of periodicity estimating the alcohol measure may be increased as a function of time.

An exemplary system may comprise a plurality of antennas positioned on an exterior surface of a barrel, wherein the plurality of antennas are configured to capture signals reflected by a liquid within the barrel; and a processor configured to: receive the reflected signals; and determine a change in at least one characteristic of the return signal, wherein based on the determined change in the at least one characteristic an alcohol content may be determined. The processor may be further configured to: determine a loss of liquid within the barrel based on the determined level of fluid and an initial level of fluid; and limit the signal transmission from those antenna that would provide useful information in the estimation of an alcohol content of the liquid within the barrel.

The system may further comprise the processor may be configured to store the estimated alcohol content.

The system may further comprise the processor may be configured to extrapolate an expected alcohol content based on a stored plurality of estimated alcohol measures.

The system may further comprise the processor may be configured to adjust the estimated alcohol content based on at least one environmental condition.

The at least one environmental condition may be selected from a group consisting of: temperature, location within a facility, a geographic location of the facility, and container condition.

The determination of estimating the alcohol content may be performed periodically.

The rate of periodicity estimating the alcohol content may be adjustable.

The rate of periodicity estimating the alcohol content may be adjustable as a function of time.

An exemplary method may comprise: determining, by a monitoring system external to a container, an estimation of an alcohol content of the liquid within the container based on the a determination of one or more characteristic associated with one or more signals transmitted within the barrel, wherein the estimation comprises: determining a change in at least one characteristic at a known frequency (or phase); obtaining a first order alcohol content based on a model expectation of alcohol content at the known frequency (or phase); and determining the alcohol content based on adjusting the first order alcohol content based accumulating a plurality of first order alcohol content associated with different locations of fluid within the barrel or container.

The method may further comprise projecting an estimated alcohol content based on a plurality of the determined alcohol content.

The method may further comprise determining the alcohol content of the liquid within the container periodically, wherein measurements of the alcohol content are performed at a first rate during a first period of time and at a second rate during a second period of time, the first rate being faster than the second rate. The first rate and the second rate of the transmission of signals for the determination of alcohol content may be based, at least in part, as previously discussed with regard to the transmission of signals for the determination of fluid level. For example, the first rate may occur during a first period of time and the second rate may occur during a second period of time. The first rate may be greater than the second rate. For example, during a period of expected rapid change in alcohol content measurement associated with the determination of alcohol content, measurements may occur once/week, whereas during a period of expected slowing of the change in alcohol content, the determination of alcohol content may occur once/month, semi-annually, etc.

It would be understood and recognized that the first and second rates associated with fluid level measurement and alcohol content may be same or different. In addition, it would be recognized that the measurement of fluid level and alcohol content may be performed periodically wherein the period of measurement of fluid level and the period of determination of alcohol content may be the same or different. That is, fluid level measurement and alcohol content measurement may be performed at the same time and the same rates. Alternatively, fluid level measurement and alcohol content measurement may be performed at different times and at different rates.

In summary, the presented invention, provides for the determination of alcohol production progression during the distilling of an alcohol based liquid within a container without causing any interference with the alcohol production by the need to physically test the liquid, wherein the measure of alcohol with the container is based on a system that may be attached to a face of a container, that causes the transmission of one or more signals in at least one frequency range into the container, where the transmitted signals that are reflected off the fluid or liquid contained within the container are captured and evaluated to determine a level of the fluid or liquid within the tank. A measure of the alcohol content is then based on the determination of the loss of fluid or liquid.

The system disclosed achieves technical advantages over the prior art as the invention disclosed remains external to the enclosed system (barrel, etc.) and does not affect the internal ecosystem or contents of the barrel.

In addition, a method associated with the present invention is disclosed, wherein the method comprises the steps of: transmitting at least one signal into the tank; receiving a response associated with selected ones of the transmitted at least one signal; and evaluating the received response associated with selected ones of the transmitted at least one signal, wherein the evaluation comprises: determining a signal strength of each of the received response; selecting at least two of the received responses, wherein the selected responses are associated with a highest signal strength; and determining the fluid level based on a relationship between the selected at least two of the received responses.

In addition, a method associated with the present invention is disclosed wherein the method comprises the steps of: obtaining an initial alcohol content and level of a fluid within a container and obtaining measurements of the fluid level over time to evaluate and determine a loss of fluid due to one of evaporation and absorption, computing an expected alcohol content based on the initial alcohol content and the loss of fluid and further adjusting the expected alcohol content by one or more environment factors associated with at least the conditions surrounding the storage of the fluid.

Although various features have been described with reference to the Figures, other features are possible. For example, a device implementation in accordance with the present disclosure may comprise modular units with a varying thickness print flex antenna across a barrel face. The device may be implemented with a custom-designed PCB motherboard configured to be mounted in the middle of the barrel face. The device may comprise radar and radio frequency chips and a separate data transceiver module. The data transceiver module may be configured to operate using BLUETOOTH, LORAWAN or another band protocol. The device may be configured with a defined power source, for example a C1, D2 certified single core battery. The device may be attached to the face of an enclosed system (e.g., a whiskey barrel) with the printed antenna arrays located with reference to a defined position of a watch/barrel face. The antenna arrays may be located with reference to the center point of the watch/barrel face. The devices may be adhered or attached to the barrel face with an adhesive or attached with composite fasteners (screw/nail/staples, or the like).

The device may be configured to use a combination of Millimeter Wave (MM Wave) and or Radio Wave (RF), and/or other direct analog measurement methodologies to determine the liquid substrate level behind a barrel face. Liquid-level measurements may be relayed to multiple central communications hubs via BLUETOOTH, LORAWAN or any other communications technology, depending on the distance from the barrel to central device. From the central device, measurement data may be exported out of the rickhouse via satellite, cellular, or fiber connection to the cloud or a handheld device. A device implementation deployed on a barrel may be configured to broadcast measurement data packets from the barrel to the central device and from there exported out of the rickhouse via satellite, cellular, or fiber connection to the cloud or a handheld device configured to collect the measurement data packets exported from the central receiving device.

The device implementation may be configured to account for the introduction of foreign bodies or materials such as wooden staves, woods chips, or anything else that would displace the liquid level. For example, software may be configured to account for the displacement measurement and the displacement differential of any object inserted into the liquid to maintain an accurate measurement. In an illustrative example, the displacement and/or differential measurement software implementation may have a foreign body displacement measurement mode that determines displacement differential between liquid levels measured at different points in time, that is, before and after a foreign body is introduced to the container. The device implementation may incorporate the use of RFID to connect the device to software to track the device/barrel location in a "rickhouse."

The device implementation may use MM Wave, RF Wave, or another lower frequency or band as needed. This radar may be a low enough frequency (e.g., <10 GHZ) to ensure penetration of the wood. The signal that is transmitted into the barrel by the antenna would be reflected back at levels where the liquid is present, in contrast with no reflections from levels where the liquid is not present. This group of reflections and non-reflections produces a total measured signal that is processed by the device to determine an estimate of the height of the liquid-air interface.

In an illustrative example a device implementation may be configured to determine liquid level measurements in a horizontal rick storage mode. For example, a horizontal rick storage mode implementation may be configured to measure the liquid level over time as it relates to where any substrate is in contact with the barrel face as well as the liquid-air interface. Such an implementation will be able to determine fluid volume at any given period. Distillers are required by law to log exactly how many proof gallons they put into any barrel at any time. The device implementation may be calibrated by inputting the exact amount of whiskey/tequila/spirits/etc. (substrate) reported to all required international governmental agencies on to the device, permitting the device to measure the differential of evaporation over time (AKA "The Angels Share"). In an illustrative example, the device implementation can then determine loss over time based on how antennas read the liquid-air interface behind each antenna. In this example implementation, the device is directly measuring the difference in liquid level between points of a varying printed antenna design as well as any liquid-air gaps in the antenna array which may vary in size and orientation.

In another illustrative example, a device implementation may be configured to determine liquid level measurements in a vertical palletized storage mode. For example, a vertical palletized storage mode implementation may be configured to measure the reflection between the waves as it pertains to liquid content of an aging barrel. In this mode, one or more antennas will reflect waves downward through the barrel face and measure the reflection time between device and barrel, device and substrate, device and barrel bottom, as well as any materials inserted or placed in the barrel. This measurement may calculate the distance and relative length of the wave and convert that measure into an accurate measure of substrate. Some waves will go through the barrel and never return and will be disregarded. The device may be configured to only interpret what the device knows as operative space and measure total volume.

The device implementation may be a combination of a peel and stick design and/or with a potential non-metal/composite screw/staple/nail or fastening device that would allow distillers to adhere/attach the device to the barrel face at the time of barrel fill.

During barrel fill, distillers are required by the law to exactly track and log the amount of liquid put in the barrel, as stated above. All barrels may not be filled to the same fill level or amount. Accordingly, one or more calibration steps may be performed, as described herein. Connecting the device to the barrel and the system may benefit from calibration to ensure correct and accurate measurements. In an illustrative example, a software application may be configured to uniquely associate the barrel to the device for the barrel's primary lifespan (these could be sent to a secondary market). For example, a unique hardware identifier for a barrel may be associated in a database with a unique identifier for an instance of the measurement device disclosed herein. In such an example, particular calibration data determined for the barrel/measurement device pair may be uniquely associated with the measurement device in the database, permitting the calibration and measurement performance of the device to be tracked over time.

As these "rickhouse" environments are quite harsh, a very strong adhesive or other fastening device may be used to adhere/attach the device to the barrel face in both horizontal (traditional rick storage) and vertical (palletized) storage options. In some aspects, the PCB board and all of the components may be encased in a strong epoxy resin potting material or other hard casing to protect all electronics from any potential damage. Damage could be from forces like bumps, scrapes, dings, whiskey leaking on top, and/or heat and/or humidity.

Once the barrel is filled and calibrated, the device is capable of providing a near absolute liquid level measurement. Barrels may range in total volume (the industry average is a 53-gallon barrel, which will vary in finished size). Barrels can be filled above 53 gallons. In an illustrative example, the device may adhere/attach to the barrel face in the same fashion regardless of barrel size or storage options such as horizontal rick storage and palletized storage. Antenna arrays can vary in size and orientation based on the size of the barrel face as the barrels vary in total surface volume.

After filling, barrels may be moved to their storage locations where they will sit for varying periods of time. Because of this, the device design may comprise a single-core ATEX-certified battery system, which may provide a potential life span between 6 and 10 years. In an illustrative example, the device may be configured to satisfy a fire safety class 1 div 2 classifications according to DISCUS, NEC, and ATEX class 2. Keeping fire safety in mind, the single-core battery may be used because the single-core battery traditionally has a slower discharge rate than reusable or rechargeable batteries. The device may be configured to ping only once a month, every month for the life span of the device or barrel, to conserve battery energy.

The device may be configured to be in communication with a central receiver. The central receiver may be configured in communication with other sensors, such as ambient temperature and/or humidity. Once the device is pinged from the central receiver, the device will activate; once activated, the device programming will cause the device to follow distinct operation sequences for horizontal storage and palletized storage device implementations.

In an illustrative example a device implementation designed for a horizontal storage mode in a traditional rickhouse may be configured to perform operations comprising: the device will activate an RF signal which goes across the antenna array; the device will measure exactly the differential of what is behind the barrel head and any relation to the space liquid-air differential between antennas across the clock face of the barrel and the device; as well as the relation of what's behind the wood to our antenna array will allow for volume measurement.

In an illustrative example, a device implementation designed for a palletized storage mode may be configured to perform operations comprising: the device will activate in a similar manner as the horizontal storage mode implementation but rather with an MM signal. The device will fire, or send, one or more waves downward and register the wavelength and reflection between the device, barrel face, liquid, barrel bottom, and any particulate inside the barrel; the device will then interpret the total space of liquid contained, and a measurement will be calculated.

In some aspects, measurements may be saved in a platform for the distiller or end user to make both qualitative and quantitative inferences. These qualitative and quantitative inferences may be used to calculate predictions for Barrel Yield, Tax Planning, Barrel Provenance, and Supply Chain planning.

If a distiller can understand exactly where their total run volume stands more accurately than current industry models of 2-4% loss per year they can make better decisions and inferences on metrics such as barrel performance as it relates to the quality of a cooperage (barrel maker), how any potential variable may affect a barrel such as heat, humidity, any coating material or R&D experiment. Knowing the volume of barrel can allow distillers to make many decisions to both increase efficiency and reduce industrial waste.

Another value add is that with the accurate volume, distillers can work with their insurance provider to reduce potential premiums as well as make sure that they are neither under-insured nor over-insured. They would just be adequately insured for loss.

Potential Yield: In the pursuit of optimizing production, distilleries need to and want to accurately gauge the volume of whiskey in each barrel. This not only helps in maximizing the yield from each batch but also in efficiently utilizing resources. Precise measurements allow for better supply chain forecasting and planning, ensuring that each step of the distillation and aging process is conducted with the utmost efficiency. Also helping with yield as it pertains to number of bottles and cases for their distributors.

Tax Planning: The taxation on distilled spirits can be complex, and it's based, in part, on the volume of product produced and stored. Accurate barrel measurements are essential for distilleries to comply with tax regulations accurately. This precision helps avoid over or underpayment of taxes, which can have significant financial implications. By knowing exactly how much whiskey is in each barrel, distilleries can file more accurate tax returns, thus avoiding potential legal and financial issues. There are major benefits to knowing your PGs (proof gallons) as tax rates do change from around $2.85 and $13.25 once a distillery crossed a set limit (100,000 PGs or roughly 1886 barrel) taxes increase.

Provenance: from its distillation to its aging—knowing volume and history adds to the product's allure and value consumers will pay. Precise barrel measurement contributes to the detailed tracking of each batch's journey, ensuring that the provenance is well-documented and authentic. This level of detail enriches the narrative of the whiskey, providing whiskey enthusiasts with a deeper appreciation of its heritage and quality.

The device may be implemented with a flex tail antenna array that will cover the clockface or in a wagon wheel design of a whiskey barrel that is adhered by a durable adhesive or composite fastener. RF and MM wave chips may be used to determine the liquid levels. The device may include a fire safety approved battery. The device may be configured with multiple interfaces to push data both into and out of the device. The device may be encased in a hard epoxy potting or protective casing. The device may be configured with BLUETOOTH, LORAWAN or another communication band to carry data in and out of the device.

In some embodiments, the device remains external to the barrel and does not impede the aging process. The device may reduce labor cost over handheld devices and is more accurate. The device is also on the face of the barrel; thus, the barrel can be rolled without the device having to be removed.

In some embodiments, an artificial intelligence driven whiskey analyzing system can use an artificial intelligence (hereafter referred to as "AI") powered, non-invasive barrel monitoring system to prevent inefficiency by using radar-based volume tracking, dielectric proof sensing, and machine-learning color analyzation to provide real-time whiskey aging insights without opening barrels. In some embodiments, the aging determinations and compliance measurements obtained by the AI-driven system can be more accurate, automated, and scalable, as a result of integrated AI, radar, and sensor technology design that analyzes environmental conditions, evaporation rates, and proof fluctuations continuously. The AI-driven whiskey monitoring system can be used in distilleries, spirits manufacturing, and regulatory agencies for producing higher-quality, consistent, and efficiently taxed whiskey while reducing waste and optimizing aging strategies.

In some embodiments, the AI-driven whiskey analyzing system can integrate radar-based liquid volume tracking, dielectric proof sensing, and AI-driven analytics into a non-invasive, real-time system that eliminates the need for manual sampling. The AI-driven whiskey analyzing system can be configured to detect barrel aging conditions through sensor inputs. These inputs can comprise of radar-based frequency-modulated continuous wave (FMCW) signals which can penetrate the wooden barrel to measure liquid volume changes accurately over time. These inputs can also include a dielectric-based sensor array configured to detect fluctuations in ethanol concentration (proof) by analyzing electromagnetic permittivity within the barrel substrate. These inputs can include temperature and humidity sensors configured to collect environmental data affecting whiskey aging.

In some embodiments, the AI-driven whiskey analyzing system can be configured to include processing the detected data using an AI-driven model. As an example, the processed data can include volume, proof, temperature, and/or humidity data with an AI-trained analyzation aging model. The processing can include using a machine-learning (hereinafter referred to as "ML") model, such as convolutional neural networks (hereinafter referred to as "CNN") and long short-term memory (hereinafter referred to as "LSTM"), that may analyze historical and real-time barrel data to forecast whiskey color evolution over time. The processing can use AI to correlate whiskey evaporation trends with proof adjustments to ensure compliance with regulatory taxation standards.

In some embodiments, the AI-driven whiskey analyzing system can be configured to include triggering automated aging optimization and compliance actions. The AI-driven whiskey analyzing system can be configured to generate a digital twin of barrel aging conditions, enabling distilleries to make real-time, AI-driven decisions on aging, blending, and bottling. For example, the actions can include a compliance automation module that may generate tax-ready reports that match regulatory requirements (e.g., TTB standards). In some embodiments, the system can alert operators if a barrel has reached optimal maturation based on AI-driven analyses, preventing over-aging or premature bottling.

In some embodiments, the CNN-LTSM hybrid system can use time-series aging trends and spectrophotometric features to forecast color evolution non-invasively. In some embodiments, the machine-learning system can use reinforcement learning to perform proof calibration. The proof calibration can adapt dielectric permittivity models to environmental fluctuations to ensure real-time ethanol concentration tracking. In some embodiments, the machine-learning system can use Gaussian process regression for barrel evaporation. The Gaussian process regression can compensate for warehouse-specific evaporation rates and can improve proof measurement accuracy. In some embodiments, the machine-learning system can use autoencoder-based anomaly detection for tax compliance to detect fraud risks and underreported whiskey losses.

In some embodiments, the AI-driven whiskey analyzing system can include an ML model that can calibrate dielectric ethanol concentration tracking based on changes in temperature and humidity. In some embodiments, the Gaussian process regression (hereinafter referred to as "GPR") can be configured to model nonlinear correlations between whiskey proof fluctuations and barrel evaporation rates. In some embodiments, the adaptive ML can be configured to compensate for barrel variations (wood grain, char level, warehouse location).

In some embodiments, the AI-driven whiskey analyzing system can include a monitoring system configured to include a radar-based volume detection module. For example, the radar-based volume detection module can be configured to emit FMCW radar signals into a sealed wooden barrel. The module can also be configured to receive signal reflections and process liquid volume changes inside the barrel without physical contact. The module can also be configured to generate real-time volumetric loss data indicative of evaporation trends (i.e. Angel's Share). In some embodiments, the radar-based volume detection module can apply adaptive signal filtering algorithms to compensate for interference caused by barrel char thickness and wood grain variability.

In some embodiments, the AI-driven whiskey analyzing system can include a dielectric-based proof monitoring module. For example, the monitoring module can be configured to detect ethanol concentration (proof) within the barrel using dielectric permittivity measurements of the substrate. The monitoring module can also be configured to calculate real-time fluctuations in proof due to evaporation without requiring sample extraction. The monitoring module can also be configured to generate continuous proof-tracking data to ensure compliance with regulatory standards. In some embodiments, the dielectric-based proof monitoring module can dynamically adjust ethanol concentration calculations based on real-time temperature and humidity variations.

In some embodiments, the AI-driven whiskey analyzing system can include a CNN model and/or an LSTM model trained on historical whiskey aging data. The CNN and LSTM models can include an input interface to receive time-series data from radar, dielectric, temperature, and humidity sensors. The CNN and LSTM models can also include a processing engine configured to analyze future whiskey color evolution and optimal maturation timelines based on proof, volume, and environmental conditions.

In some embodiments, the AI-driven whiskey analyzing system can include a compliance automation module. The compliance automation module can be configured to generate automated tax compliance reports in accordance with Alcohol and Tobacco Tax and Trade Bureau (TTB) standards. The compliance automation module can also be configured to log real-time proof, volume, and aging adjustments in a secure digital ledger. The compliance automation module can also be configured to provide regulatory audit-ready reports to distilleries and government agencies. In some embodiments, the compliance automation module can implement a blockchain-based verification system for secure storage of tax compliance data. In some embodiments, the compliance automation module can implement a real-time anomaly detection algorithm to identify potential discrepancies in reported proof and volume data. In some embodiments, the compliance automation module can implement an auto-generated regulatory filing system that directly submits compliance reports to government agencies.

In some embodiments, the AI-driven whiskey analyzing system can include a remote monitoring interface. The remote monitoring interface can include a cloud-based platform for distillery operators to visualize real-time whiskey aging conditions. The remote monitoring interface can include an alert system that triggers notifications when a barrel has reached optimal aging, proof changes beyond a threshold, or unexpected evaporation occurs. The remote monitoring interface can also include an API for integrating with third-party distillery management systems. In some embodiments, the remote monitoring interface can integrate with Internet-of-things (IoT)-enabled warehouse sensors to optimize barrel placement. In some embodiments, the remote monitoring interface can provide real-time analytics dashboards for monitoring multiple aging warehouses. In some embodiments, the remote monitoring interface can allow distillery operators to remotely adjust storage conditions based on AI-driven recommendations.

In some embodiments, the AI-driven whiskey analyzing system can include an AI-driven whiskey aging analyzing module. The whiskey aging analyzing module can be trained on historical distillery datasets of color change trends, configured to use machine-learning feature selection to identify correlations between aging conditions and whiskey hue evolution, and configured to analyze a future color profile based on proof, volume, and storage conditions.

The AI-driven whiskey analyzing system can include integration of IoT, AI, and blockchain into one platform. In some embodiments, the IoT devices can collect raw data on spirits volume, the AI can process this raw data to generate actionable insights, and the blockchain can log each piece of verified data and key event in an immutable record. The AI-driven whiskey analyzing system can include smart IoT sensors on the face of whiskey barrels (and potentially storage tanks) and be configured to continuously measure liquid volume, alcohol content, and environmental conditions in real time. In some embodiments, data from these devices is analyzed by AI to detect anomalies (such as leaks or theft) and to forecast yields. In some embodiments, the system can include an immutable blockchain ledger securely recording each reading. In some embodiments, the recording can be conducted with respect for distillery privacy and business continuity. In some embodiments, the system can be configured to produce a transparent, tamper-proof record of spirits production and aging that can be shared with industry and regulators alike.

The AI-driven whiskey analyzing system can include a network of IoT devices configured to be attached to each barrel face (e.g., underneath the chime). In some embodiments, the IoT devices are equipped with sensors to measure key metrics such as liquid volume, temperature, humidity, and alcohol proof. In some embodiments, an IoT device can be configured to continuously transmit data via a secure wireless connection to a central cloud platform.

The AI-driven whiskey analyzing system can include utilizing the data from IoT sensors with an AI-driven analytics platform. In some embodiments, the AI can be used for forecasting trends and detecting anomalies. In some embodiments, the system can be configured to use machine-learning models to analyze natural evaporation rates and yields for each barrel. In some embodiments, the machine-learning models can be trained on historical maturation data, weather patterns, and barrel wood characteristics. In some embodiments, the AI platform can be configured to monitor the incoming sensor data in real time to flag any irregularities.

The AI-driven whiskey analyzing system can be configured to cross-verify reported figures. In some embodiments, the cross-verification can start when a distiller prepares a tax submission. In some embodiments, the cross-verification can include automatically comparing the declared output against sensor-recorded output. In some embodiments, the cross-verification can include catching any discrepancies before they become compliance issues. In some embodiments, the system can be configured to analyze and identify which warehouse conditions yield the least evaporation or which barrels are outperforming others in preserving volume.

The AI-driven whiskey analyzing system can include recording on a blockchain ledger data and transactions. In some embodiments, this recording can include volume readings, alerts, and important events (e.g., a barrel being filled, moved, or opened for bottling). In some embodiments, the recordings can be encrypted and logged as a blockchain transaction. In some embodiments, the blockchain ledger can be configured to create an automated audit trail.

In some embodiments, the AI-driven whiskey analyzing system can include a computer-implemented method for monitoring and optimizing whiskey aging. The method can include receiving real-time sensor data, including radar-based volume readings, dielectric based proof measurements, and environmental conditions. The method can also include processing the received data using an AI-driven analyzing model. The processing can be configured to determine current whiskey aging parameters, analyze future color evolution based on time-series data, and optimize barrel storage conditions for yield maximization. In some embodiments, the method can include generating automated compliance reports. The reports can include volume loss adjustments for tax filing, proof fluctuation records, and regulatory audit-ready logs for government agencies. In some embodiments, the method can include triggering actionable insights. The actionable insights can include alerts for optimal aging readiness, notifications for unexpected evaporation losses, and recommendations for blending and bottling decisions.

In some embodiments, the AI-driven whiskey analyzing system can use an ultrasonic transducer to measure liquid volume inside the barrel by detecting sound wave reflections. In some embodiments, the AI-driven whiskey analyzing system can include near-infrared (hereinafter "NIR") sensors to analyze alcohol content. In some embodiments, the AI-driven whiskey analyzing system can allow for color to be measured via extracted samples using UV-Vis spectroscopy. In some embodiments, the AI-driven whiskey analyzing system can include systems to simply log temperature and humidity data without modeling to analyze optimal aging durations. In some embodiments, the AI-driven whiskey analyzing system can include spreadsheets, datases, and/or regulatory filing software.

In some embodiments, the AI-driven whiskey analyzing system can use dielectric property changes to track ethanol concentration (proof) inside the barrel without invasive sampling. In some embodiments, ultrasonic sensing can be used for proof estimation. In some embodiments, the ultrasonic technologies can detect liquid density changes, which could be correlated to proof levels. In some embodiments, an external optical system can be used to track changes in the refractive index of whiskey, which correlates with ethanol content, but this would require light penetration into the barrel. In some embodiments, vapor phase ethanol sensors can be used to estimate proof based on the concentration of ethanol in the barrel's headspace.

In some embodiments, ultrasonic level sensors can be used measure liquid height in the barrel. In some embodiments, pressure sensors can be used to estimate volume by tracking pressure changes at the barrel base, but this would require physical modifications to barrels. In some embodiments, capacitive sensors can be used to detect liquid presence by measuring electrical capacitance; in some aspects, the use of capacitive sensors may be less precise than radar in wooden barrel environments.

In some embodiments, the AI-driven whiskey analyzing system can use IoT-enabled temperature & humidity sensors to track warehouse conditions affecting aging rates. In some embodiments, infrared temperature sensors can be used to monitor warehouse temperature distribution. In some embodiments, the AI-driven whiskey analyzing system can use direct control over temperature & humidity through automated HVAC systems to provide an optimized aging environment.

In some embodiments, the AI-driven whiskey analyzing system can provide real-time monitoring & automated alerts when a barrel reaches optimal aging conditions. In some embodiments, the AI-driven whiskey analyzing system can be configured to generate weekly or monthly reports, but this would delay optimization decisions. In some embodiments, the AI-driven whiskey analyzing system can be configured to calculate an aging duration based on sensor inputs to maximize whiskey quality and yield. In some embodiments, the AI-driven whiskey analyzing system can use a predefined set of aging rules. In some embodiments, the AI-driven whiskey analyzing system can be configured to allow distillers to input desired outcomes manually rather than relying on AI learning.

In some embodiments, the AI-driven whiskey analyzing system can include a method for monitoring and tracking a distilling liquid. The method can include monitoring a distilling liquid with at least one sensor. The method can include collecting at least one distilling data point from the at least one sensor. The method can include receiving and analyzing the at least one distilling data point via an artificial intelligence model. The method can include determining via the artificial intelligence model at least one distilling characteristic of the distilling liquid. The method can include transmitting the at least one distilling characteristic to a user.

In some embodiments, the distilling data point can be at least one of a volume, a color, a proof, a temperature, a humidity, and an evaporation rate. In some embodiments, the at least one sensor can be at least one of a radar sensor, a dielectric sensor, an ultrasonic transducer, an environmental sensor, a near infrared sensor, and an ultraviolet-visible sensor. In some embodiments, the method can include tracking the at least one distilling data point and the at least one distilling characteristic. In some embodiments, the method can include comparing the at least one distilling data point and the at least one distilling characteristic, via the artificial intelligence model, against a user-input dataset. In some embodiments, the method can include calculating an optimal aging duration and a bottling time via the artificial intelligence model.

In some embodiments, the method can include alerting the user that the distilling liquid is in an ideal aging window, wherein the ideal aging window is in the user-input dataset. In some embodiments, the method can include determining a distilling recommendation for an optimal aging time and a yield improvement via the artificial intelligence model. In some embodiments, the method can include transmitting the distilling recommendation to the user. In some embodiments, the distilling liquid is contained within a barrel. In some embodiments, the at least one sensor can be a noninvasive sensor. In some embodiments, the method can include tracking at least one of the volume, the proof, and an evaporation loss of the distilling liquid. In some embodiments, the method can include generating a compliance report via the artificial intelligence model. In some embodiments, the method can include transmitting the compliance report to the user.

In some embodiments, the AI-driven whiskey analyzing system can include an apparatus for monitoring and tracking a distilling liquid. The apparatus can include at least one sensor configured to measure at least one distilling data point of a distilling liquid. The apparatus can include a computing device configured to receive the at least one distilling data point from the at least one sensor and analyze the at least one distilling data point via an artificial intelligence model. In some embodiments, the artificial intelligence model can be configured to determine at least one distilling characteristic of the distilling liquid. In some embodiments, the artificial intelligence model can be configured to track the at least one distilling data point and at least one distilling characteristic.

Figure 22:
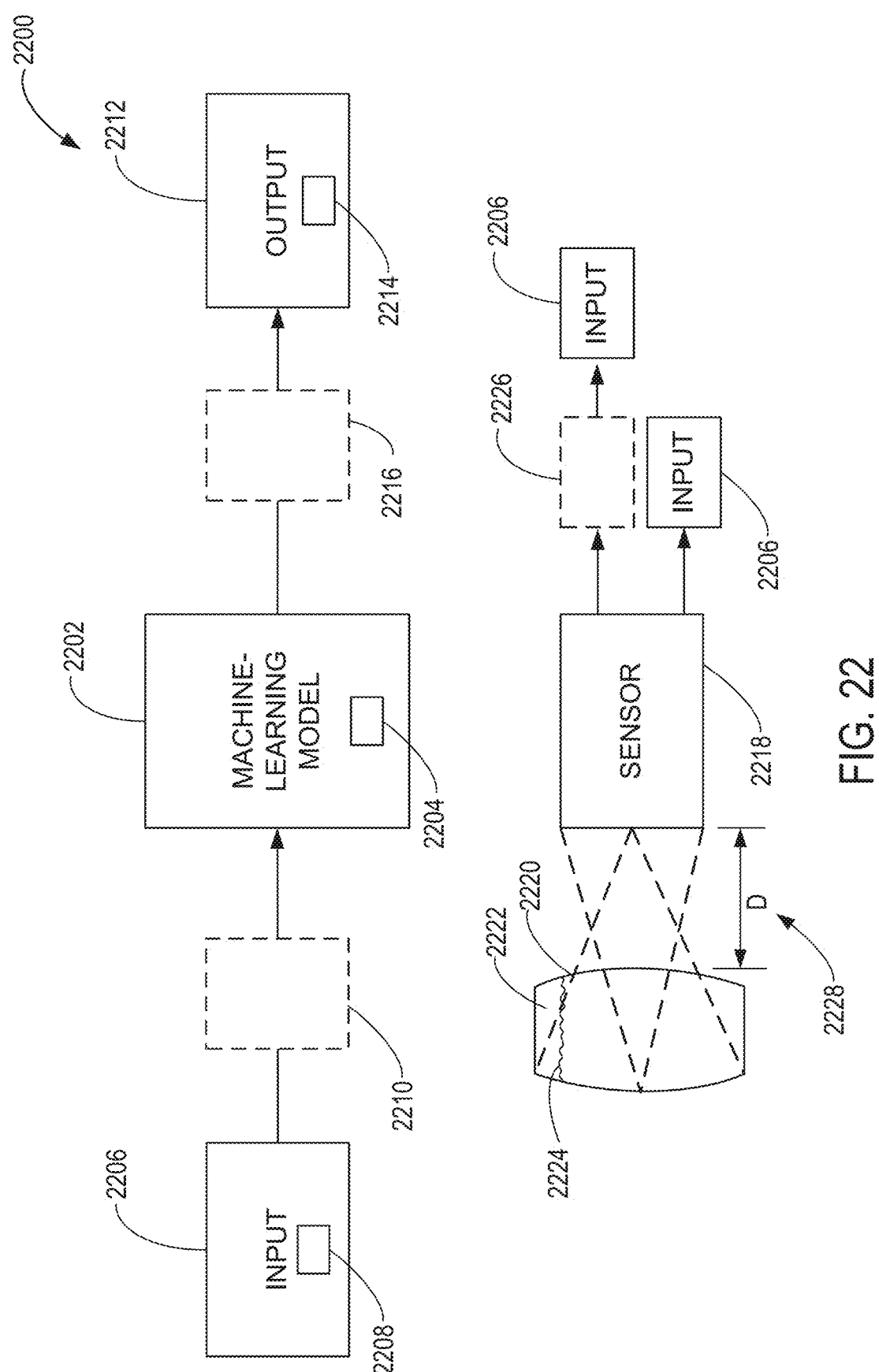
FIG. 22 is a block diagram illustrating an AI-driven system for analyzing a distilling liquid.

FIG. 22 illustrates an exemplary embodiment of an AI-driven monitoring system 2200 for analyzing a distilling liquid in accordance with the principles of the invention. In some aspects, the AI-driven monitoring system 2200 may be configured to gather input data 2206 from one or more sensors, process that data using a machine-learning model 2202 (which may include or be implemented as a neural network 2204), and generate output data 2212 indicative of at least one distilling characteristic 2214. Optional preprocessing 2210 and additional processing 2216 steps may be included to enhance data quality and provide refined results. In some aspects, the AI-driven monitoring system 2200 facilitates real-time or near-real-time analysis, providing insights such as distillation completion, purity levels, or other compliance-related parameters.

In some aspects, the AI-driven monitoring system 2200 may provide an integrated environment for capturing, analyzing, and acting upon data related to a distilling process. In certain embodiments, the AI-driven monitoring system 2200 may include hardware and software configured to execute machine-learning algorithms, store sensor readings in memory, and output predictions or recommendations to an operator or automated controller. The AI-driven monitoring system 2200 may be structurally similar to other apparatuses as previously described herein, wherein at least one sensor may detect parameters associated with a distilling liquid, and processors run inference routines through a trained model. In some aspects, and depending on the implementation, the AI-driven monitoring system 2200 can be deployed in a local setting, such as on a single board computer within a distillery, or distributed across a cloud environment for remote monitoring and control. The AI-driven monitoring system 2200 may work with various sensor types, including radar, ultrasonic, or dielectric sensors, to capture a wide range of data points (e.g., temperature, alcohol proof, color, evaporation rate, etc.). Once processed, the predictions or analyses generated by the AI-driven monitoring system 2200 can guide operational decisions, such as adjusting heating elements, altering flow rates, or halting distillation upon reaching a targeted proof or completion criterion.

In some aspects, the machine-learning model 2202 is configured to receive input data 2206 and generate an analytical or predictive output (e.g., distilling characteristic 2214). The machine-learning model 2202 may be implemented using various architectures, including neural networks, Gaussian process regressions, or hybrid networks. In some aspects, the machine-learning model 2202 can be trained on historical or real-time datasets that contain measurements of temperature, pressure, pH, color, and other relevant attributes of the distilling liquid. A training process may involve adjusting model parameters until the machine-learning model 2202 can accurately associate input patterns with corresponding outputs, such as a completion state or expected purity. The machine-learning model 2202 may run on specialized hardware (e.g., GPUs) or general-purpose processors during operation. In certain implementations, the machine-learning model 2202 can adapt over time via incremental learning, allowing it to refine predictions based on newly acquired sensor data. This adaptability helps address variability in distilling processes caused by environmental changes or equipment conditions.

Neural network 2204 may be similar to or included within machine-learning model 2202, providing a specific type of data-driven architecture well suited for complex pattern recognition tasks. In one embodiment, the neural network 2204 may utilize multiple hidden layers composed of interconnected nodes (neurons) that process input data 2206 via weighted transformations. These weights may be refined through training on historical data, such as temperature curves, reflectance measurements, or flow rates, allowing neural network 2204 to learn nuanced relationships that may govern the distillation process.

In some aspects, the neural network 2204 may employ convolutional layers if the input includes image-like sensor data (e.g., spectral images) or recurrent layers (e.g., LSTM) when dealing with time-series data (e.g., changing temperature over time). Activation functions, such as ReLU or tanh, can introduce non-linearities, improving the network's ability to capture complex trends. Depending on the application, the neural network 2204 can operate in real-time to generate outputs for immediate process control or run in batch mode for offline analysis. Accordingly, the neural network 2204 may translate raw sensor signals into actionable metrics, thereby enhancing the precision and reliability of the AI-driven monitoring system 2200.

Input data 2206 represents the raw or partially processed measurements fed into the machine-learning model 2202. This data can originate from various sensor types, including radar, dielectric, ultrasonic transducers, environmental, near-infrared, or ultraviolet-visible sensors. In some aspects, each sensor may capture different aspects of the distilling liquid, such as volume, temperature, pH, color, or alcohol concentration. Input data 2206 can also incorporate metadata, for example, time stamps or batch identifiers, enabling the machine-learning model 2202 to track changes and detect trends over extended periods of time. In some embodiments, input data 2206 may be processed locally on a sensor node before being transmitted to the AI-driven monitoring system 2200.

Alternatively, or in addition, input data 2206 may be aggregated and stored in a centralized location for batch analysis. Additional information, such as environmental humidity or equipment calibration data, may enhance predictive accuracy. By capturing a comprehensive snapshot of distillation conditions, input data 2206 can provide a foundation for the predictive capabilities of the machine-learning model 2202 and drive decision-making processes within the AI-driven monitoring system 2200.

At least one data point 2208 associated with a distilling liquid encompasses the specific measurements drawn from the broader set of input data 2206 that correspond to a distilling liquid's characteristics. This data point may be reflective of properties such as, but not limited to, temperature, pressure, pH, alcohol proof, or a spectral measurement indicative of color or composition. A radar sensor may generate a waveform or reflection measurement in some aspects, while a near-infrared sensor captures absorption spectra. Such data points provide the machine-learning model 2202 with quantitative or qualitative indicators of the liquid's state, enabling inferences about distillation completion or potential impurities. Depending on the system's hardware configuration, multiple data points 2208 can be captured in parallel or sequentially. In some aspects, an apparatus or method of handling these data points may allow for real-time streaming into the neural network 2204, offline batch processing, or intermediate storage for future retrospective analysis. Data point 2208 can provide an input set for the machine-learning model 2202 by covering a wide range of potential measurements. Accordingly, data point 2208 may result in greater predictive power and finer control over the distillation process, whether for whiskey or other spirit production.

Optional pre-processing 2210 may refine or condition input data 2206 before feeding it into machine-learning model 2202. This stage can involve noise reduction, outlier detection, feature scaling, or other transformations designed to enhance data quality. For instance, raw sensor data from an ultrasonic transducer could contain spurious spikes due to environmental interference, which optional pre-processing 2210 can filter out. Similarly, if different sensors record temperature in Fahrenheit or Celsius, optional pre-processing 2210 can unify data formats. In certain embodiments, dimensionality reduction techniques, such as principal component analysis, may be applied to handle large feature sets more efficiently.

The selection of optional pre-processing 2210 steps may be guided by the requirements of the neural network 2204 or by best practices in machine-learning workflows. Although shown as a distinct element, optional pre-processing 2210 can be integrated into one or more sensor firmware or the machine-learning pipeline. By controlling the input quality and consistency, optional pre-processing 2210 contributes to the reliability and accuracy of subsequent inferences, ensuring that AI-driven monitoring system 2200 accurately determines one or more distilling characteristics 2214 and offers meaningful guidance for process adjustments.

In some aspects, output data 2212 may refer to the processed or inferred results produced by machine-learning model 2202 (and potentially neural network 2204) after evaluating input data 2206. These results may be represented as numerical values, categorized states (e.g., "distillation nearing completion"), alerts, or recommendations for adjusting distillation parameters. In some instances, output data 2212 may be displayed on a user interface, transmitted to a controller for real-time process modification, or stored for traceability and compliance documentation. Depending on the application's complexity, output data 2212 may take multiple forms simultaneously—for example, a predicted purity level and a time estimate for achieving target alcohol concentration.

In some aspects, additional steps for presenting or using output data 2212, such as generating compliance reports or integrating with enterprise resource planning systems, are contemplated. In some aspects, by capturing the essence of the AI-driven monitoring system 2200's analysis, output data 2212 is the immediate interface between the machine-learning insights and practical actions within a distillery environment. As a result, output data 2212 can maintain consistency, optimize resource usage, and ensure that final products meet desired quality or regulatory standards.

At least one distilling characteristic 2214 associated with the distilling liquid represents an analytical target of the AI-driven monitoring system 2200. Examples of such characteristics include but are not limited to, purity level, distillation completion state, color, proof, alcohol content, or compliance indicators. In some aspects, the machine-learning model may 2202 generate or refine this characteristic by parsing the sensor-derived data points 2208 and applying learned relationships derived from training. Upon determining a characteristic 2214, the AI-driven monitoring system 2200 may signal an operator to terminate heating, adjust flow, or perform other actions that maintain or improve product quality. Characteristic 2214 may inform real-time decisions and/or historical logging. In some instances, characteristic 2214 may be stored and correlated with known production stages, enhancing future model training or facilitating audits. By harnessing the breadth of input data 2206 and leveraging advanced computational approaches (e.g., the neural network 2204), the AI-driven monitoring system 2200 can maintain tight control over distillation, leading to consistent, high-quality spirits aligned with an operator's or regulatory expectations.

Optional additional processing 2216 may occur after machine-learning model 2202 generates output data 2212. This stage can include advanced analytics or decision-making routines that further interpret or refine the output. For example, if characteristic 2214 indicates a high impurity level, optional additional processing 2216 might trigger an automated cleaning cycle or recalibrate sensor thresholds for subsequent distilling operations. Alternatively, 2216 could evaluate trends over multiple batches to forecast maintenance intervals or anticipate shifts in grain quality. In some implementations, these routines may be embedded in a separate software module interacting with a main inference engine, enabling modular expansion that may not affect the underlying neural network 2204. For example, the optional additional processing 2216 may be implemented using rule-based logic, fuzzy controllers, or additional machine-learning models stacked on top of machine-learning model 2202.

In certain embodiments, optional additional processing 2216 generates compliance reports or notifications to regulatory bodies, fulfilling legal obligations for tracking alcohol production. Through its capacity to interpret the machine-learning outputs in broader operational or compliance contexts, optional additional processing 2216 completes the feedback loop, making AI-driven monitoring system 2200 a diagnostic tool and a comprehensive automation platform for distilling processes.

Sensor 2218 may be configured to detect at least one data point associated with a distilling liquid, as described in various embodiments. In one implementation, sensor 2218 could be a radar sensor or an ultrasonic transducer mounted near or on container 2220 to measure reflectance or waveforms indicative of the liquid's properties. Alternatively, sensor 2218 might be any of the sensor types disclosed in the apparatus claims, including dielectric, near-infrared, or ultraviolet-visible sensors. By collecting real-time data on temperature, alcohol concentration, color, volume, or other relevant parameters, sensor 2218 can facilitate a more accurate analysis by the machine-learning model 2202 or neural network 2204. Sensor 2218 may include embedded signal-conditioning electronics or pre-processing features (e.g., filtering or noise reduction) before transmitting measurements to AI-driven monitoring system 2200. Depending on the embodiment, sensor 2218 can be positioned in direct contact with container 2220, spaced apart by a distance 2228, or integrated into a broader array of sensing elements around the distillation apparatus. In some configurations, sensor 2218 is tuned explicitly for detecting surface reflections (e.g., from the surface of liquid 2224) to determine the volume or level of the distilling liquid within container 2220, thereby providing data for controlling and optimizing the distillation process. In some aspects, the sensor 2218 may be the same as or similar to the container monitoring system 150, as described in at least FIG. 1, and/or the processing system 210 as described in at least FIGS. 2-4.

In some aspects, container 2220 may be any vessel or barrel configured to hold a distilling liquid, such as a whiskey barrel, stainless steel column, or other suitable enclosure. As depicted in the figure, container 2220 can house the distilling liquid and accommodate one or more sensors (e.g., sensor 2218). The size, shape, and material of container 2220 may vary based on the distillation requirements and the nature of the liquid being produced. In one example, container 2220 could be an oak barrel employed for flavor infusion and aging, while in another scenario, container 2220 might be a pressurized steel vessel used for high-volume distillation processes. Container 2220 is shown with an external face through which signals (e.g., radar, ultrasound, transmission waves, etc.) can pass, allowing sensor 2218 to collect reflection or transmission data on the surface of the liquid 2224. The interior of container 2220, including inner space 2222, may be partially or fully scaled to maintain specific environmental conditions, such as temperature or pressure. Depending on the embodiment, the distance 2228 between sensor 2218 and the container wall may be zero (e.g., sensor 2218 is mounted directly on container 2220) or greater than zero for remote sensing applications (e.g., between 0 and 1 meter; between 1 and 5 meters; between 5 and 50 meters; etc.). In some aspects, the container 2220 may be the same as or similar to the barrel 110 described in at least FIGS. 1-2, 7A, 7B, and 9.

Inner space 2222 denotes the interior volume of container 2220, where the distilling liquid resides during one or more phases of the distillation or aging process. In certain embodiments, inner space 2222 can maintain a controlled environment, including temperature, humidity, and pressure levels conducive to optimal fermentation, evaporation, or flavor extraction. Depending on the system's configuration, sensor 2218 may non-invasively measure conditions within inner space 2222 by transmitting signals through the container wall. The dimensions of inner space 2222 may be constant or may adjust dynamically if the container is collapsible or features movable partitions.

Where container 2220 is a barrel, inner space 2222 may include head space above the surface of liquid 2224, enabling natural evaporation and flavor development. Data collected from inner space 2222 can feed into AI-driven monitoring system 2200 and machine-learning model 2202, which may analyze the data to provide predictive insights or control actions that maintain product quality and consistency.

The surface of liquid 2224 represents the boundary between the distilling liquid and the head space within container 2220. In certain embodiments, sensor 2218 is directed toward monitoring the surface of liquid 2224 to track liquid level, detect foam or bubbles, or measure fluctuations in color. Such measurements may be used to determine evaporation rates, establish proof of alcohol content, or detect anomalies like excessive frothing. If the distilling process involves multiple stages, the surface of the liquid 2224 can vary in composition or depth over time, reflecting changes in temperature, pressure, or applied heat. Sensor data from the surface of the liquid 2224 may be processed by neural network 2204 or machine-learning model 2202 to predict when to advance to a new distillation phase or to alert an operator that the target characteristic (e.g., color or alcohol proof) has been achieved.

In some implementations, optional additional processing 2216 may incorporate these surface measurements into compliance reports or safety checks. By continuously monitoring the surface of the liquid 2224, AI-driven monitoring system 2200 ensures a more granular control over product quality and helps maintain operational efficiency during the distillation cycle.

Optional post-processing 2226 may represent an additional or parallel data analysis stage after the machine-learning model 2202 and neural network 2204 have generated some intermediate or raw output. Unlike optional additional processing 2216, which may be geared toward broader decision-making or control steps, optional post-processing 2226 could focus on refining, validating, or augmenting the system's immediate analytical results. For instance, optional post-processing 2226 may include cross-verifying distilling characteristics 2214 against known calibration standards or historical performance metrics. In certain embodiments, this stage can reformat the output data 2212 into compliance reports, trend analyses, or user-friendly visualizations for operators and quality assurance personnel.

Optional post-processing 2226 might also integrate external data, such as regulatory thresholds or business rules, to ensure that conclusions align with operational or legal requirements. Depending on the implementation, optional post-processing 2226 can be executed in a local computing environment, distributed cloud infrastructure, or even on an edge device close to sensor 2218. By performing these additional refinements, optional post-processing 2226 can improve the reliability, clarity, and actionable value of the insights provided by AI-driven monitoring system 2200, thereby contributing to optimal distillation outcomes and robust compliance adherence.

Distance 2228 indicates the measured gap between sensor 2218 and the external face or surface of container 2220, which can be zero, a fraction of a meter, or multiple meters, depending on the system design and sensing technology. In one embodiment, distance 2228 is zero when sensor 2218 is physically attached to container 2220, ensuring minimal signal loss for radar or ultrasonic measurements. In another embodiment, distance 2228 may range up to several meters if sensor 2218 is mounted remotely or operational constraints dictate separation, such as high temperatures or pressurized vessels. The distance 2228 could also refer to the separation between sensor 2218 and the surface of the liquid 2224 when sensor 2218 is placed at or near the container's top.

Various implementations may utilize distance 2228 to calibrate signal intensity, account for wave attenuation, or determine the liquid's level for volume calculations. Information regarding distance 2228 may also feed into optional post-processing 2226 routines to correct raw measurements, thereby assisting machine-learning model 2202 in generating accurate outputs. By tracking and adjusting for distance 2228, AI-driven monitoring system 2200 achieves consistent measurements, enabling better oversight of distillation progress and facilitating high-quality results in spirit production.

Figure 23:
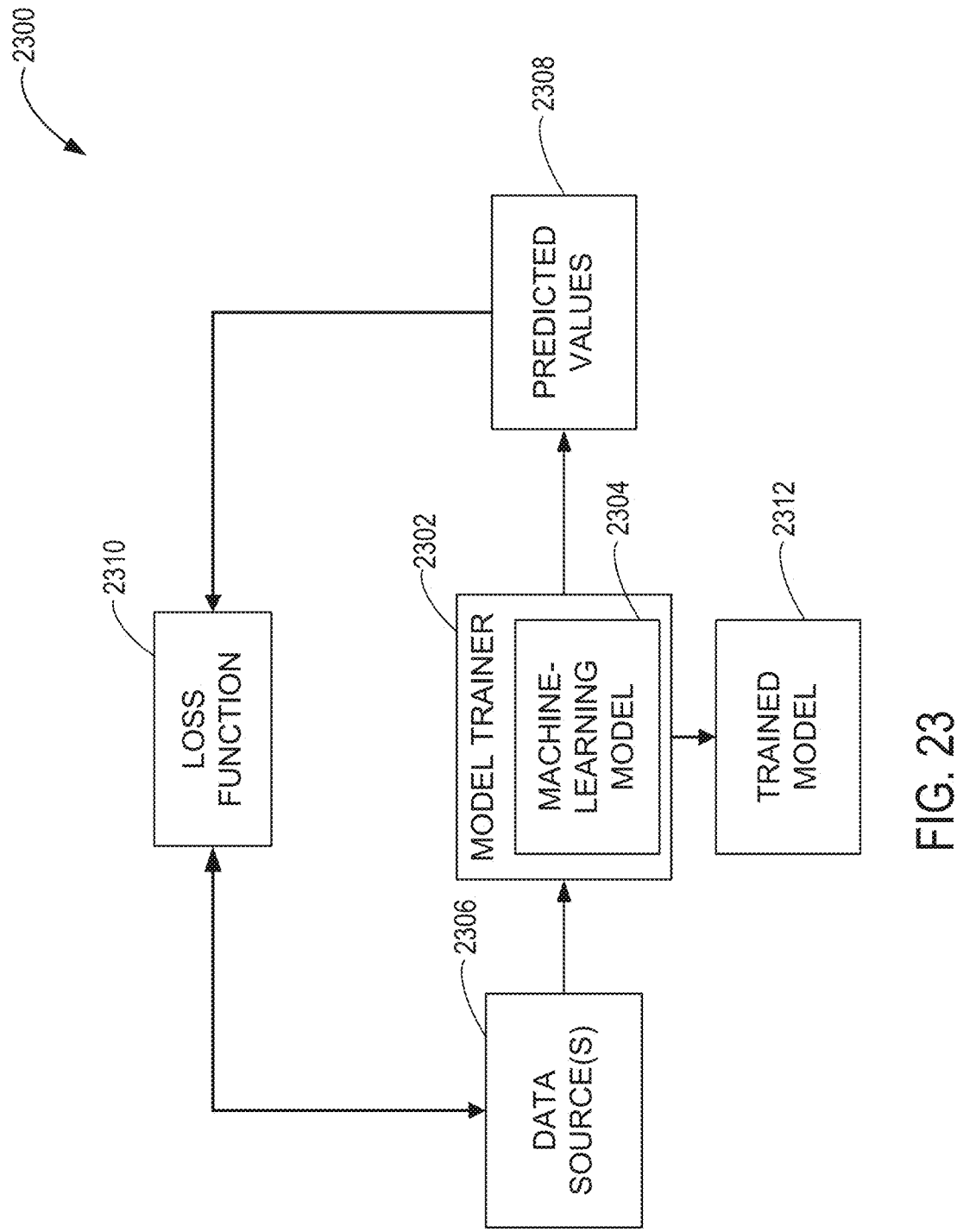
FIG. 23 is a schematic representation of a training system for refining the parameters of a machine-learning model.

FIG. 23 illustrates an example training system 2300 in accordance with the principles of the invention. In one embodiment, the training system 2300 is configured to develop, refine, or otherwise optimize the parameters of a machine-learning model 2304, which may be implemented for use in analyzing distilling processes as discussed with respect to FIG. 22. The example training system 2300 may leverage various data source(s) 2306, apply a loss function 2310 to measure model performance, generate predicted values 2308 for comparison with a ground truth, and output a trained model 2312 that can be deployed in an operational environment.

In some aspects, the training system 2300 provides a comprehensive framework for creating and improving machine-learning models for tasks such as distillation analysis, product quality monitoring, or other complex data-driven applications. In one example, the training system 2300 can include specialized hardware, such as GPUs or TPUs, to efficiently process large datasets. The example training system 2300 may also integrate with cloud-based services that offer scalable compute resources for batch processing or continuous retraining. Various embodiments of the training system 2300 can employ different data preprocessing pipelines, hyperparameter search strategies, and validation protocols to ensure that the resulting model generalizes effectively to new datasets.

Although depicted here as a single, cohesive block, training system 2300 may include multiple distributed components, such as components dedicated to data ingestion, while other components are responsible for model evaluation. The elements of training system 2300 can be adjusted based on the complexity and domain requirements of the target application. For example, the elements of training system 2300 may be based on compliance reporting or real-time control in distillation processes. By centralizing these tasks, the training system 2300 enhances machine-learning-based solutions' reliability, maintainability, and scalability.

In some aspects, the model trainer 2302 orchestrates the core learning loop within training system 2300. The model trainer 2302 may handle the ingestion of training data, the forward pass of the machine-learning model 2304 to produce predicted values 2308, and the subsequent calculation of error via loss function 2310. Depending on the embodiment, model trainer 2302 may also manage hyperparameter tuning (e.g., learning rate, batch size, or network architecture selection) by iterating over multiple candidate configurations and evaluating their performance. Model trainer 2302 can operate in offline batch mode—where large volumes of data from data source(s) 2306 are processed—or in an online or streaming mode, adapting in near real-time to newly available data points. Moreover, model trainer 2302 may interface with automated or manual triggers, such as scheduled retraining windows or operator-initiated updates. While the figure shows model trainer 2302 as a single unit, different components may reside on separate servers or virtual machines, coordinated by a central scheduling service. In some instances, model trainer 2302 leverages existing machine-learning libraries, frameworks, or custom-coded routines to implement backpropagation, gradient descent, or other optimization techniques. Ultimately, model trainer 2302 outputs refined model parameters stored in trained model 2312, ensuring an iterative, data-driven approach to increasing the accuracy and robustness of machine-learning model 2304.

Machine-learning model 2304 may be the same as or similar to the machine-learning model 2202 discussed in FIG. 22, or it can represent a new or variant architecture suited to the training processes carried out by training system 2300. In certain embodiments, machine-learning model 2304 includes layers of an artificial neural network, possibly incorporating recurrent or convolutional elements. Alternatively, the machine-learning model may utilize techniques such as Gaussian process regression, decision trees, or hybrid models combining multiple approaches. During training, machine-learning model 2304 receives input data—such as distillation parameters, sensor readings, or external contextual factors—from data source(s) 2306 and produces predicted values 2308. These predictions may then be evaluated against ground truth (or labeled data) via loss function 2310.

The architecture of machine-learning model 2304 can be adjusted throughout the training cycle, allowing for the pruning of layers, adding dropout mechanisms to reduce overfitting, or integrating attention modules to capture long-range dependencies. In addition, machine-learning model 2304 may store interim states for partial inference or check-pointing such that the training process can be resumed if interrupted. Once model trainer 2302 converges on optimal parameters, the finalized version of machine-learning model 2304 may be encapsulated in trained model 2312 for subsequent deployment.

Data source(s) 2306 can provide raw and processed input data necessary for training machine-learning model 2202 within training system 2300. These sources may include sensor logs capturing distilling liquid characteristics (e.g., temperature, alcohol content, flow rate), historical production data, or simulated datasets representing various operating conditions. In some embodiments, data source(s) 2306 also supply ground truth labels collected from manual inspections, certified measuring instruments, or regulatory compliance records to guide the loss function 2310 in calibrating model accuracy. Data source(s) 2306 may reside in multiple databases, local file systems, or cloud storage services and can be accessed in real-time (streaming mode) or as batch files. The data pipeline may involve optional preprocessing steps (e.g., normalization, feature extraction, outlier filtering) or rely on model trainer 2302 to handle such transformations. As the complexity of distillation processes can vary significantly, data source(s) 2306 can encompass data from single-sensor readings to multi-modal datasets combining environmental factors, chemical analyses, and historical performance logs. Such information may enable the machine-learning model 2304 to learn correlations across varying conditions, improving the predictive power and operational reliability of the trained model 2312.

In some aspects, the loss function 2310 evaluates the difference (or error) between predicted values 2308 generated by machine-learning model 2304 and corresponding ground truth data provided by data source(s) 2306. Sometimes referred to as a cost function, loss function 2310 may employ metrics like mean squared error, cross-entropy, or mean absolute error, or it can be adapted with domain-specific scoring rules relevant to distilling processes. For instance, the loss function might disproportionately penalize large deviations in scenarios where precise temperature or proof estimations are important. During each training iteration, model trainer 2302 uses feedback from loss function 2310 to update the parameters within machine-learning model 2304, reducing overall error across the dataset. This feedback loop continues until the loss function 2310 converges to a minimal or otherwise acceptable value, signaling that machine-learning model 2304 has adequately learned the relationships in the data.

In some implementations, loss function 2310 may be combined with regularization terms (e.g., L2 or dropout) to prevent overfitting, or it can incorporate weighting factors that emphasize particular classes of errors. By continuously quantifying model performance, loss function 2310 may be an engine driving iterative improvements in training system 2300, ensuring that the final output captured in trained model 2312 meets accuracy and reliability criteria.

In some aspects, the predicted values 2308 represent the real-time output or inference results produced by machine-learning model 2304 as it processes the input data from data source(s) 2306. These predicted values 2308 may correspond to numerical estimates of distillation attributes—like temperature, proof, pH—or more sophisticated classifications (e.g., "normal operation" vs. "risk of contamination"). During training, predicted values 2308 flow to loss function 2310 for error calculation against known ground truth labels. Outside the training context, predicted values 2308 can be used directly by an inference engine (e.g., in an AI-driven monitoring system similar to FIG. 22) for process control, compliance reporting, or operator alerts. In certain embodiments, predicted values 2308 may be captured as intermediate outputs in a multi-stage pipeline, feeding into other analytic or decision-making modules.

The level of precision or recall exhibited by predicted values 2308 may be improved over successive training iterations as the model trainer 2302 refines the internal parameters of machine-learning model 2304. By differentiating between predicted values 2308 and the final trained model 2312, FIG. 23 clarifies how an iterative training cycle converges on an optimally performing model suitable for deployment.

Trained model 2312 may be the same as or similar to the machine-learning model 2202 described in FIG. 22. However, in the context of FIG. 23, trained model 2312 specifically denotes the finalized or converged version of machine-learning model 2304 after completing the training process. Once model trainer 2302 has iterated through sufficient data (from data source(s) 2306) and adjusted model parameters based on loss function 2310, the resulting parameters may be encapsulated in trained model 2312. This trained artifact can be deployed in operational environments, such as an AI-driven distillation monitoring system or a broader compliance and control architecture. In some aspects, the trained model 2312 may be serialized for storage on disk or in a database, allowing for efficient loading or redeployment in real-time production systems. As new data becomes available, trained model 2312 can be periodically retrained or fine-tuned, maintaining and enhancing predictive accuracy for evolving distillation conditions or broader use cases.

Figure 24:
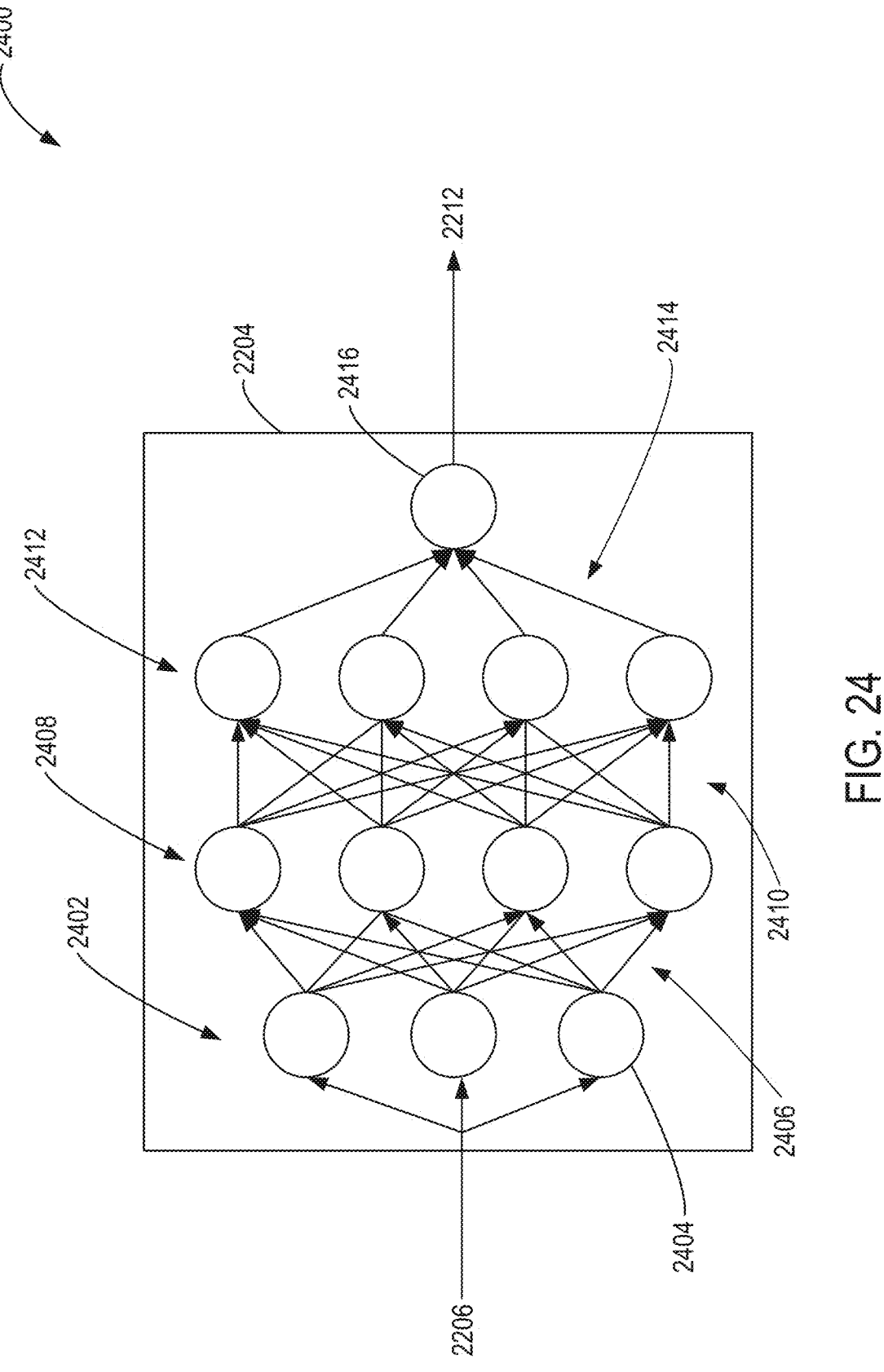
FIG. 24 depicts an example artificial neural network architecture, including multiple layers of neurons interconnected by weighted edges.

FIG. 24 depicts an example artificial neural network 2400 that may be utilized for analyzing data associated with a distilling liquid, predicting completion states, or performing other complex inference tasks in accordance with the principles and claims described previously. In one embodiment, the artificial neural network 2400 can form part of a machine-learning model (e.g., machine-learning model 2202), which receives sensor inputs (such as temperature, alcohol concentration, or color) and generates an output indicative of at least one distilling characteristic. Although represented in a simplified block diagram, the artificial neural network 2400 may comprise numerous interconnected layers, each containing multiple neurons linked by weighted edges.

In some aspects, for example, the artificial neural network 2400 provides a structured arrangement of computational nodes and interconnections designed to process input signals and produce meaningful outputs. In some embodiments, the artificial neural network 2400 may be configured to model relationships among distilling parameters—such as temperature, pressure, flow rate, or alcohol content—similar to or in conjunction with previously described machine-learning architectures. By learning weighted connections between neurons, the artificial neural network 2400 can capture intricate correlations, thereby enabling accurate predictions of distilling characteristics (e.g., purity level, distillation completion state). In certain implementations, the artificial neural network 2400 is trained using a system like training system 2300 of FIG. 23, which supplies ground truth labels and iteratively adjusts network weights to minimize error. The size, depth, and connectivity pattern of the artificial neural network 2400 can be adapted to suit different computational or domain requirements, and may include advanced techniques such as skip connections, batch normalization, or attention mechanisms.

Although FIG. 24 illustrates a feedforward topology, variations of the artificial neural network 2400 may include recurrent or convolutional layers depending on the specific data modalities (e.g., time-series temperature data or near-infrared spectral imaging). In operation, the artificial neural network 2400 can function in real-time or offline modes, supporting various applications in distillation monitoring, compliance checking, and overall process optimization.

In some aspects, the first layer of neurons 2402 receives initial input signals. In some aspects, the input signals may correspond to input data 2206 described in FIG. 22. In some aspects, the input data may correspond to raw or pre-processed sensor data as previously described. These neurons serve as the entry point of the artificial neural network 2400, where each neuron transforms an incoming value by applying a weight, a bias, and an activation function (e.g., ReLU, sigmoid, or tanh).

In some configurations, the first layer of neurons 2402 may be linked with input channels representing temperature readings, reflection measurements, proof values, or other data points pertinent to the distilling liquid's state. By systematically adjusting these weights and biases during a training phase (such as the one outlined in training system 2300), the first layer of neurons 2402 begins to learn discriminative features or patterns in the input data. Depending on the architecture, first layer of neurons 2402 can contain dozens, hundreds, or even thousands of individual neurons, each capturing a different facet of the data. This layer may also include additional techniques like dropout or batch normalization to improve generalization and convergence rates. Once the first layer of neurons 2402 completes its computations, the resultant signals are propagated through edges 2406 to subsequent layers, building a hierarchical representation of the distillation process or other target application.

For example, neuron 2404 illustrates a single computational unit within artificial neural network 2400. Although shown as a single circle in FIG. 24, neuron 2404 typically includes multiple internal components: weighted inputs, an aggregation or summation function, a bias term, and an activation function. During forward propagation, neuron 2404 receives input values from either an external source (in the case of the first layer) or neurons in a preceding layer. It then calculates a weighted sum, adds a bias, and processes the sum through the activation function. Various activation functions—such as ReLU (Rectified Linear Unit), sigmoid, or tanh—can be employed to introduce nonlinearity, thus enabling the network to approximate complex, real-world relationships.

In a training scenario, neuron 2404's weights and bias are iteratively updated via algorithms like gradient descent, which references a loss function (e.g., in training system 2300) to minimize predictive errors. Although depicted generically, neuron 2404 may be similar or identical to the computational elements described in prior figures, such as the neurons within neural network 2204 of FIG. 22. By aggregating outputs from many neurons, for example, neuron 2404, the artificial neural network 2400 gains the capacity to model intricate phenomena like distillation progress or compliance thresholds.

In some aspects, edges 2406 connect the first layer of neurons 2402 to the subsequent layer, enabling information flow within artificial neural network 2400. Each edge may carry a weighted signal, where the weight may correspond to a learnable parameter adjusted through backpropagation or other form updating during a training process. In some embodiments, edges 2406 can represent purely feedforward connections, transmitting data from left (input) to right (hidden layers), while in other architectures, they might include recurrent or lateral connections for handling sequential or contextual data.

In some aspects, the edges 2406 define the network's topology, determining how each neuron in the first layer of neurons 2402 influences subsequent layers. The magnitude and sign of the weight on each edge can amplify, diminish, or invert the signal passed along, thereby shaping how quickly or effectively the network converges on optimal solutions. Depending on the complexity of the task, like predicting precise proof levels or identifying anomalies, edges 2406 may be dense (fully connected) or sparse (selectively connected). In some aspects, edges 2406 could incorporate attention-based mechanisms or gating functions in some advanced configurations to dynamically modulate signal strength. Although visually similar to edges 2410 and 2414, edges 2406 pertain specifically to the pathways bridging first layer of neurons 2402 with the network's subsequent layer, forming a foundational step in the overall forward propagation process.

In some aspects, the second layer of neurons 2408 resides within artificial neural network 2400 as an intermediate (or "hidden") layer, situated between first layer of neurons 2402 and third layer of neurons 2412. By processing signals relayed through edges 2406, the second layer of neurons 2408 may extract increasingly abstract or higher-level features relevant to a target task, such as distillation endpoint prediction or real-time quality assessment. Each neuron within the second layer of neurons 2408 may employ a similar computational structure to, for example, neuron 2404, incorporating weighted sums and activation functions. However, the number of neurons can be varied to control the network's expressive power, with more neurons potentially providing better feature extraction at the risk of overfitting.

In some embodiments, the second layer of neurons 2408 interacts with optional batch normalization or dropout layers to improve generalization.

During training, the outputs of the second layer of neurons 2408 are combined, adjusted, and tuned based on the loss function's feedback, ensuring that relevant relationships are encoded in the network's weights. This hidden layer can be replicated multiple times (e.g., a multi-layer perceptron) to form deeper architectures, enabling the network to capture intricate, non-linear interactions within distilling data. Once processed by the second layer of neurons 2408, resulting signals propagate through edges 2410 toward the third layer of neurons 2412, further refining the network's representation.

In some aspects, edges 2410 may transmit intermediate signals from the second layer of neurons 2408 to the third layer of neurons 2412. Similar in function to edges 2406, these connections embody the learned parameters (i.e., weights) that progressively transform raw input data into meaningful representations. As the signals advance through the edges 2410, the signals become increasingly specialized, capturing refined patterns for tasks such as, but not limited to predicting distillation completion, volume, time, proof, temperature, humidity, evaporation rates, and/or evaluating compliance thresholds. Each edge within edges 2410 may contribute to how the receiving neuron calculates its weighted sum; slight variations in weight values can significantly influence the network's final output. Given that the second layer of neurons 2408 may contain numerous neurons, edges 2410 can form a dense mesh of interactions, with each neuron in second layer of neurons 2408 potentially connecting to each neuron in third layer of neurons 2412. This dense connectivity can facilitate pattern extraction but may also increase computational load.

During training, backpropagation, or other updating processes, may update the weights associated with edges 2410 by comparing the network's predictions against ground truth data, shifting the entire network's parameter space toward an optimal configuration. Though conceptually similar to edges 2406 and edges 2414, edges 2410 specifically concern the linkages carrying signals from the network's middle domain to a nearer-output domain.

In some aspects, the third layer of neurons 2412 is located downstream of the second layer of neurons 2408 in the artificial neural network 2400. Like previous layers, it can serve as a further hidden layer—or, in certain configurations, it might be the penultimate layer preceding the final layer 2416. The third layer of neurons 2412 refines features extracted by earlier layers, enabling the network to distill or condense complex representations into more task-specific signals. Each neuron within the third layer of neurons 2412 may resemble example neuron 2404, employing a weighted aggregation of the outputs from the second layer of neurons 2408 (passed along edges 2410) and an activation function to produce a new set of feature activations.

Depending on the architectural depth, the third layer of neurons 2412 could be repeated multiple times to form a deeper network, each repetition offering additional capacity to learn nuanced relationships between distillation input data and target outputs. For instance, if the network predicts multiple distilling characteristics (e.g., proof and color), the third layer of neurons 2412 may be configured to separate or parallelize certain computations within different neuron groups. After processing, the outputs of the third layer of neurons 2412 traverse edges 2414 toward the final layer

2416, where the network generates the culminating predictions relevant to the specified distillation task or other domain applications.

In some aspects, the edges 2414 represent the connectivity between the third layer of neurons 2412 and the final layer 2416 in artificial neural network 2400. In many configurations, these edges are the last set of connections through which the network's processed signal flows before reaching the network's overall output. Each weight in edges 2414 may influence how strongly the final layer 2416 responds to the aggregated signals from the third layer of neurons 2412. Because this transition often marks the boundary between the network's representational core and its output stage, the adjustments made to edges 2414 during training can have a pronounced effect on the final predictions, such as purity levels, completion states, or other distillation-related metrics. The density of edges 2414 may vary; in simpler networks, each neuron in the penultimate layer connects directly to every neuron in the final layer 2416, while in more specialized architectures, certain constraints or patterns in connectivity could be imposed. Regardless of the structure, these edges 2414 reflect the culminating stage of forward propagation, acting as the last "interpretative" step through which hidden-layer features are translated into a final inference. When paired with a suitable loss function, the backpropagation process refines the weight values of edges 2414 in tandem with the rest of the network, ensuring the best alignment between the network's computed output and ground truth labels.

The final layer 2416 may include the output layer of the artificial neural network 2400, producing a definitive inference or prediction that can be mapped onto a distillation characteristic, compliance measure, or another metric relevant to the claims. In some aspects, the final layer 2416 may generate output data 2212 as previously described in FIG. 22. Where the network is designed for classification (e.g., "normal operation" vs. "anomaly"), final layer 2416 might employ a softmax activation to generate probability distributions.

Alternatively, if the task involves regression (e.g., predicting proof, temperature, or color intensity), a linear activation may be used. In certain embodiments, the final layer 2416 is the same or similar to an output layer described in previously referenced figures, such as the machine-learning model output data 2212 in FIG. 22. After the signals from the third layer of neurons 2412 pass through edges 2414, the neuron(s) in final layer 2416 consolidate them into an interpretable output, which is then compared against ground truth labels during training (e.g., via the loss function discussed in FIG. 23). In a production setting, the predictions made by final layer 2416 can guide a distillation system's control logic, trigger alerts, or feed into compliance reporting modules.

Figure 25:
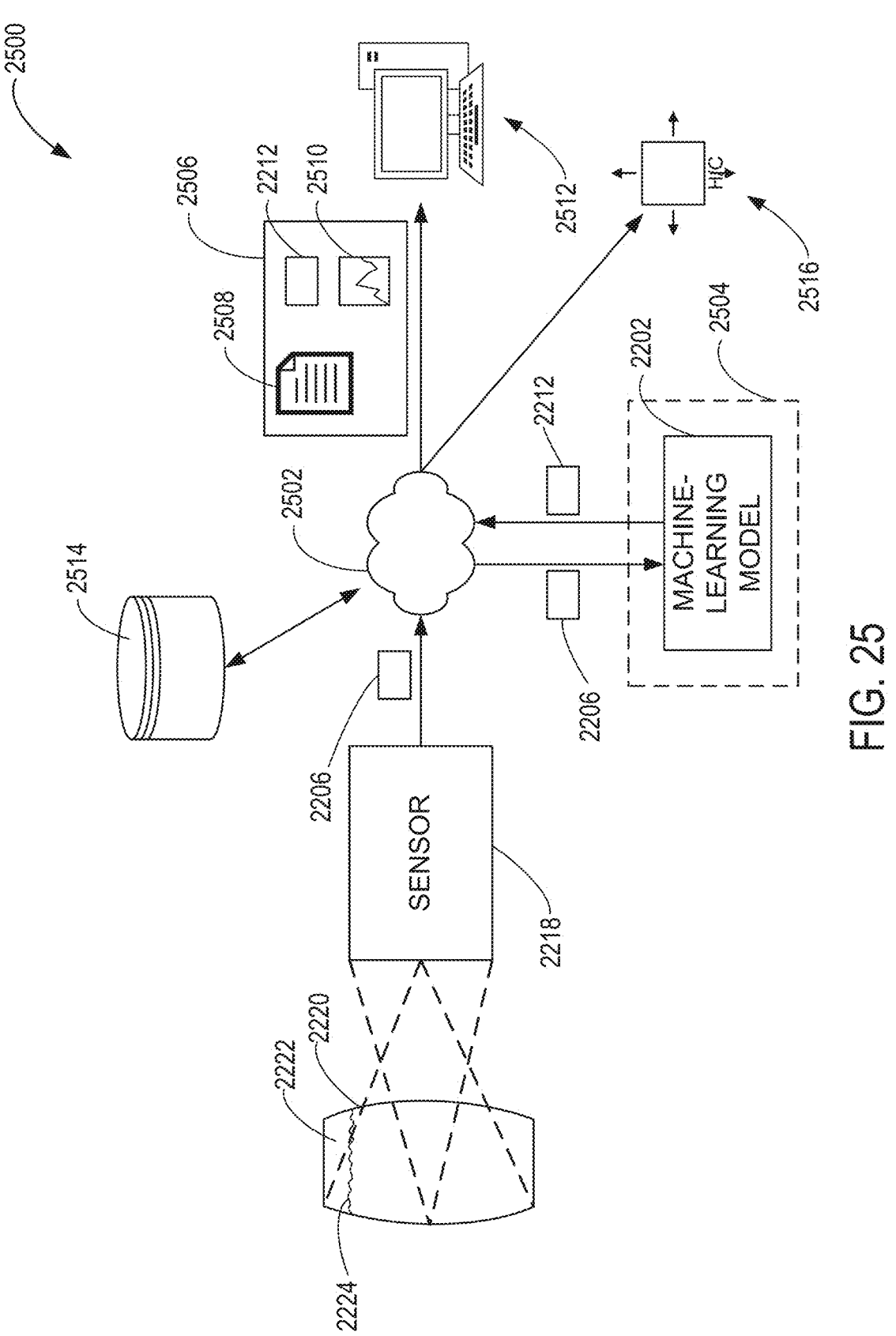
FIG. 25 illustrates an AI-driven platform deployed in a networked environment.

FIG. 25 illustrates an example of an AI-driven platform 2500 for analyzing a distilling liquid in accordance with the principles of the invention. As shown, sensor 2218 (as previously described in FIG. 22) may obtain input data 2206 (e.g., including one or more data points) from container 2220, where container 2220 encompasses inner space 2222 and surface of the distilling liquid 2224. The collected input data 2206 (e.g., including one or more data points) may be transmitted via network 2502 and stored in repository 2514, subsequently processed by machine-learning model 2202 (which may be hosted on processing device 2504). The prediction or output data 2212 can then be communicated back through network 2502, optionally stored in repository 2514, and eventually delivered to a processing device 2512 for display or to a controller 2516 for automated adjustments.

In some aspects, the example AI-driven platform 2500 provides an end-to-end solution for monitoring, analyzing, and controlling distilling processes. This example AI-driven platform 2500 may include a range of hardware and software components configured to sense parameters (e.g., temperature, proof, color) of the distilling liquid, run predictive algorithms based on machine-learning model 2202, and generate real-time or near-real-time adjustments to maintain quality or compliance. In one embodiment, for example, AI-driven platform 2500 may leverage a distributed architecture where sensor 2218 captures input data 2206 (e.g., including one or more data points) and forwards them to network 2502, which routes the information to either processing device 2504 or repository 2514 for further analysis and storage. In some aspects, the AI-driven platform 2500 can facilitate various modes of operation. For example, the example AI-driven platform 2500 may run continuously to provide ongoing insights or the example AI-driven platform 2500 may operate in batch mode to analyze historical data from prior distillation cycles. For example, the AI-driven platform 2500 may integrate with an on-site or cloud-based environment. By encompassing data acquisition and intelligent inference, the AI-driven platform 2500 can adjust one or more distillation processes, such as heat levels, timing, or environmental conditions, based on data-backed predictions.

In some aspects, network 2502, which may be the same as or similar to network 480 of FIG. 4, represents the communication backbone within the example AI-driven platform 2500. The network 2502 may facilitate data exchange among sensor 2218, machine-learning model 2202, repository 2514, and other components. Network 2502 is a local area network (LAN) in some embodiments, allowing direct, low-latency communication in a distillery environment. Alternatively, network 2502 could be a wide area network (WAN), such as the Internet, enabling remote monitoring and control over long distances. Security measures—like encryption or virtual private network (VPN) tunnels—may be implemented to protect sensitive distillation metrics or compliance data. In some aspects, network 2502 can handle various data transfer protocols (e.g., TCP/IP, MQTT) to accommodate real-time streams of input data 2206 (e.g., including one or more data points), batch uploads of historical logs to repository 2514, or model updates from training systems located off-site. By serving as a centralized conduit, network 2502 provides a conduit to share measured data, intermediate processing results, or final output data 2212 across the example AI-driven platform 2500.

Processing device 2504 may be the same as or similar to processing device 210 of FIG. 2 or any other computing device with sufficient computational resources to execute or host machine-learning model 2202. Within the example AI-driven platform 2500, the processing device 2504 can accomplish tasks such as preprocessing sensor data such as input data 2206 (e.g., including one or more data points), performing inference in real-time, or running training routines in conjunction with repository 2514. Depending on system design, processing device 2504 may be a specialized machine-learning accelerator (e.g., GPU-based or FPGA-based system), a general-purpose server, and/or a distributed set of nodes in the cloud.

By executing predictive algorithms, processing device 2504 can generate output data 2212 that indicates distilling liquid characteristics like alcohol proof, completion states, or compliance thresholds. These predictions may subsequently be shared over network 2502 for display on processing device 2512, stored in repository 2514 for historical reference, or transmitted to controller 2516 for automated adjustments. In a typical workflow, processing device 2504 receives input data (e.g., including one or more data points) from sensor 2218, possibly via network 2502, runs the data through machine-learning model 2202, and returns actionable insights to the rest of the example AI-driven platform 2500. The processing device 2504 can interface with external services, such as advanced analytics tools or training pipelines, to provide ongoing refinement of the model's predictive accuracy and reliability.

For example, output data 2506 may comprise one or more forms similar to output data 2212 from FIG. 22, including textual or graphical results, reports, or compliance statements reflecting the machine-learning model's predictions. As depicted in FIG. 25, example output data 2506 can encompass document 2508, such as an analysis report or compliance certification, and/or a time series chart 2510 illustrating trends in distilling parameters (e.g., temperature, pH, alcohol content) over time. These outputs may be generated through processing device 2504 running the machine-learning model 2202, potentially informed by data stored in repository 2514 or received through network 2502 from sensor 2218.

In certain embodiments, for example, output data 2506 may be enriched with external metadata, such as environmental readings from other parts of the facility, to provide a holistic view of the distillation process. This refined information can be displayed on processing device 2512 for human operators, saved in repository 2514 for future reference, or passed to controller 2516 to trigger automated responses. Providing timely and intuitive visuals, such as output data 2506, helps operators confirm product quality, maintain regulatory compliance, and rapidly address emerging issues in the distillation workflow.

Processing device 2512 may be configured to display example output data 2506 (e.g., one or more of the analytics documents 2508, a time series chart 2510, or other insights). In the illustrated embodiment, processing device 2512 may be a standard desktop computer, laptop, tablet, or specialized industrial terminal, offering a user interface that allows operators to interpret the model-generated predictions. For instance, if the example output data 2506 reveals that the distillation process is nearing completion, an operator viewing processing device 2512 can take proactive steps to prepare for the next production stage or finalize compliance reports. By linking to network 2502, processing device 2512 can retrieve historical data from repository 2514, compare past performance to current readings, or run additional analytics modules. In some cases, processing device 2512 can also serve as an input node for adjusting model parameters or scheduling new training sessions on processing device 2504. This multi-directional flow underscores the claims emphasizing integrated systems that collect sensor data, run machine-learning algorithms, and deliver actionable results to human or automated decision-makers. Furthermore, processing device 2512 can facilitate collaboration among different departments, allowing quality assurance teams, regulatory compliance officers, and production managers to converge on a unified dashboard.

Repository 2514, shown here as a database or storage unit, can hold raw sensor data (e.g., readings from sensor 2218 capturing temperature, flow rate, or reflection measurements) and processed data (such as output data 2212 from the machine-learning model 2202). As new input data 2206 (e.g., including one or more data points) are collected from container 2220, repository 2514 may archive them alongside timestamps, batch identifiers, or other metadata crucial for traceability and future analysis. In certain implementations, repository 2514 also stores configuration files, model checkpoints, or compliance documentation generated, such as output data 2506.

Whether physically located on-premise or managed via a cloud service, repository 2514 supports high availability, redundancy, and secure access protocols to ensure data integrity. This centralized storage enables retrospective studies—comparing historical distillation cycles to current ones—and allows for continuous improvement of the machine-learning model 2202 by feeding updated data into retraining routines. Through network 2502, repository 2514 can share relevant datasets with processing device 2512 for real-time decision-making or remote operators for audit and regulatory compliance tasks.

In some aspects, the controller 2516 may be one or more devices responsible for implementing automated adjustments within the distillation environment. Examples include HVAC controllers regulating temperature and humidity, movement controllers adjusting flow rates, timing controllers scheduling operational stages, or event controllers reacting to predefined triggers (e.g., threshold-based alerts derived from output data 2212). By interfacing with network 2502, controller 2516 receives real-time or near-real-time instructions from machine-learning model 2202 running on processing device 2504 and any relevant data stored in repository 2514. In response, controller 2516 can alter process variables such as valve positions, heating element intensities, environmental conditions, dates, times, and timelines to maintain optimal distillation conditions. In some aspects, the controller 2516 provides a closed-loop feedback mechanism that allows the AI-driven platform 2500 to analyze and actively influence a distilling liquid. If, for instance, the machine-learning model 2202 predicts that the liquid has reached a target proof, controller 2516 may automatically cool down the system or switch to a different process stage. In some aspects, controller 2516 could also log actions back into repository 2514 for transparency and auditing.

Figure 26:
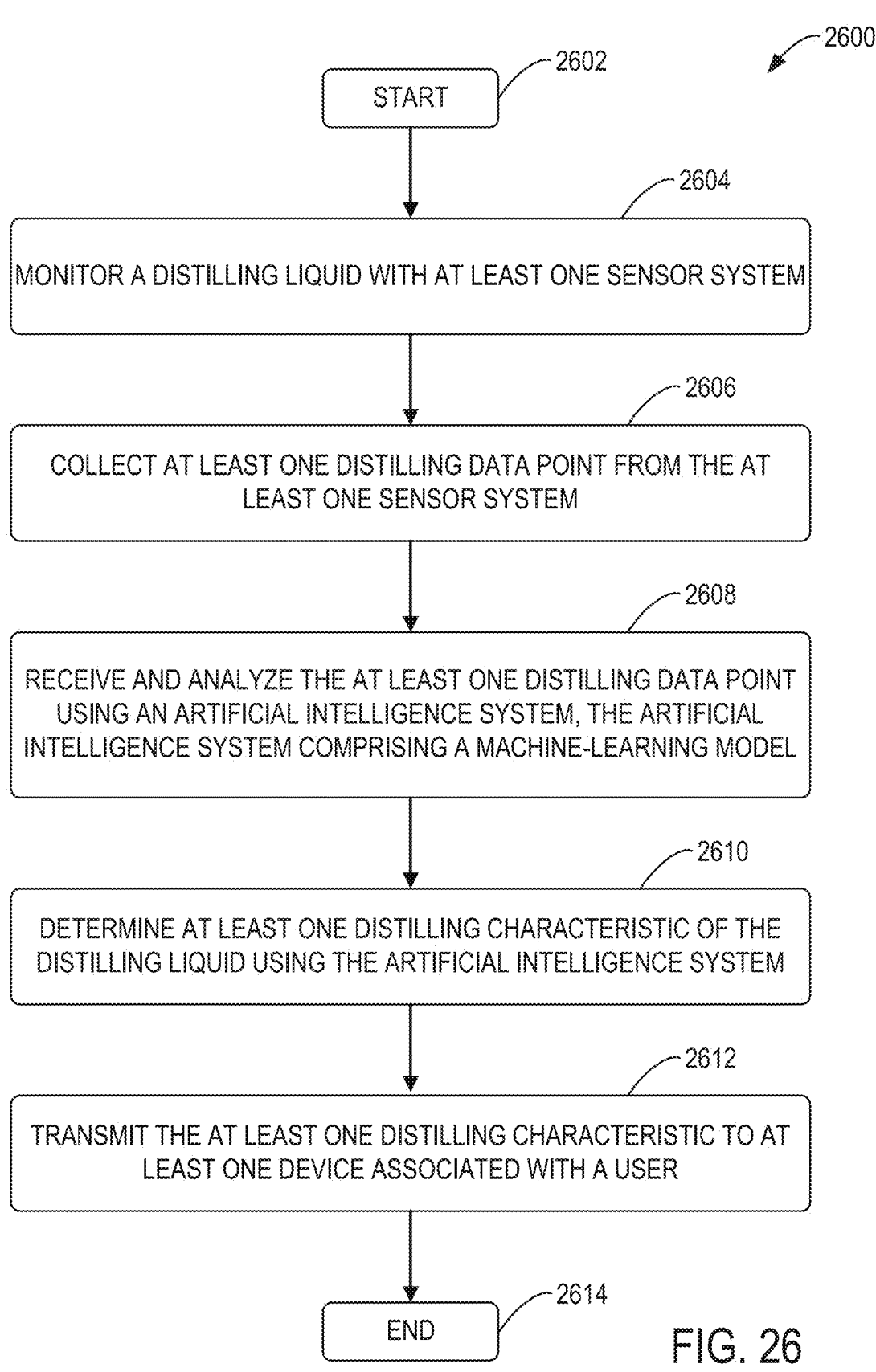
FIG. 26 illustrates a flowchart of an exemplary method for analyzing a liquid in a distilling system.

FIG. 26 shows a method 2600 for analyzing a liquid in a distilling system. In one aspect, method 2600, or any aspect related to it, may be performed by an apparatus, such as container monitoring system 150 as described in at least FIG. 1, processing system 210 as described in at least FIGS. 2-3, 7A-7B, and 9, and/or one or more components of the AI-driven monitoring system 2200 as described in at least FIG. 22, one or more components of the machine-learning model 2202 as described in at least FIGS. 22-25, one or more components of the neural network 2204 as described in at least FIGS. 22-25, and/or one or more components of the AI-driven platform 2500 as described in at least FIG. 25, which includes various components operable, configured, or adapted to perform the method 2600.

Method 2600 begins at 2602 and proceeds to 2604 with monitoring a distilling liquid with at least one sensor system. In some aspects, the at least one sensor system comprises: at least one transmission antenna positioned on an external face of a tank, the at least one transmission antenna configured to transmit a signal into the tank; and at least one receiving antenna, configured to receive the transmitted signal.

Method 2600 then proceeds to 2606 with collecting at least one distilling data point from the at least one sensor system.

Method 2600 then proceeds to 2608 with receiving and analyzing the at least one distilling data point using an artificial intelligence system, the artificial intelligence system comprising a machine-learning model. In some aspects, the machine-learning model is at least one of a gaussian process regression, a convolutional neural network, a long short-term memory, and a hybrid convolution neural network long short-term memory.

Method 2600 then proceeds to 2610 with determining at least one distilling characteristic of the distilling liquid using the artificial intelligence system.

Method 2600 then proceeds to 2612 with transmitting the at least one distilling characteristic to at least one device associated with a user.

Method 2600 then ends at 2614.

Note that FIG. 26 is just one example of a method, and other methods including fewer, additional, or alternative steps are possible consistent with this disclosure.

Figure 27:
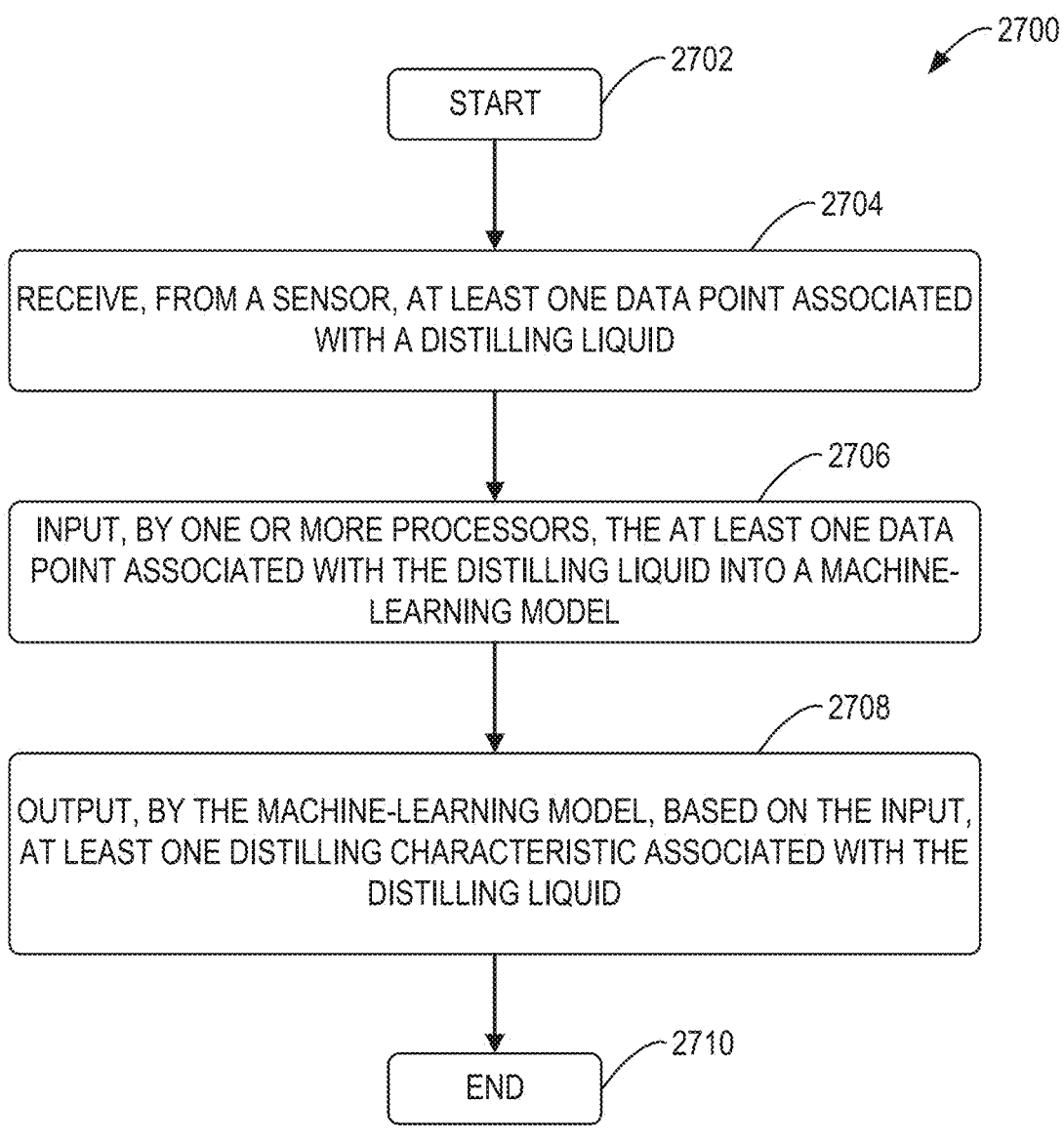
FIG. 27 illustrates a flowchart of an exemplary method for analyzing a distilling liquid.

FIG. 27 shows a method 2700 for analyzing a distilling liquid. In one aspect, method 2700, or any aspect related to it, may be performed by an apparatus, such as container monitoring system 150 as described in at least FIG. 1, processing system 210 as described in at least FIGS. 2-3, 7A-7B, and 9, and/or one or more components of the AI-driven monitoring system 2200 as described in at least FIG. 22, one or more components of the machine-learning model 2202 as described in at least FIGS. 22-25, one or more components of the neural network 2204 as described in at least FIGS. 22-25, and/or one or more components of the AI-driven platform 2500 as described in at least FIG. 25, which includes various components operable, configured, or adapted to perform the method 2700.

Method 2700 begins at 2702 and proceeds to 2704 with receiving, from a sensor, at least one data point associated with a distilling liquid.

Method 2600 then proceeds to 2706 with inputting, by one or more processors, the at least one data point associated with the distilling liquid into a machine-learning model.

Method 2600 then proceeds to 2708 with outputting, by the machine-learning model, based on the input, at least one distilling characteristic associated with the distilling liquid.

Method 2600 then ends at 2710.

Note that FIG. 27 is just one example of a method, and other methods including fewer, additional, or alternative steps are possible consistent with this disclosure.

Additional non-limiting implementation examples are provided below.

A method for analyzing a distilling liquid, the method comprising: receiving, from a sensor, at least one data point associated with a distilling liquid; storing the at least one data point in one or more memories; inputting, by one or more processors, the at least one data point associated with the distilling liquid into a machine-learning model; and outputting, by the machine-learning model, based on the input, at least one distilling characteristic associated with the distilling liquid.

In some aspects, the method further comprises: transmitting a signal through an external face of a container housing the distilling liquid and into the container; and receiving at least one of a reflected portion or a transmitted portion of the signal as the at least one data point associated with the distilling liquid. In some aspects, the transmitter may transmit via one or more transmission antenna, the signal through the external face of a container housing the distilling liquid and into the container. In some aspects, the receiver may receive, via one or more receiving antennas, the at least one of a reflected portion or a transmitted portion of the signal.

In some aspects, the at least one data point associated with the distilling liquid comprises at least one of a wavelength, a waveform, or a reflection measurement indicative of a property of the distilling liquid.

In some aspects, a transmitter configured to transmit the signal through the external face of the container housing the distilling liquid is attached to the external face of the container.

In some aspects, the method further comprises: adjusting, by a controller, at least one distillation parameter based on the at least one distilling characteristic output by the machine-learning model.

In some aspects, the sensor is configured to measure at least one property of the distilling liquid comprising at least one of temperature, pressure, pH, flow rate, or alcohol concentration.

In some aspects, the method further comprises: receiving, by the one or more processors, the at least one data point from at least one of the sensor or the one or more memories prior to inputting the at least one data point into the machine-learning model.

In some aspects, at least one distilling characteristic associated with the distilling liquid is indicative of at least one of a purity level, a distillation completion state, or another distillation-related parameter.

In some aspects, the at least one data point associated with the distilling liquid includes at least one of a volume, a color, a proof, a temperature, a humidity, or an evaporation rate.

In some aspects, measuring the at least one data point is performed by at least one of a radar sensor, a dielectric sensor, an ultrasonic transducer, an environmental sensor, a near infrared sensor, or an ultraviolet-visible sensor.

In some aspects, the method further comprises: generating, by the machine-learning model, a compliance report based on the at least one distilling characteristic associated with the distilling liquid; and transmitting the compliance report to a user.

In some aspects, the machine-learning model comprises at least one of a Gaussian process regression model, a convolutional neural network, a long short-term memory network, or a hybrid CNN-LSTM model.

In some aspects, the machine-learning model is trained on training data comprising a plurality of data points associated with one or more distilling liquids, and wherein the machine-learning model is trained to predict, based on the training data, one or more distilling characteristics associated with the one or more distilling liquids.

A method for analyzing a liquid in a distilling system, the method comprising: monitoring a distilling liquid with at least one sensor system, wherein the at least one sensor system comprises: at least one transmission antenna positioned on an external face of a tank, the at least one transmission antenna configured to transmit a signal into the tank; and at least one receiving antenna, configured to receive the transmitted signal; collecting at least one distilling data point from the at least one sensor system; receiving and analyzing the at least one distilling data point using an artificial intelligence system, the artificial intelligence system comprising a machine-learning model, wherein: the machine-learning model is at least one of a gaussian process regression, a convolutional neural network, a long short-term memory, and a hybrid convolution neural network long short-term memory; determining at least one distilling characteristic of the distilling liquid using the artificial intelligence system; and transmitting the at least one distilling characteristic to at least one device associated with a user.

In some aspects, the distilling data point is at least one of a volume, a color, a proof, a temperature, a humidity, and an evaporation rate.

In some aspects, the at least one sensor system is at least one of a radar sensor, a dielectric sensor, an ultrasonic transducer, an environmental sensor, a near infrared sensor, and an ultraviolet-visible sensor.

In some aspects, the method may include tracking the at least one distilling data point and the at least one distilling characteristic; and comparing them, via the artificial intelligence system, against a user-input dataset.

In some aspects, the method may include calculating an optimal aging duration and a bottling time via the artificial intelligence system.

In some aspects, the method may include alerting the user that the distilling liquid is in an ideal aging window, wherein the ideal aging window is in the user-input dataset.

In some aspects, the method may include determining a distilling recommendation for an optimal aging time and a yield improvement via the artificial intelligence system; and transmitting the distilling recommendation to the at least one device associated with the user.

In some aspects, the distilling liquid is contained within a barrel; and the at least one sensor system is non-invasive.

In some aspects, one or more apparatuses, comprising one or more memories including executable instructions and one or more processors configured to execute the executable instructions, cause the one or more apparatuses to perform one or more of the methods as described above.

In some aspects, one or more apparatuses, comprising one or more memories and one or more processors, coupled to the one or more memories, may be configured to cause the one or more apparatuses to perform one or more of the methods as described above.

In some aspects, one or more apparatuses, comprising one or more memories and one or more processors, coupled to the one or more memories, may be configured to perform one or more of the methods as described above.

In some aspects, one or more apparatuses, comprising means for performing any one of the methods as described above, may be configured to perform one or more of the methods as described above.

In some aspects, one or more non-transitory computer-readable media may comprise executable instructions that, when executed by one or more processors of one or more apparatuses, cause the one or more apparatuses to perform one or more of the methods as described above.

In some aspects, one or more computer program products embodied on one or more computer-readable storage media may comprise code for performing one or more of the methods as described above.

An apparatus for analyzing a liquid in a distilling system, the apparatus comprising: at least one sensor system configured to measure at least one distilling data point of a distilling liquid; and a computing device configured to receive the at least one distilling data point from the at least one sensor system and analyze the at least one distilling data point via an artificial intelligence system, wherein: the artificial intelligence system is configured to determine at least one distilling characteristic of the distilling liquid; and the artificial intelligence system is configured to track the at least one distilling data point and at least one distilling characteristic.

It is to be understood that the specific devices and processes illustrated in the attached drawings and described in the following specification are exemplary embodiments of the inventive concepts defined in the appended claims.

Hence, specific dimensions and other physical characteristics relating to the embodiments disclosed herein are not to be considered as limiting, unless the claims expressly state otherwise.

In the foregoing description, it will be readily appreciated by those skilled in the art that modifications may be made to the invention without departing from the concepts disclosed herein. Such modifications are to be considered as included in the following claims, unless the claims by their language expressly state otherwise.

Variations described as exemplary embodiments of the present invention can be realized in any combination desirable for each particular application. Thus, particular limitations, and/or embodiment enhancements described herein, which may have particular limitations, need be implemented in methods, systems, and/or apparatuses including one or more concepts describe with relation to exemplary embodiments of the present invention.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112, sixth paragraph, unless the element is expressly recited using the phrase "means for" or "step for." These following claims should be construed to maintain the proper protection for the present invention.

In the foregoing description, it will be readily appreciated by those skilled in the art that modifications may be made to the invention without departing from the concepts disclosed herein. Such modifications are to be considered as included in the following claims, unless the claims by their language expressly state otherwise.

Terms and phrases used in this document, and variations thereof, unless otherwise expressly stated, should be construed as open-ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future.

Likewise, where this document refers to technologies that would be apparent or known to one of ordinary skill in the art, such technologies encompass those apparent or known to the skilled artisan now or at any time in the future. Furthermore, the use of plurals can also refer to the singular, including without limitation when a term refers to one or more of a particular item; likewise, the use of a singular term can also include the plural, unless the context dictates otherwise.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

There has thus been outlined, rather broadly, the more important features of the disclosure in order that the detailed description thereof may be better understood, and in order that the present contribution to the art may be better appreciated. There are additional features of the disclosure that will be described hereinafter, and which will also form the subject matter of the claims appended hereto. The features listed herein, and other features, aspects and advantages of the present disclosure will become better understood with reference to the following description and appended claims.

While various embodiments of the present disclosure have been described above, it should be understood that they have been presented by way of example only, and not of limitation. Likewise, the various diagrams may depict an example architectural or other configuration for the invention, which is provided to aid in understanding the features and functionality that can be included in the invention. The invention is not restricted to the illustrated example architectures or configurations, but the desired features can be implemented using a variety of alternative architectures and configurations.

Indeed, it will be apparent to one of skill in the art how alternative functional configurations can be implemented to implement the desired features of the present disclosure. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present invention should not be limited by any of the above-described exemplary embodiments.

What is claimed is:

1. An apparatus for analyzing a liquid comprising:
   a sensor comprising:
      a transmitter configured to transmit an electromagnetic signal through an external surface of a barrel housing a liquid and into the barrel, wherein the transmitter comprises an antenna element positioned external to the barrel; and
      a receiver configured to receive an electromagnetic return signal associated with the transmitted electromagnetic signal;
   one or more memories; and
   one or more processors, coupled to the one or more memories, configured to:

derive at least one data point associated with the liquid based on the transmitted electromagnetic signal and the electromagnetic return signal;

input the at least one data point into a machine-learning model, wherein the machine-learning model is trained on training data comprising a plurality of data points associated with liquids having known alcohol content values; and output, by the machine-learning model, based on the input, an alcohol content of the liquid.

2. The apparatus of claim 1, wherein the at least one data point comprises at least one of a signal-strength change, a frequency shift, or a phase shift.

3. The apparatus of claim 1, wherein the transmitter is attached to the external surface of the barrel.

4. The apparatus of claim 1, further comprising:

a controller configured to adjust at least one process parameter of a monitoring system based on the alcohol content of the liquid.

5. The apparatus of claim 1, wherein the sensor comprises at least one of a radar sensor or a dielectric sensor.

6. The apparatus of claim 1, wherein the liquid comprises at least one of a distilled spirit or a fermented liquid.

7. The apparatus of claim 6, wherein the one or more processors are configured to track changes in the alcohol content over an aging period of the liquid in the barrel.

8. The apparatus of claim 1, wherein the one or more processors are configured to obtain one or more features based on the at least one data point for input to the machine-learning model.

9. The apparatus of claim 1, wherein the one or more processors are further configured to:

derive a plurality of data points at different time intervals during an aging period of the liquid in the barrel; and input the plurality of data points into the machine-learning model to track changes in the alcohol content over the aging period.

10. The apparatus of claim 1, further comprising:

one or more environmental sensors configured to measure at least one of temperature or humidity external to the barrel, wherein the one or more processors are configured to input data from the one or more environmental sensors into the machine-learning model along with the at least one data point.

11. The apparatus of claim 1, wherein the one or more processors are further configured to:

generate a traceability record comprising at least one of:

a timestamp associated with the derived at least one data point, the alcohol content output by the machine-learning model, or an identifier associated with the barrel; and store the traceability record in a distributed ledger.

12. The apparatus of claim 1, wherein the one or more processors are further configured to:

compare the alcohol content output by the machine-learning model to a target alcohol content range; and generate an alert when the alcohol content is within the target alcohol content range.

13. A method for analyzing a liquid, the method comprising:

transmitting an electromagnetic signal through an external surface of a barrel housing the liquid and into the barrel, wherein the electromagnetic signal is transmitted from an antenna element positioned external to the barrel;

receiving an electromagnetic return signal associated with the transmitted electromagnetic signal;

deriving at least one data point associated with the liquid based on the transmitted electromagnetic signal and the electromagnetic return signal;

storing the at least one data point in one or more memories;

inputting, by one or more processors, the at least one data point into a machine-learning model, wherein the machine-learning model is trained on training data comprising a plurality of data points associated with liquids having known alcohol content values; and outputting, by the machine-learning model, based on the input, an alcohol content of the liquid.

14. The method of claim 13, wherein the at least one data point comprises at least one of a signal-strength change, a frequency shift, or a phase shift.

15. The method of claim 13, wherein the antenna element is attached to the external surface of the barrel.

16. The method of claim 13, further comprising:

adjusting, by a controller, at least one process parameter of a monitoring system based on the alcohol content of the liquid.

17. The method of claim 13, wherein the liquid comprises at least one of a distilled spirit or a fermented liquid.

18. A system for analyzing a liquid comprising:

a transmitter to transmit an electromagnetic signal, wherein the transmitter comprises an antenna element positioned external to a barrel containing a liquid;

a receiver to receive an electromagnetic return signal associated with the transmitted electromagnetic signal;

one or more memories; and one or more processors, coupled to the one or more memories, to:

derive at least one data point associated with the liquid based on the transmitted electromagnetic signal and the electromagnetic return signal;

input the at least one data point into a machine-learning model, wherein the machine-learning model is trained on training data comprising a plurality of data points associated with liquids having known alcohol content values; and output, by the machine-learning model, based on the input, an alcohol content of the liquid.

19. The system of claim 18, wherein:

the one or more processors are configured to track changes in the alcohol content over an aging period of the liquid in the barrel; and the liquid comprises at least one of a distilled spirit or fermented liquid.

20. The system of claim 18, further comprising:

a controller configured to adjust at least one process parameter of a monitoring system based on the alcohol content of the liquid.

* * * * *